United States Patent
Li et al.

(10) Patent No.: US 10,647,690 B2
(45) Date of Patent: May 12, 2020

(54) 2,3-EPOXY SUCCINYL DERIVATIVE, PREPARATION METHOD AND USE THEREOF

(71) Applicant: Institute of Pharmacology and Toxicology Academy of Military Medical Sciences P.L.A. China, Beijing (CN)

(72) Inventors: Song Li, Beijing (CN); Junhai Xiao, Beijing (CN); Xiaoye Zhang, Beijing (CN); Hongliang Wang, Beijing (CN); Wu Zhong, Beijing (CN); Zhibing Zheng, Beijing (CN); Yunde Xie, Beijing (CN); Xingzhou Li, Beijing (CN); Xinbo Zhou, Beijing (CN); Xiaokui Wang, Beijing (CN)

(73) Assignee: Institute of Pharmacology and Toxicology Academy of Military Medical Sciences P.L.A. China, Bejing (CN)

( * ) Notice: Subject to any disclaimer, the term of this patent is extended or adjusted under 35 U.S.C. 154(b) by 0 days.

(21) Appl. No.: 16/081,204

(22) PCT Filed: Mar. 2, 2017

(86) PCT No.: PCT/CN2017/075453
§ 371 (c)(1),
(2) Date: Aug. 30, 2018

(87) PCT Pub. No.: WO2017/148417
PCT Pub. Date: Sep. 8, 2017

(65) Prior Publication Data
US 2019/0062290 A1 Feb. 28, 2019

(30) Foreign Application Priority Data
Mar. 3, 2016 (CN) .......................... 2016 1 0119872

(51) Int. Cl.
*C07D 303/48* (2006.01)
*C07D 405/12* (2006.01)
*A61K 31/5377* (2006.01)
*A61K 31/541* (2006.01)
*A61K 31/336* (2006.01)
(Continued)

(52) U.S. Cl.
CPC .......... *C07D 303/48* (2013.01); *A61K 31/336* (2013.01); *A61K 31/4025* (2013.01); *A61K 31/427* (2013.01); *A61K 31/4523* (2013.01); *A61K 31/5377* (2013.01); *A61K 31/541* (2013.01); *A61P 19/00* (2018.01); *A61P 35/00* (2018.01); *A61P 37/02* (2018.01);
(Continued)

(58) Field of Classification Search
CPC .............. A61K 31/336; A61K 31/4025; A61K 31/427; A61K 31/4523; A61K 31/5377; A61K 31/541; A61P 19/00; A61P 35/00; A61P 37/02; C07D 301/27; C07D 303/48; C07D 405/12; C07D 417/12
See application file for complete search history.

(56) References Cited

U.S. PATENT DOCUMENTS

| 4,393,228 | A | 7/1983 | Sawada et al. |
| 5,556,853 | A | 9/1996 | Tsubotani et al. |
| 5,935,959 | A | 8/1999 | Inoue et al. |

FOREIGN PATENT DOCUMENTS

| CN | 1112555 A | 11/1995 |
| CN | 1195343 A | 10/1998 |

(Continued)

OTHER PUBLICATIONS

Inoue, CN 1195343, 1998 (English translation) (Year: 1998).*
(Continued)

*Primary Examiner* — Umamaheswari Ramachandran
(74) *Attorney, Agent, or Firm* — Sterne, Kessler, Goldstein & Fox P.L.L.C.

(57) ABSTRACT

The present invention relates to a 2,3-epoxy succinyl derivative, a preparation method and a use thereof, in particular, the present invention relates to a compound represented by Formula (1), a racemate or an optical isomer thereof, a solvate thereof, or a pharmaceutically acceptable salt thereof. The compound according to the present invention has good inhibitory activity and/or selectivity against cathepsin, especially Cathepsin B, can be used in the treatment of multiple diseases associated with cathepsin, for example, osteoporosis, rheumatoid arthritis and osteoarthritis that are associated with Cathepsin K, Ebola virus infection, a degenerative disease and an autoimmune disease that are associated with Cathepsin L, S, especially Cathepsin B-related tumor diseases, such as gastric cancer, cervical cancer, lung cancer, breast cancer, prostate cancer, bladder cancer, colon cancer, neuroglioma, and melanoma.

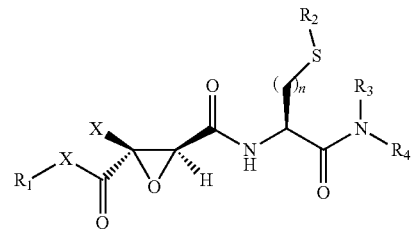

Formula (1)

16 Claims, No Drawings

(51) Int. Cl.
*A61K 31/4025* (2006.01)
*A61K 31/4523* (2006.01)
*A61K 31/427* (2006.01)
*C07D 417/12* (2006.01)
*A61P 19/00* (2006.01)
*A61P 37/02* (2006.01)
*A61P 35/00* (2006.01)
*C07D 301/27* (2006.01)

(52) U.S. Cl.
CPC ......... *C07D 301/27* (2013.01); *C07D 405/12* (2013.01); *C07D 417/12* (2013.01)

(56) References Cited

FOREIGN PATENT DOCUMENTS

| | | |
|---|---|---|
| CN | 101808634 A | 8/2010 |
| EP | 0 808 839 A1 | 11/1997 |
| WO | WO 95/32954 A1 | 12/1995 |
| WO | WO 2008/042480 A2 | 4/2008 |

OTHER PUBLICATIONS

Tsubotani, CN 1112555 A. (Published Nov. 29, 1995) (English translation) (Year: 1995).*

International Search Report (ISR) for PCT/CN2017/075453; I.A. fd: Mar. 2, 2017; dated Jun. 5, 2017, State Intellectual Property Office of the P.R. China, Beijing, China.

International Preliminary Report on Patentability (IPRP) (Chapter I of the Patent Cooperation Treaty) (PCT Rule 44bis) for PCT/CN2017/075453; I.A. fd: Mar. 2, 2017; dated Sep. 4, 2018, by the International Bureau of WIPO, Geneva, Switzerland.

Office action for Chinese Patent Application No. 201610119872.9, dated Mar. 20, 2019, China National Intellectual Property Administration, Beijing City, China.

Haidong Liu, "Design, synthesis and screening of cathepsin K selective inhibitors." China Doctoral Dissertations and Master's Thesis Volume of Medicine & Public Health, 9:E079-23 (Oct. 15, 2005.).

* cited by examiner

2,3-EPOXY SUCCINYL DERIVATIVE, PREPARATION METHOD AND USE THEREOF

TECHNICAL FIELD

The present invention belongs to medical field, in particular, relates to a 2,3-epoxy succinyl derivative, a preparation method and a use thereof, wherein the compound can be used as a cathepsin inhibitor, for the treatment of tumor, osteoporosis, Ebola virus infection, rheumatoid arthritis and osteoarthritis, an autoimmune disease or a degenerative disease.

BACKGROUND ART

Proteases are the major participants in the proteolysis in human body, and can be classified into serine proteases, cysteine proteases, aspartyl proteases, threonine proteases, metalloproteinases, etc. depending on proteolytic mechanism. Current studies mainly focus on cysteine proteases wherein papain-like cysteine proteases are the largest subfamily. Papain-like cysteine proteases in mammals belong to cathepsins. Cathepsins, most members of which are present in lysosomes, can be activated in an acidic environment, and include most of the cysteine proteases, and a small number of aspartic proteases (Cathepsin D, E) and serine proteases (Cathepsin A, G). Depending on substrate specificity, cathepsins can also be classified into endopeptidases (Cathepsin B, F, H, K, L, S, V), exopeptidases (Cathepsin B, C, H, X), amino-peptidases (Cathepsin C, H) and carboxypeptidases (Cathepsin B, X). Cathepsins in human body mainly include Cathepsin B, C, F, H, K, L, O, S, V, W and X, which are closely related to a variety of physiological and pathological processes in human body. Cathepsins are highly conservative in sequence, and their steric structure consists of two domains (i.e. L (Left) domain and R (Right) domain) that are almost the same size, and between the two domains, there is a V-shaped active site cleft, in which the active residues, such as Cys25 in the L domain and His159 and Asn175 in the R domain, are exposed.

Cathepsin B, which is one of the most studied enzyme among all cysteine proteases, is widely present in a variety of tissues in mammals, and is the first lysosomal protease that was found to be associated with breast cancer. In addition, Cathepsin B is also closely associated with the development and progression of a variety of human tumors. Tumor cells can secrete Cathepsin B. This secretory Cathepsin B cannot be uptaken by lysosomes due to the lack of a recognition marker for mannose-6-phosphate receptor, and therefore is generally present in the form of proenzyme in endochylema and extracellular region. Since tumor cells can acidify their surrounding environment, they can activate the proenzyme to form active Cathepsin B. The activated Cathepsin B can not only participate in the degradation of extracellular matrix components, but also activate the proteolysis cascade reaction, finally resulting in the generation of a substance capable of degrading a variety of extracellular matrix components. In addition, as compared to Cathepsin B secreted by normal cells, the activity of Cathepsin B secreted by tumor cells is not influenced, and is even enhanced in neutral and alkaline environments. Therefore, the expression level and/or activity of Cathepsin B was found to be increased in a variety of human and animal tumors such as gastric cancer, bladder cancer, colon cancer, neuroglioma, and melanoma. It was reported that in the tissues of malignant tumor such as cervical cancer, lung cancer, breast cancer, and prostate cancer, the expression and activity of Cathepsin B was 2 times or even 3 to 9 times higher than that of the adjacent normal tissues, and it was believed that an increase in the activity and concentration of Cathepsin B was a risk factor for tumor invasion, metastasis, and poor prognosis in patients with transitional cell carcinoma.

Normal bone metabolism in human body depends on the dynamic balance between bone formation and bone resorption. Osteoporosis relates to a metabolic imbalance between bone resorption and bone formation, and is a disease developed when bone resorption exceeds bone formation. Osteoporosis is a common disease or a frequently-occurring disease found in old people, especially menopausal and postmenopausal women. During bone resorption, osteoclasts are first attached to the bone surface so as to form a relatively sealed microenvironment for bone resorption, secrete protons and proteases, dissolve bone minerals, and then degrade bone matrix, resulting in bone void formation. There are two major enzymes involved in the degradation of bone matrix during osteolysis, i.e. cysteine proteases and matrix metalloproteinases, and among cysteine proteases, Cathepsin K plays a major role. Cathepsin K is selectively and abundantly expressed in osteoclasts, and its physiological substrate is the type I collagen with a content of 95% in the organic bone matrix. Furthermore, Cathepsin K can also degrade osteopontin and osteonectin in bone matrix, and is a cysteine protease that is expressed in the highest level in osteoclasts and has the strongest osteolytic activity, and its ability of degrading bone collagen is much higher than that of other matrix metalloproteinases. Cathepsin K is a key enzyme during bone resorption, and is also a hotspot in osteoporosis research in recent years. In addition to Cathepsin K, Cathepsin L is also present in the resorption microenvironment formed by osteoclasts, and has a strong collagen-dissolving ability and is also directly involved in the degradation of bone matrix. In addition, it has been demonstrated in studies that Cathepsin B and S exhibit bone-resorption ability in vive and in vitro, and are also associated with the development of osteoporosis.

Rheumatoid arthritis (RA) is a chronic systemic autoimmune disease characterized by inflammation of synovial membrane of joint. Continuous recurrence of synovitis can lead to destruction of cartilage and bone in joint, joint dysfunction, and even disability. Osteoarthritis (OA) is a common disease causing joint pain, resulted from non-inflammatory lesions in movable joints due to the degeneration of articular cartilage and the formation of new bone on the surface and edge of joint. Cartilage contains two main components, one of which is type II collagen that can form a 3-D fiber network structure to make the tissue extensible, and the other of which is aggrecan that ensures the tenacity of cartilage, excessive degradation of either of the two protein components will lead to the cartilage destruction in joint. It has been found in studies that the degradation of type II collagen was only associated with matrix metalloproteinase (secreted by chondrocyte) and Cathepsin K. The expression level of Cathepsin K was increased in the joints of RA and OA patients, and Cathepsin K could be further activated by inflammatory cytokines, indicating that Cathepsin K may be the main participant in cartilage destruction in RA and OA. In addition, it has also been found in many experiments that Cathepsin B and Cathepsin L were expressed in high levels in synovial membrane and synovial fluid of joints in RA patients, all the cathepsins appeared in the inflammatory joint could hydrolyze aggrecan, and Cathepsin B could also play an indirect role by participating in the proteolytic cascade reaction in the joint and activating matrix metalloproteinase precursor.

It is found in the current researches that Ebola virus infection is closely associated with the type I membrane-fusion protein GP encoded by a viral gene. The membrane-fusion protein GP consists of two subunits, GP1 and GP2. An Ebola virus particle has an enveloped helical nucleocapsid. An enveloped virus cannot replicate its pathogenic gene unless the envelope protein is fused with a host cell membrane or endosomal membrane. When an Ebola virus invades a cell, upon the attachment of the virus to the cell surface, its envelope-fusion protein GP has to be bound to Cathepsin B or L to alter its conformation so that it can be fused with the host endosomal membrane and then has the carried genetic material injected into the cell, resulting in massive replication in the infected cell. Bale et al. have shown in their studies that the Ebola virus GP1 and GP2 proteins cannot accomplish conformational alteration and mediate fusion on their own in acidic conditions, and need to be bound to other cellular proteins so as to accomplish conformational alteration. In the article published by Kathryn Schornberg et al., it is demonstrated by the experiments using chemical inhibitors and small interfering RNAs that Cathepsin B and Cathepsin L play a role in Ebola virus glycoprotein-mediated infection. It is demonstrated in the study that Cathepsin B or L finally cleaved GP1 into a 19-Kd fragment. However, it is not clear yet as to how the fragment triggers enzyme fusion and induces fusion. Matthew Brecher et al. found by binding different forms of GPs to liposomes that when a 19-Kd fragment was fused with a liposome, the activation temperature was the lowest, indicating that it was the optimal form for fusion.

Cathepsin L can promote the invasion and metastasis of tumor by catalyzing the degradation of matrix membrane. Cathepsin L has been found to be highly expressed in various cancers such as kidney cancer, testicular cancer, breast cancer, ovarian cancer, colon cancer, bladder cancer and thyroid cancer. Cathepsin S also plays an important role in the pathogenesis of degenerative diseases and autoimmune diseases and is involved in the antigen presentation modulated by major histocompatibility complex class II molecules, and its overexpression is closely associated with tumor growth, angiogenesis, and metastasis.

The purpose of the present invention is to synthesize new cathepsin inhibitors for the treatment of a disease such as tumor, osteoporosis, arthritis, Ebola virus infection, rheumatoid arthritis, osteoarthritis, an autoimmune disease or a degenerative disease.

CONTENTS OF INVENTION

By conducting deep research, the present invention has obtained a series of structurally novel derivatives having an epoxysuccinic acid structure, which have high inhibitory activity and/or selectivity against cathepsin (especially Cathepsin B). The present invention is accomplished based on the discovery above.

In an aspect, the present invention relates to a compound represented by Formula (1), a racemate or an optical isomer thereof, a solvate thereof, or a pharmaceutically acceptable salt thereof, Formula (1)

wherein, $R_1$ represents a hydrogen atom, $C_1$-$C_{10}$ linear or branched alkyl, $C_3$-$C_{10}$cycloalkyl, $C_2$-$C_{10}$ linear or branched alkenyl, $C_2$-$C_{10}$ linear or branched alkynyl, aryl, aryl-$C_1$-$C_6$alkyl, heterocyclyl or heterocyclyl-$C_1$-$C_6$alkyl;

$R_2$ represents a hydrogen atom, $C_1$-$C_{10}$ linear or branched alkyl, $C_3$-$C_{10}$cycloalkyl, $C_1$-$C_{10}$alkylthio, $C_3$-$C_{10}$cycloalkylthio, $C_2$-$C_{10}$ linear or branched alkenyl, $C_2$-$C_{10}$ linear or branched alkynyl, aryl, aryl-$C_1$-$C_6$alkyl, heterocyclyl or heterocyclyl-$C_1$-$C_6$alkyl, optionally, wherein the $C_1$-$C_{10}$ linear or branched alkyl, $C_3$-$C_{10}$cycloalkyl, $C_1$-$C_{10}$alkylthio, $C_3$-$C_{10}$cycloalkylthio, $C_2$-$C_{10}$ linear or branched alkenyl, $C_2$-$C_{10}$ linear or branched alkynyl, aryl, aryl-$C_1$-$C_6$alkyl, heterocyclyl or heterocyclyl-$C_1$-$C_6$alkyl each is independently substituted with one or more substituents selected from the group consisting of: halogen, amino, cyano, trifluoromethyl, hydroxyl, nitro, $C_1$-$C_{10}$alkyl, $C_1$-$C_{10}$alkoxy and $C_1$-$C_{10}$alkylthio, optionally, wherein the $C_1$-$C_{10}$alkyl, $C_1$-$C_{10}$alkoxy or $C_1$-$C_{10}$alkylthio is further substituted with one or more substituents selected from the above-mentioned group;

X represents —O—, or —N($R_5$)—;

n is an integer from 0 to 5, preferably from 1 to 3;

$R_3$ and $R_4$ each independently represent a hydrogen atom, $C_1$-$C_{10}$ linear or branched alkyl, $C_3$-$C_{10}$cycloalkyl, $C_2$-$C_{10}$ linear or branched alkenyl, $C_2$-$C_{10}$ linear or branched alkynyl, aryl, aryl-$C_1$-$C_6$alkyl, heterocyclyl, heterocyclyl-$C_1$-$C_6$alkyl or benzofused-heterocyclyl, optionally, wherein the $C_1$-$C_{10}$ linear or branched alkyl, $C_3$-$C_{10}$cycloalkyl, $C_2$-$C_{10}$ linear or branched alkenyl, $C_2$-$C_{10}$ linear or branched alkynyl, aryl, aryl-$C_1$-$C_6$alkyl, heterocyclyl, heterocyclyl-$C_1$-$C_6$alkyl or benzofused-heterocyclyl each is independently substituted with one or more substituents selected from the group consisting of: halogen, amino, cyano, trifluoromethyl, hydroxyl, nitro, $C_1$-$C_{10}$alkyl, $C_1$-$C_{10}$alkoxy, $C_1$-$C_{10}$alkylthio, optionally, wherein the $C_1$-$C_{10}$alkyl, $C_1$-$C_{10}$alkoxy or $C_1$-$C_{10}$alkylthio is further substituted with one or more substituents selected from the above-mentioned group;

or, $R_3$ and $R_4$, together with the N atom to which they are linked, form a 5-8 membered heterocycle, optionally, the 5-8 membered heterocycle is substituted with one or more substituents selected from the group consisting of: halogen, hydroxyl, amino, $C_1$-$C_{10}$alkyl, $C_1$-$C_{10}$alkoxy, $C_1$-$C_{10}$alkylthio, aryl, oxy and ester group; $R_5$ represents a hydrogen atom, $C_1$-$C_{10}$ linear or branched alkyl, aryl, aryl-$C_1$-$C_6$alkyl, heterocyclyl or heterocyclyl-$C_1$-$C_6$alkyl.

In an embodiment of the present invention, $R_1$ represents a hydrogen atom, $C_1$-$C_{10}$ linear or branched alkyl, $C_3$-$C_{10}$cycloalkyl, $C_2$-$C_{10}$ linear or branched alkenyl or $C_2$-$C_{10}$ linear or branched alkynyl; preferably, $R_1$ represents a hydrogen atom, $C_1$-$C_6$ linear or branched alkyl; preferably, $R_1$ represents $C_1$-$C_4$ linear or branched alkyl, e.g. methyl or ethyl.

In an embodiment of the present invention, in the compound represented by Formula (1), a racemate or an optical isomer thereof, a solvate thereof, or a pharmaceutically acceptable salt thereof, $R_1$ represents a hydrogen atom.

In an embodiment of the present invention, in the compound represented by Formula (1), a racemate or an optical isomer thereof, a solvate thereof, or a pharmaceutically acceptable salt thereof, $R_1$ represents $C_1$-$C_{10}$ linear or branched alkyl.

In an embodiment of the present invention, in the compound represented by Formula (1), a racemate or an optical isomer thereof, a solvate thereof, or a pharmaceutically acceptable salt thereof, $R_1$ represents $C_3$-$C_{10}$cycloalkyl.

In an embodiment of the present invention, in the compound represented by Formula (1), a racemate or an optical isomer thereof, a solvate thereof, or a pharmaceutically acceptable salt thereof, $R_1$ represents $C_2$-$C_{10}$ linear or branched alkenyl.

In an embodiment of the present invention, in the compound represented by Formula (1), a racemate or an optical isomer thereof, a solvate thereof, or a pharmaceutically acceptable salt thereof, $R_1$ represents $C_2$-$C_{10}$ linear or branched alkynyl.

In an embodiment of the present invention, in the compound represented by Formula (1), a racemate or an optical isomer thereof, a solvate thereof, or a pharmaceutically acceptable salt thereof, $R_1$ represents $C_1$-$C_6$ linear or branched alkyl.

In an embodiment of the present invention, in the compound represented by Formula (1), a racemate or an optical isomer thereof, a solvate thereof, or a pharmaceutically acceptable salt thereof, $R_1$ represents $C_1$-$C_4$ linear or branched alkyl.

In an embodiment of the present invention, in the compound represented by Formula (1), a racemate or an optical isomer thereof, a solvate thereof, or a pharmaceutically acceptable salt thereof, $R_1$ represents ethyl.

In an embodiment of the present invention, in the compound represented by Formula (1), a racemate or an optical isomer thereof, a solvate thereof, or a pharmaceutically acceptable salt thereof, $R_1$ represents methyl.

In an embodiment of the present invention, in the compound represented by Formula (1), a racemate or an optical isomer thereof, a solvate thereof, or a pharmaceutically acceptable salt thereof, $R_1$ represents propyl.

In an embodiment of the present invention, in the compound represented by Formula (1), a racemate or an optical isomer thereof, a solvate thereof, or a pharmaceutically acceptable salt thereof, $R_1$ represents isopropyl.

In an embodiment of the present invention, in the compound represented by Formula (1), a racemate or an optical isomer thereof, a solvate thereof, or a pharmaceutically acceptable salt thereof, $R_1$ represents n-butyl.

In an embodiment of the present invention, in the compound represented by Formula (1), a racemate or an optical isomer thereof, a solvate thereof, or a pharmaceutically acceptable salt thereof, $R_1$ represents isobutyl.

In an embodiment of the present invention, in the compound represented by Formula (1), a racemate or an optical isomer thereof, a solvate thereof, or a pharmaceutically acceptable salt thereof, $R_1$ represents tert-butyl.

In an embodiment of the present invention, in the compound represented by Formula (1), a racemate or an optical isomer thereof, a solvate thereof, or a pharmaceutically acceptable salt thereof, $R_1$ represents n-pentyl.

In an embodiment of the present invention, in the compound represented by Formula (1), a racemate or an optical isomer thereof, a solvate thereof, or a pharmaceutically acceptable salt thereof, $R_1$ represents isopentyl.

In an embodiment of the present invention, in the compound represented by Formula (1), a racemate or an optical isomer thereof, a solvate thereof, or a pharmaceutically acceptable salt thereof, $R_1$ represents neopentyl.

In an embodiment of the present invention, in the compound represented by Formula (1), a racemate or an optical isomer thereof, a solvate thereof, or a pharmaceutically acceptable salt thereof, $R_1$ represents isopentyl.

In an embodiment of the present invention, in the compound represented by Formula (1), a racemate or an optical isomer thereof, a solvate thereof, or a pharmaceutically acceptable salt thereof, $R_1$ represents 1-methylbutyl.

In an embodiment of the present invention, in the compound represented by Formula (1), a racemate or an optical isomer thereof, a solvate thereof, or a pharmaceutically acceptable salt thereof, $R_1$ represents 1-ethylpropyl.

In an embodiment of the present invention, in the compound represented by Formula (1), a racemate or an optical isomer thereof, a solvate thereof, or a pharmaceutically acceptable salt thereof, $R_1$ represents 1,2-dimethylpropyl.

In an embodiment of the present invention, in the compound represented by Formula (1), a racemate or an optical isomer thereof, a solvate thereof, or a pharmaceutically acceptable salt thereof, $R_1$ represents 2-methylbutyl.

In an embodiment of the present invention, in the compound represented by Formula (1), a racemate or an optical isomer thereof, a solvate thereof, or a pharmaceutically acceptable salt thereof, $R_2$ represents a hydrogen atom, $C_1$-$C_6$ linear or branched alkyl or aryl-$C_1$-$C_4$alkyl; preferably, $R_2$ represents $C_1$-$C_4$ linear or branched alkyl or aryl-$C_1$-$C_4$alkyl, e.g. methyl, ethyl or benzyl.

In an embodiment of the present invention, in the compound represented by Formula (1), a racemate or an optical isomer thereof, a solvate thereof, or a pharmaceutically acceptable salt thereof, $R_2$ represents a hydrogen atom.

In an embodiment of the present invention, in the compound represented by Formula (1), a racemate or an optical isomer thereof, a solvate thereof, or a pharmaceutically acceptable salt thereof, $R_2$ represents $C_1$-$C_{10}$ linear or branched alkyl.

In an embodiment of the present invention, in the compound represented by Formula (1), a racemate or an optical isomer thereof, a solvate thereof, or a pharmaceutically acceptable salt thereof, $R_2$ represents $C_3$-$C_{10}$cycloalkyl.

In an embodiment of the present invention, in the compound represented by Formula (1), a racemate or an optical isomer thereof, a solvate thereof, or a pharmaceutically acceptable salt thereof, $R_2$ represents $C_1$-$C_{10}$alkylthio.

In an embodiment of the present invention, in the compound represented by Formula (1), a racemate or an optical isomer thereof, a solvate thereof, or a pharmaceutically acceptable salt thereof, $R_2$ represents $C_3$-$C_{10}$cycloalkylthio.

In an embodiment of the present invention, in the compound represented by Formula (1), a racemate or an optical isomer thereof, a solvate thereof, or a pharmaceutically acceptable salt thereof, $R_2$ represents $C_2$-$C_{10}$ linear or branched alkenyl.

In an embodiment of the present invention, in the compound represented by Formula (1), a racemate or an optical isomer thereof, a solvate thereof, or a pharmaceutically acceptable salt thereof, $R_2$ represents $C_2$-$C_{10}$ linear or branched alkynyl.

In an embodiment of the present invention, in the compound represented by Formula (1), a racemate or an optical In an embodiment of the present invention, in the compound represented by Formula (1), a racemate or an optical isomer thereof, a solvate thereof, or a pharmaceutically acceptable salt thereof, $R_2$ represents aryl.

In an embodiment of the present invention, in the compound represented by Formula (1), a racemate or an optical isomer thereof, a solvate thereof, or a pharmaceutically acceptable salt thereof, $R_2$ represents aryl-$C_1$-$C_6$alkyl.

In an embodiment of the present invention, in the compound represented by Formula (1), a racemate or an optical isomer thereof, a solvate thereof, or a pharmaceutically acceptable salt thereof, $R_2$ represents heterocyclyl.

In an embodiment of the present invention, in the compound represented by Formula (1), a racemate or an optical isomer thereof, a solvate thereof, or a pharmaceutically acceptable salt thereof, $R_2$ represents heterocyclyl-$C_1$-$C_6$alkyl.

In an embodiment of the present invention, in the compound represented by Formula (1), a racemate or an optical isomer thereof, a solvate thereof, or a pharmaceutically acceptable salt thereof, $R_2$ represents $C_1$-$C_6$ linear or branched alkyl.

In an embodiment of the present invention, in the compound represented by Formula (1), a racemate or an optical isomer thereof, a solvate thereof, or a pharmaceutically acceptable salt thereof, $R_2$ represents aryl-$C_1$-$C_4$alkyl.

In an embodiment of the present invention, in the compound represented by Formula (1), a racemate or an optical isomer thereof, a solvate thereof, or a pharmaceutically acceptable salt thereof, $R_2$ represents aryl-$C_1$-$C_4$alkyl.

In an embodiment of the present invention, in the compound represented by Formula (1), a racemate or an optical isomer thereof, a solvate thereof, or a pharmaceutically acceptable salt thereof, $R_2$ represents $C_1$-$C_4$ linear or branched alkyl.

In an embodiment of the present invention, in the compound represented by Formula (1), a racemate or an optical isomer thereof, a solvate thereof, or a pharmaceutically acceptable salt thereof, $R_2$ represents ethyl.

In an embodiment of the present invention, in the compound represented by Formula (1), a racemate or an optical isomer thereof, a solvate thereof, or a pharmaceutically acceptable salt thereof, $R_2$ represents methyl.

In an embodiment of the present invention, in the compound represented by Formula (1), a racemate or an optical isomer thereof, a solvate thereof, or a pharmaceutically acceptable salt thereof, $R_2$ represents propyl.

In an embodiment of the present invention, in the compound represented by Formula (1), a racemate or an optical isomer thereof, a solvate thereof, or a pharmaceutically acceptable salt thereof, $R_2$ represents isopropyl.

In an embodiment of the present invention, in the compound represented by Formula (1), a racemate or an optical isomer thereof, a solvate thereof, or a pharmaceutically acceptable salt thereof, $R_2$ represents n-butyl.

In an embodiment of the present invention, in the compound represented by Formula (1), a racemate or an optical isomer thereof, a solvate thereof, or a pharmaceutically acceptable salt thereof, $R_2$ represents isobutyl.

In an embodiment of the present invention, in the compound represented by Formula (1), a racemate or an optical isomer thereof, a solvate thereof, or a pharmaceutically acceptable salt thereof, $R_2$ represents tert-butyl.

In an embodiment of the present invention, in the compound represented by Formula (1), a racemate or an optical isomer thereof, a solvate thereof, or a pharmaceutically acceptable salt thereof, $R_2$ represents n-pentyl.

In an embodiment of the present invention, in the compound represented by Formula (1), a racemate or an optical isomer thereof, a solvate thereof, or a pharmaceutically acceptable salt thereof, $R_2$ represents isopentyl.

In an embodiment of the present invention, in the compound represented by Formula (1), a racemate or an optical isomer thereof, a solvate thereof, or a pharmaceutically acceptable salt thereof, $R_2$ represents neopentyl.

In an embodiment of the present invention, in the compound represented by Formula (1), a racemate or an optical isomer thereof, a solvate thereof, or a pharmaceutically acceptable salt thereof, $R_2$ represents isopentyl.

In an embodiment of the present invention, in the compound represented by Formula (1), a racemate or an optical isomer thereof, a solvate thereof or a pharmaceutically acceptable salt thereof, $R_2$ represents 1-methylbutyl.

In an embodiment of the present invention, in the compound represented by Formula (1), a racemate or an optical isomer thereof, a solvate thereof, or a pharmaceutically acceptable salt thereof, $R_2$ represents 1-ethylpropyl.

In an embodiment of the present invention, in the compound represented by Formula (1), a racemate or an optical isomer thereof, a solvate thereof, or a pharmaceutically acceptable salt thereof, $R_2$ represents 1,2-dimethylpropyl.

In an embodiment of the present invention, in the compound represented by Formula (1), a racemate or an optical isomer thereof, a solvate thereof, or a pharmaceutically acceptable salt thereof, $R_2$ represents 2-methylbutyl.

In an embodiment of the present invention, in the compound represented by Formula (1), a racemate or an optical isomer thereof, a solvate thereof, or a pharmaceutically acceptable salt thereof, $R_2$ represents benzyl.

In an embodiment of the present invention, in the compound represented by Formula (1), a racemate or an optical isomer thereof, a solvate thereof, or a pharmaceutically acceptable salt thereof, $R_2$ represents phenylethyl.

In an embodiment of the present invention, in the compound represented by Formula (1), a racemate or an optical isomer thereof, a solvate thereof, or a pharmaceutically acceptable salt thereof, $R_2$ represents phenylpropyl.

In an embodiment of the present invention, in the compound represented by Formula (1), a racemate or an optical isomer thereof, a solvate thereof, or a pharmaceutically acceptable salt thereof, $R_2$ represents phenylbutyl.

In an embodiment of the present invention, in the compound represented by Formula (1), a racemate or an optical isomer thereof, a solvate thereof, or a pharmaceutically acceptable salt thereof, $R_2$ is optionally substituted with one or more halogen.

In an embodiment of the present invention, in the compound represented by Formula (1), a racemate or an optical isomer thereof, a solvate thereof, or a pharmaceutically acceptable salt thereof, $R_2$ is optionally substituted with one or more amino groups.

In an embodiment of the present invention, in the compound represented by Formula (1), a racemate or an optical isomer thereof, a solvate thereof, or a pharmaceutically acceptable salt thereof, $R_2$ is optionally substituted with one or more cyano groups.

In an embodiment of the present invention, in the compound represented by Formula (1), a racemate or an optical isomer thereof, a solvate thereof, or a pharmaceutically acceptable salt thereof, $R_2$ is optionally substituted with one or more trifluoromethyl groups.

In an embodiment of the present invention, in the compound represented by Formula (1), a racemate or an optical isomer thereof, a solvate thereof, or a pharmaceutically acceptable salt thereof, $R_2$ is optionally substituted with one or more hydroxyl groups.

In an embodiment of the present invention, in the compound represented by Formula (1), a racemate or an optical isomer thereof, a solvate thereof, or a pharmaceutically acceptable salt thereof, $R_2$ is optionally substituted with one or more nitro groups.

In an embodiment of the present invention, in the compound represented by Formula (1), a racemate or an optical isomer thereof, a solvate thereof, or a pharmaceutically acceptable salt thereof, $R_2$ is optionally substituted with one or more $C_1$-$C_{10}$alkyl groups.

In an embodiment of the present invention, in the compound represented by Formula (1), a racemate or an optical isomer thereof, a solvate thereof, or a pharmaceutically acceptable salt thereof, $R_2$ is optionally substituted with one or more $C_1$-$C_{10}$alkoxy groups.

In an embodiment of the present invention, in the compound represented by Formula (1), a racemate or an optical isomer thereof, a solvate thereof, or a pharmaceutically acceptable salt thereof, $R_2$ is optionally substituted with one or more $C_1$-$C_{10}$alkylthio groups.

In an embodiment of the present invention, in the compound represented by Formula (1), a racemate or an optical isomer thereof, a solvate thereof, or a pharmaceutically acceptable salt thereof, $R_3$ and $R_4$ each independently represent $C_1$-$C_{10}$ linear or branched alkyl, $C_3$-$C_{10}$cycloalkyl, aryl, aryl-$C_1$-$C_6$alkyl, heterocyclyl, heterocyclyl-$C_1$-$C_6$alkyl or benzofused-heterocyclyl, optionally, wherein the $C_1$-$C_{10}$ linear or branched alkyl, $C_3$-$C_{10}$cycloalkyl, aryl, aryl-$C_1$-$C_6$alkyl, heterocyclyl, heterocyclyl-$C_1$-$C_6$alkyl or benzofused-heterocyclyl each is independently substituted with one or more substituents selected from the group consisting of: halogen, $C_1$-$C_{10}$alkyl, $C_1$-$C_{10}$alkoxy and $C_1$-$C_{10}$alkylthio, optionally, wherein the $C_1$-$C_{10}$alkyl, $C_1$-$C_{10}$alkoxy or $C_1$-$C_{10}$alkylthio is further substituted with one or more substituents selected from the above-mentioned group; or, $R_3$ and $R_4$, together with the N atom to which they are linked, form a 5-8 membered heterocycle, optionally, wherein the 5-8 membered heterocycle is substituted with one or more substituents selected from the group consisting of: halogen, hydroxyl, amino, $C_1$-$C_{10}$alkyl, $C_1$-$C_6$alkoxy, $C_1$-$C_6$alkylthio, aryl, oxy and ester group;

preferably, $R_3$ and $R_4$ each independently represent $C_1$-$C_6$ linear or branched alkyl, aryl-$C_1$-$C_6$alkyl, optionally, wherein the $C_1$-$C_6$ linear or branched alkyl or aryl-$C_1$-$C_6$alkyl each is independently substituted with one or more substituents selected from the group consisting of halogen, $C_1$-$C_4$alkyl and $C_1$-$C_4$alkoxy; or, $R_3$ and $R_4$, together with the N atom to which they are linked, form a 5-8 membered heterocycle, optionally, the 5-8 membered heterocycle is substituted with one or more substituents selected from the group consisting of: $C_1$-$C_4$alkyl, $C_1$-$C_4$alkoxy and aryl;

preferably, $R_3$ and $R_4$ each independently represent $C_1$-$C_6$ linear or branched alkyl (e.g. methyl, ethyl, n-propyl, isopropyl, n-butyl, sec-butyl, tert-butyl, isobutyl, n-pentyl, 3-methyl-butyl, 2-methyl-butyl, 1-methyl-butyl, 2,2-dimethyl-propyl, 1,1-dimethyl-propyl, 1,2-dimethyl-propyl, 1-ethyl-propyl, n-hexyl, 1-methyl-n-pentyl, 2-methyl-pentyl, 3-methyl-pentyl, 4-methyl-pentyl, 1,1-dimethyl-butyl, 2,2-dimethyl-butyl, 3,3-dimethyl-butyl, 1,2-dimethyl-butyl, 1,3-dimethyl-butyl, 2,3-dimethyl-butyl, 1-ethyl-butyl, 2-ethyl-butyl, 1,2,2-trimethyl-propyl or 1,1,2-trimethyl-propyl), or aryl-$C_1$-$C_6$alkyl (e.g. benzyl, phenylethyl, phenylpropyl or phenylbutyl), optionally, wherein the $C_1$-$C_6$ linear or branched alkyl, or aryl-$C_1$-$C_6$alkyl each is independently substituted with one or more substituents selected from the group consisting of halogen (e.g. fluorine, chlorine, bromine or iodine), $C_1$-$C_4$alkyl (e.g. methyl, ethyl, propyl or isopropyl), and $C_1$-$C_4$alkoxy (e.g. methoxy, ethoxy or propoxy); or, $R_3$ and $R_4$, together with the N atom to which they are linked, form a 5-8 membered heterocycle (e.g. a pyrrolidine ring, a thiazolidine ring, a oxazolidine ring, a piperidine ring, a morpholine ring, a thiomorpholine ring, a piperazine ring or a homopiperazine ring), optionally, wherein the 5-8 membered heterocycle is substituted with one or more substituents selected from the group consisting of: carbonyl, halogen (e.g. fluorine, chlorine, bromine or iodine), $C_1$-$C_4$alkyl (e.g. methyl, ethyl, propyl or isopropyl), and $C_1$-$C_4$alkoxy (e.g. methoxy, ethoxy or propoxy).

In an embodiment of the present invention, in the compound represented by Formula (1), a racemate or an optical isomer thereof, a solvate thereof, or a pharmaceutically acceptable salt thereof, $R_3$ represents H, and $R_4$ represents isopentyl, n-pentyl, 2-methylbutyl, n-propyl, n-butyl, n-hexyl, 1-methylbutyl, isobutyl, neopentyl, tert-pentyl, sec-butyl, 1-ethylpropyl, phenylpropyl, 4-methoxyphenylethyl, p-methoxyphenylethyl, 3-fluorophenylethyl, or 4-phenylbutyl; or, $R_3$ and $R_4$, together with the N atom to which they are linked, form 3-methylpiperidine, 2-ethylpiperidine, 3,5-dimethylpiperidine, 4-phenylpiperidine, tetrahydropyrrole, morpholine, tetrahydrothiazole, or thiomorpholine.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents $C_1$-$C_{10}$ linear or branched alkyl, $C_3$-$C_{10}$cycloalkyl, aryl, aryl-$C_1$-$C_6$alkyl, heterocyclyl, heterocyclyl-$C_1$-$C_6$alkyl or benzofused-heterocyclyl, optionally, wherein the $C_1$-$C_{10}$ linear or branched alkyl, $C_3$-$C_{10}$cycloalkyl, aryl, aryl-$C_1$-$C_6$alkyl, heterocyclyl, heterocyclyl-$C_1$-$C_6$alkyl or benzofused-heterocyclyl each is independently substituted with one or more substituents selected from the group consisting of: halogen, $C_1$-$C_{10}$alkyl, $C_1$-$C_{10}$alkoxy and $C_1$-$C_{10}$alkylthio, optionally, wherein the $C_1$-$C_{10}$alkyl, $C_1$-$C_{10}$alkoxy or $C_1$-$C_{10}$alkylthio is further substituted with one or more substituents selected from the above-mentioned group; or, $R_3$ and $R_4$, together with the N atom to which they are linked, form a 5-8 membered heterocycle, optionally, wherein the 5-8 membered heterocycle is substituted with one or more substituents selected from the group consisting of: halogen, hydroxyl, amino, $C_1$-$C_{10}$alkyl, $C_1$-$C_6$alkoxy, $C_1$-$C_6$alkylthio, aryl, oxy and ester group.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents $C_1$-$C_6$ linear or branched alkyl, or aryl-$C_1$-$C_6$alkyl, optionally, wherein the $C_1$-$C_6$ linear or branched alkyl, or aryl-$C_1$-$C_6$alkyl each is independently substituted with one or more substituents selected from the group consisting of halogen, $C_1$-$C_4$alkyl and $C_1$-$C_4$alkoxy; or, $R_3$ and $R_4$, together with the N atom to which they are linked, form a 5-8 membered heterocycle, optionally, the 5-8 membered heterocycle is substituted with one or more substituents selected from the group consisting of: $C_1$-$C_4$alkyl, $C_1$-$C_4$alkoxy and aryl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents $C_1$-$C_6$ linear or branched alkyl (e.g. methyl, ethyl, n-propyl, isopropyl, n-butyl, sec-butyl, tert-butyl, isobutyl, n-pentyl, 3-methyl-butyl, 2-methyl-butyl, 1-methyl-butyl, 2,2-dimethyl-propyl, 1,1-dimethyl-propyl, 1,2-dimethyl-propyl, 1-ethyl-propyl, n-hexyl, 1-methyl-n-pentyl, 2-methyl-pentyl, 3-methyl-pentyl, 4-methyl-pentyl, 1,1-dimethyl-butyl, 2,2-dimethyl-butyl, 3,3-dimethyl-butyl, 1,2-dimethyl-butyl, 1,3-dimethyl-butyl, 2,3-dimethyl-butyl, 1-ethyl-butyl, 2-ethyl-butyl, 1,2,2-trimethyl-propyl or 1,1,2-trimethyl-propyl), or aryl-$C_1$-$C_6$alkyl (e.g. benzyl, phenylethyl, phenylpropyl or phenylbutyl), optionally, wherein the $C_1$-$C_6$ linear or branched alkyl, or aryl-$C_1$-$C_6$alkyl each is independently substituted with one or more substituents selected from the group consisting of halogen (e.g. fluorine, chlorine, bromine or iodine), $C_1$-$C_4$alkyl (e.g. methyl, ethyl, propyl or isopropyl), and $C_1$-$C_4$alkoxy (e.g. methoxy, ethoxy or propoxy); or, $R_3$ and $R_4$, together with the N atom to which they are linked, form a 5-8 membered heterocycle (e.g. a pyrrolidine ring, a thiazolidine ring, a oxazolidine ring, piperidine ring, a morpholine ring, a thiomorpholine ring, a piperazine ring or a homopiperazine ring), optionally, wherein the 5-8 membered heterocycle is substituted with one or more substituents selected from the group consisting of: carbonyl, halogen (e.g. fluorine, chlorine, bromine or iodine), $C_1$-$C_4$alkyl (e.g. methyl, ethyl, propyl or isopropyl), and $C_1$-$C_4$alkoxy (e.g. methoxy, ethoxy or propoxy).

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents $C_1$-$C_6$ linear or branched alkyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents aryl-$C_1$-$C_6$alkyl, wherein the aryl is optionally substituted with one or more halogen (e.g. fluorine, chlorine, bromine or iodine).

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents aryl-$C_1$-$C_6$alkyl, wherein the aryl is optionally substituted with one or more $C_1$-$C_4$alkyl (e.g. methyl, ethyl, propyl or isopropyl).

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents aryl-$C_1$-$C_6$alkyl, wherein the aryl is optionally substituted with one or more $C_1$-$C_4$alkoxy (e.g. methoxy, ethoxy or propoxy).

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents methyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents ethyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents n-propyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents isopropyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents n-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents sec-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents tert-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents isobutyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents n-pentyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 3-methyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 2-methyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1-methyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 2,2-dimethyl-propyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1,1-dimethyl-propyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1,2-dimethyl-propyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1-ethyl-propyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents n-hexyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1-methyl-n-pentyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 2-methyl-pentyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 3-methyl-pentyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 4-methyl-pentyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1,1-dimethyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 2,2-dimethyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 3,3-dimethyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1,2-dimethyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1,3-dimethyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 2,3-dimethyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1-ethyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 2-ethyl-butyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1,2,2-trimethyl-propyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 1,1,2-trimethyl-propyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents benzyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents phenylethyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents phenylpropyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 4-methoxyphenylethyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents p-methoxyphenylethyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 3-fluorophenylethyl.

In an embodiment of the present invention, in the compound represented by Formula (1), a racemate or an optical isomer thereof, a solvate thereof, or a pharmaceutically acceptable salt thereof, $R_3$ represents a hydrogen atom, and $R_4$ represents 4-phenylbutyl.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form a 5-8 membered heterocycle (e.g. a pyrrolidine ring, a thiazolidine ring, a oxazolidine ring, a piperidine ring, a morpholine ring, a thiomorpholine ring, a piperazine ring or a homopiperazine ring), optionally, wherein the 5-8 membered heterocycle is substituted with one or more substituents selected from the group consisting of: carbonyl, halogen (e.g. fluorine, chlorine, bromine or iodine), $C_1$-$C_4$alkyl (e.g. methyl, ethyl, propyl or isopropyl), and $C_1$-$C_4$alkoxy (e.g. methoxy, ethoxy or propoxy).

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form a pyrrolidine ring.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form a thiazolidine ring.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form an oxazolidine ring.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form a piperidine ring.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form a morpholine ring.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form a thiomorpholine ring.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form a piperazine ring.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form a homopiperazine ring.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form 3-methylpiperidine.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form 2-ethylpiperidine.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form 3,5-dimethylpiperidine.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form 4-phenylpiperidine.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form tetrahydropyrrole.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form morpholine.

In an embodiment of the present invention, in the compound represented by Formula (1), a racemate or an optical isomer thereof, a solvate thereof, or a pharmaceutically acceptable salt thereof, $R_3$ and $R_4$, together with the N atom to which they are linked, form tetrahydrothiazole.

In an embodiment of the present invention, in the compound represented by Formula (1), a racemate or an optical isomer thereof, a solvate thereof, or a pharmaceutically acceptable salt thereof, X is —O—.

In an embodiment of the present invention, in the compound represented by Formula (1), a racemate or an optical isomer thereof, a solvate thereof, or a pharmaceutically acceptable salt thereof, n is an integer from 1 to 3, preferably 1 or 2.

In an embodiment of the present invention, in the compound represented by Formula (1), a racemate or an optical isomer thereof, a solvate thereof, or a pharmaceutically acceptable salt thereof, n is 0.

In an embodiment of the present invention, in the compound represented by Formula (1), a racemate or an optical isomer thereof, a solvate thereof, or a pharmaceutically acceptable salt thereof, n is 1.

In an embodiment of the present invention, in the compound represented by Formula (1), a racemate or an optical isomer thereof, a solvate thereof, or a pharmaceutically acceptable salt thereof, n is 2.

In an embodiment of the present invention, in the compound represented by Formula (1), a racemate or an optical isomer thereof, a solvate thereof, or a pharmaceutically acceptable salt thereof, n is 3.

In an embodiment of the present invention, in the compound represented by Formula (1), a racemate or an optical isomer thereof, a solvate thereof, or a pharmaceutically acceptable salt thereof, $R_1$ represents a hydrogen atom, $C_1$-$C_{10}$ linear or branched alkyl, $C_3$-$C_{10}$cycloalkyl, $C_2$-$C_{10}$ linear or branched alkenyl, $C_2$-$C_{10}$ linear or branched alkynyl; $R_2$ represents a hydrogen atom, $C_1$-$C_{10}$ linear or branched alkyl, $C_3$-$C_{10}$cycloalkyl, $C_1$-$C_{10}$alkylthio, $C_3$-$C_{10}$cycloalkylthio, $C_2$-$C_{10}$ linear or branched alkenyl, $C_2$-$C_{10}$ linear or branched alkynyl, aryl, aryl-$C_1$-$C_6$alkyl, heterocyclyl or heterocyclyl-$C_1$-$C_6$alkyl, optionally, wherein the $C_1$-$C_{10}$ linear or branched alkyl, $C_3$-$C_{10}$cycloalkyl, $C_1$-$C_{10}$alkylthio, $C_3$-$C_{10}$cycloalkylthio, $C_2$-$C_{10}$ linear or branched alkenyl, $C_2$-$C_{10}$ linear or branched alkynyl, aryl, aryl-$C_1$-$C_6$alkyl, heterocyclyl, or heterocyclyl-$C_1$-$C_6$alkyl each is independently substituted with one or more substituents selected from the group consisting of: halogen, amino, cyano, trifluoromethyl, hydroxyl, nitro, $C_1$-$C_{10}$alkyl, $C_1$-$C_{10}$alkoxy and $C_1$-$C_{10}$alkylthio, optionally, wherein the $C_1$-$C_{10}$alkyl or $C_1$-$C_{10}$alkoxy is further substituted with one or more substituents selected from the above-mentioned group;

X is —O—;

n is an integer from 1 to 3, preferably 1 or 2;

$R_3$ and $R_4$ each independently represent a hydrogen atom, $C_1$-$C_{10}$ linear or branched alkyl, $C_3$-$C_{10}$cycloalkyl, $C_2$-$C_{10}$ linear or branched alkenyl, $C_2$-$C_{10}$ linear or branched alkynyl, aryl, aryl-$C_1$-$C_6$alkyl, heterocyclyl, heterocyclyl-$C_1$-$C_6$alkyl, or benzofused-heterocyclyl, optionally, wherein the $C_1$-$C_{10}$ linear or branched alkyl, $C_3$-$C_{10}$cycloalkyl, $C_2$-$C_{10}$ linear or branched alkenyl, $C_2$-$C_{10}$ linear or branched alkynyl, aryl, aryl-$C_1$-$C_6$alkyl, heterocyclyl, heterocyclyl-$C_1$-$C_6$alkyl or benzofused-heterocyclyl each is independently substituted with one or more substituents selected from the group consisting of: halogen, amino, cyano, trifluoromethyl, hydroxyl, nitro, $C_1$-$C_{10}$alkyl, $C_1$-$C_{10}$alkoxy or $C_1$-$C_{10}$alkylthio, optionally, wherein the $C_1$-$C_{10}$alkyl, $C_1$-$C_{10}$alkoxy or $C_1$-$C_{10}$alkylthio is further substituted with one or more substituents selected from the above-mentioned group; or, $R_3$ and $R_4$, together with the N atom to which they are linked, form a 5-8 membered heterocycle, optionally, wherein the 5-8 membered heterocycle is substituted with one or more substituents selected from the group consisting of: halogen, hydroxyl, amino, $C_1$-$C_{10}$alkyl, $C_1$-$C_{10}$alkoxy, $C_1$-$C_{10}$alkylthio, aryl, oxy and ester group.

In a particular embodiment of the present invention, in the compound represented by Formula (1), a racemate or an optical isomer thereof, a solvate thereof, or a pharmaceutically acceptable salt thereof, $R_1$ represents a hydrogen atom, $C_1$-$C_6$ linear or branched alkyl;

$R_2$ represents a hydrogen atom, $C_1$-$C_6$ linear or branched alkyl, or aryl-$C_1$-$C_4$alkyl;

X is —O—;

n is 1 or 2;

$R_3$ and $R_4$ each independently represent $C_1$-$C_{10}$ linear or branched alkyl, $C_3$-$C_{10}$cycloalkyl, aryl, aryl-$C_1$-$C_6$alkyl, heterocyclyl, heterocyclyl-$C_1$-$C_6$alkyl or benzofused-heterocyclyl, optionally, wherein the $C_1$-$C_{10}$ linear or branched alkyl, $C_3$-$C_{10}$cycloalkyl, aryl, aryl-$C_1$-$C_6$alkyl, heterocyclyl, heterocyclyl-$C_1$-$C_6$alkyl or benzofused-heterocyclyl each is independently substituted with one or more substituents selected from the group consisting of: halogen, $C_1$-$C_{10}$alkyl, $C_1$-$C_{10}$alkoxy and $C_1$-$C_{10}$alkylthio, optionally, wherein the $C_1$-$C_{10}$alkyl, $C_1$-$C_{10}$alkoxy or $C_1$-$C_{10}$alkylthio is further substituted with one or more substituents selected from the above-mentioned group; or, $R_3$ and $R_4$, together with the N atom to which they are linked, form a 5-8 membered heterocycle, optionally, wherein the 5-8 membered heterocycle is substituted with one or more substituents selected from the group consisting of: halogen, hydroxyl, amino, $C_1$-$C_{10}$alkyl, $C_1$-$C_6$alkoxy, $C_1$-$C_6$alkylthio, aryl, oxy and ester group.

In a particular embodiment of the present invention, in the compound represented by Formula (1), a racemate or an optical isomer thereof, a solvate thereof, or a pharmaceutically acceptable salt thereof, $R_1$ represents $C_1$-$C_4$ linear or branched alkyl;

$R_2$ represents $C_1$-$C_4$ linear or branched alkyl or aryl-$C_1$-$C_4$alkyl;

X is —O—;

n is 1 or 2;

$R_3$ and $R_4$ each independently represent $C_1$-$C_6$ linear or branched alkyl, or aryl-$C_1$-$C_6$alkyl, optionally, wherein the $C_1$-$C_6$ linear or branched alkyl, or aryl-$C_1$-$C_6$alkyl each is independently substituted with one or more substituents selected from the group consisting of halogen, $C_1$-$C_4$alkyl and $C_1$-$C_4$alkoxy; or, $R_3$ and $R_4$, together with the N atom to which they are linked, form a 5-8 membered heterocycle, optionally, wherein the 5-8 membered heterocycle is substituted with one or more substituents selected from the group consisting of: $C_1$-$C_4$alkyl, $C_1$-$C_4$alkoxy and aryl.

In an embodiment of the present invention, in a compound represented by Formula (1), a racemate or an optical isomer thereof, a solvate thereof, or a pharmaceutically acceptable salt thereof, $R_1$ represents $C_1$-$C_4$ linear or branched alkyl, e.g. ethyl;

$R_2$ represents $C_1$-$C_4$ linear or branched alkyl (e.g. methyl) or aryl-$C_1$-$C_4$alkyl (e.g. benzyl);

X is —O—;

n is 1 or 2;

$R_3$ represents H, $R_4$ represents $C_1$-$C_6$ linear or branched alkyl (e.g. isopentyl, n-pentyl, 2-methylbutyl, n-propyl, n-butyl, n-hexyl, 1-methylbutyl, isobutyl, neopentyl, tert-pentyl, sec-butyl, I-ethylpropyl), or aryl-$C_1$-$C_6$alkyl (e.g. phenylpropyl, phenylethyl, 4-phenylbutyl), optionally, wherein the $C_1$-$C_6$ linear or branched alkyl, or aryl-$C_1$-$C_6$alkyl each is independently substituted with one or more substituents selected from the group consisting of halogen (e.g. fluorine), $C_1$-$C_4$alkyl (e.g. methyl) and $C_1$-$C_4$alkoxy (e.g. methoxy); or, $R_3$ and $R_4$, together with the N atom to which they are linked, form a 5-8 membered heterocycle (e.g. piperidine, tetrahydropyrrole, morpholine, tetrahydrothiazole, thiomorpholine), optionally, wherein the 5-8 membered heterocycle is substituted with one or more substituents selected from the group consisting of: $C_1$-$C_4$alkyl (e.g. methyl, ethyl), $C_1$-$C_4$alkoxy and aryl (e.g. phenyl).

In an embodiment of the present invention, in a compound represented by Formula (1), a racemate or an optical isomer thereof, a solvate thereof, or a pharmaceutically acceptable salt thereof, $R_1$ represents ethyl;

$R_2$ represents methyl or benzyl;

X is —O—;

n is 1 or 2;

$R_3$ represents H, and $R_4$ represents isopentyl, n-pentyl, 2-methylbutyl, n-propyl, n-butyl, n-hexyl, 1-methylbutyl, isobutyl, neopentyl, tert-pentyl, sec-butyl, 1-ethylpropyl, phenylpropyl, 4-methoxyphenylethyl, p-methoxyphenylethyl, 3-fluorophenylethyl, or 4-phenylbutyl; or, $R_3$ and $R_4$, together with the N atom to which they are linked, form 3-methylpiperidine, 2-ethylpiperidine, 3,5-dimethylpiperidine, 4-phenylpiperidine, tetrahydropyrrole, morpholine, tetrahydrothiazole, or thiomorpholine.

In a particular embodiment of the present invention, in the compound of Formula (1), a racemate or an optical isomer thereof, a solvate thereof, or a pharmaceutically or physiologically acceptable salt thereof, the compound is selected from the group consisting of:

(2s, 3 s)-2-ethoxycarbonyl-3-[2-[(s)-4-methylthio-1-carbonyl-1-(isopentylamino)butane]formylamino]epoxysuccinic acid (Compound 1);

(2s, 3s)-2-ethoxycarbonyl-3-[2-[(s)-4-methylthio-1-carbonyl-1-(pentylamino)butane]formylamino]epoxysuccinic acid (Compound 2);

(2s, 3s)-2-ethoxycarbonyl-3-[2-[(s)-4-methylthio-1-carbonyl-1-(2-methylbutylamino) butane]formylamino]epoxysuccinic acid (Compound 3);

(2s, 3s)-2-ethoxycarbonyl-3-[2-[(s)-4-methylthio-1-carbonyl-1-(propylamino)butane]formylamino]epoxysuccinic acid (Compound 4);

(2s, 3s)-2-ethoxycarbonyl-3-[2-[(s)-4-methylthio-1-carbonyl-1-(hexylamino)butane]formylamino]epoxysuccinic acid (Compound 5);

(2s, 3s)-2-ethoxycarbonyl-3-[2-[(s)-4-methylthio-1-carbonyl-1-(1-methylbutylamino) butane]formylamino]epoxysuccinic acid (Compound 6);

(2s, 3s)-2-ethoxycarbonyl-3-[2-[(s)-4-methylthio-1-carbonyl-1-(3-methylpiperidinyl) butane]formylamino]epoxysuccinic acid (Compound 7);

(2s, 3s)-2-ethoxycarbonyl-3-[2-[(s)-4-methylthio-1-carbonyl-1-(3-phenylpropylamino) butane]formylamino]epoxysuccinic acid (Compound 8);

(2s, 3s)-2-ethoxycarbonyl-3-[2-[(s)-4-methylthio-1-carbonyl-1-(isobutylamino)butane]formylamino]epoxysuccinic acid (Compound 9);

(2s, 3s)-2-ethoxycarbonyl-3-[2-[(s)-4-methylthio-1-carbonyl-1-(4-methoxyphenylethyl amino)butane]formylamino]epoxysuccinic acid (Compound 10);

(2s, 3s)-2-ethoxycarbonyl-3-[2-[(s)-4-methylthio-1-carbonyl-1-(tetrahydropyrrolyl)butane]formylamino]epoxysuccinic acid (Compound 11);

(2s, 3s)-2-ethoxycarbonyl-3-[2-[(s)-4-methylthio-1-carbonyl-1-(morpholinyl)butane]formylamino]epoxysuccinic acid (Compound 12);

(2s, 3s)-2-ethoxycarbonyl-3-[2-[(s)-4-methylthio-1-carbonyl-1-(phenylpiperidinyl)butane]formylamino]epoxysuccinic acid (Compound 13);

(2s, 3s)-2-ethoxycarbonyl-3-[2-[(s)-3-benzylthio-1-carbonyl-1-(2-methylbutylamino) propane]formylamino]epoxysuccinic acid (Compound 14);

(2s, 3s)-2-ethoxycarbonyl-3-[2-[(s)-3-benzylthio-1-carbonyl-1-(neopentylamino)propane]formylamino]epoxysuccinic acid (Compound 15);

(2s, 3s)-2-ethoxycarbonyl-3-[2-[(s)-3-benzylthio-1-carbonyl-1-(tert-pentylamino)propane]formylamino]epoxysuccinic acid (Compound 16);

(2s, 3s)-2-ethoxycarbonyl-3-[2-[(s)-3-benzylthio-1-carbonyl-1-(propylamino)propane]formylamino]epoxysuccinic acid (Compound 17);

(2s, 3s)-2-ethoxycarbonyl-3-[2-[(s)-3-benzylthio-1-carbonyl-1-(hexylamino)propane]formylamino]epoxysuccinic acid (Compound 18);

(2s, 3s)-2-ethoxycarbonyl-3-[2-[(s)-3-benzylthio-1-carbonyl-1-(1-methylpropylamino) propane]formylamino]epoxysuccinic acid (Compound 19);

(2s, 3s)-2-ethoxycarbonyl-3-[2-[(s)-3-benzylthio-1-carbonyl-1-(4-phenylbutylamino) propane]formylamino]epoxysuccinic acid (Compound 20);

(2s, 3s)-2-ethoxycarbonyl-3-[2-[(s)-3-benzylthio-1-carbonyl-1-(p-methylphenylethyl amino)propane]formylamino]epoxysuccinic acid (Compound 21);

(2s, 3s)-2-ethoxycarbonyl-3-[2-[(s)-3-benzylthio-1-carbonyl-1-(tetrahydropyrrolyl) propane]formylamino]epoxysuccinic acid (Compound 22);

(2s, 3s)-2-ethoxycarbonyl-3-[2-[(s)-3-benzylthio-1-carbonyl-1-(4-phenylpiperidinyl) propane]formylamino]epoxysuccinic acid (Compound 23);

(2s, 3s)-2-ethoxycarbonyl-3-[2-[(s)-3-benzylthio-1-carbonyl-1-(3-fluorophenylethylamino)propane]formylamino] epoxysuccinic acid (Compound 24);

(2s, 3s)-2-ethoxycarbonyl-3-[2-[(s)-3-benzylthio-1-carbonyl-1-(morpholinyl)propane]formylamino]epoxysuccinic acid (Compound 25);

(2s, 3s)-2-ethoxycarbonyl-3-[2-[(s)-3-benzylthio-1-carbonyl-1-(4-methoxyphenylethyl amino)propane]formylamino]epoxysuccinic acid (Compound 26);

(2s, 3s)-2-ethoxycarbonyl-3-[2-[(s)-4-methylthio-1-carbonyl-1-(neopentylamino)butane]formylamino]epoxysuccinic acid (Compound 30);

(2s, 3s)-2-ethoxycarbonyl-3-[2-[(s)-4-methylthio-1-carbonyl-1-(tert-pentylamino)butane]formylamino]epoxysuccinic acid (Compound 31);

(2s, 3s)-2-ethoxycarbonyl-3-[2-[(s)-4-methylthio-1-carbonyl-1-(tert-butylamino)butane]formylamino]epoxysuccinic acid (Compound 32);

(2s, 3s)-2-ethoxycarbonyl-3-[2-[(s)-4-methylthio-1-carbonyl-1-(p-methylphenylethyl amino)butane]formylamino] epoxysuccinic acid (Compound 33);

(2s, 3s)-2-ethoxycarbonyl-3-[2-[(s)-4-methylthio-1-carbonyl-1-(3-fluorophenylethyl amino)butane]formylamino] epoxysuccinic acid (Compound 34);

(2s, 3s)-2-ethoxycarbonyl-3-[2-[(s)-4-methylthio-1-carbonyl-1-(2-ethylpiperidinyl)butane]formylamino]epoxysuccinic acid (Compound 35);

(2s, 3s)-2-ethoxycarbonyl-3-[2-[(s)-4-methylthio-1-carbonyl-1-(thiomorpholinyl)butane]formylamino]epoxysuccinic acid (Compound 36);

(2s, 3s)-2-ethoxycarbonyl-3-[2-[(s)-4-methylthio-1-carbonyl-1-(tetrahydrothiazolyl) butane]formylamino]epoxysuccinic acid (Compound 38);

(2s, 3s)-2-ethoxycarbonyl-3-[2-[(s)-4-methylthio-1-carbonyl-1-(1-ethylpropylamino) butane]formylamino]epoxysuccinic acid (Compound 39);

(2s, 3s)-2-ethoxycarbonyl-3-[2-[(s)-4-methylthio-1-carbonyl-1-(4-phenylbutylamino) butane]formylamino]epoxysuccinic acid (Compound 40);

(2s, 3s)-2-ethoxycarbonyl-3-[2-[(s)-4-methylthio-1-carbonyl-1-(3,5-dimethylpiperidinyl) butane]formylamino]epoxysuccinic acid (Compound 41);

(2s, 3s)-2-ethoxycarbonyl-3-[2-[(s)-3-benzylthio-1-carbonyl-1-(1-methylbutylamino) propane]formylamino]epoxysuccinic acid (Compound 42);

(2s, 3s)-2-ethoxycarbonyl-3-[2-[(s)-3-benzylthio-1-carbonyl-1-(1-ethylpropylamino) propane]formylamino]epoxysuccinic acid (Compound 43);

(2s, 3s)-2-ethoxycarbonyl-3-[2-[(s)-3-benzylthio-1-carbonyl-1-(isobutylamino)propane]formylamino]epoxysuccinic acid (Compound 44);

(2s, 3s)-2-ethoxycarbonyl-3-[2-[(s)-3-benzylthio-1-carbonyl-1-(3-phenylpropylamino) propane]formylamino]epoxysuccinic acid (Compound 45);

(2s, 3s)-2-ethoxycarbonyl-3-[2-[(s)-3-benzylthio-1-carbonyl-1-(thiomorpholinyl)propane]formylamino]epoxysuccinic acid (Compound 46);

(2s, 3s)-2-ethoxycarbonyl-3-[2-[(s)-3-benzylthio-1-carbonyl-1-(tetrahydrothiazolyl) propane]formylamino]epoxysuccinic acid (Compound 47);

(2s, 3s)-2-ethoxycarbonyl-3-[2-[(s)-3-benzylthio-1-carbonyl-1-(3-methylpiperidinyl) propane]formylamino]epoxysuccinic acid (Compound 48);

(2s, 3s)-2-ethoxycarbonyl-3-[2-[(s)-3-benzylthio-1-carbonyl-1-(2-ethylpiperidinyl) propane]formylamino]epoxysuccinic acid (Compound 49);

(2s, 3s)-2-ethoxycarbonyl-3-[2-[(s)-3-benzylthio-1-carbonyl-1-(3,5-dimethylpiperidinyl) propane]formylamino]epoxysuccinic acid (Compound 50);

(2s, 3s)-2-ethoxycarbonyl-3-[2-[(s)-3-benzylthio-1-carbonyl-1-(isopentylamino)propane]formylamino]epoxysuccinic acid (Compound 51); and (2s, 3s)-2-ethoxycarbonyl-3-[2-s)-3-benzylthio-1-carbonyl-1-(pentylamino)propane]formylamino]epoxysuccinic acid (Compound 52).

In another aspect, the present invention relates to a method for preparing the compound represented by Formula (1), a racemate or an optical isomer thereof, a solvate thereof, or a pharmaceutically acceptable salt thereof according to the present invention, comprising the following steps:

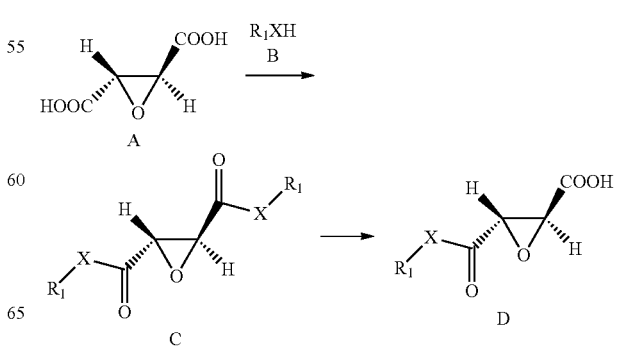

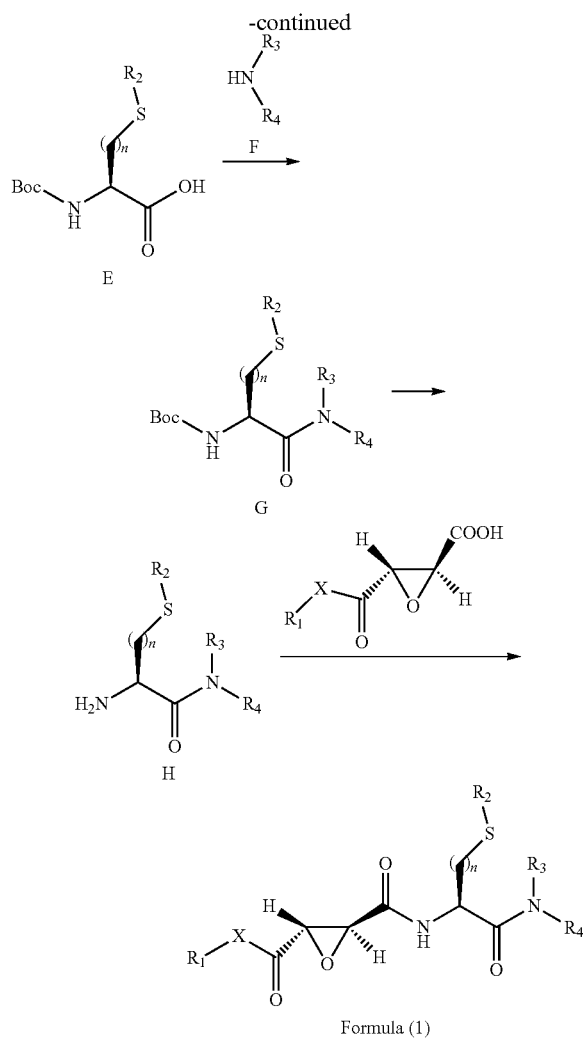

Formula (1)

(1) Compound A and Compound B are subjected to esterification or amidation reaction to produce Compound C;

(2) Compound C is subjected to selective hydrolysis to produce Compound D;

(3) Compound E and Compound F are subjected to condensation to produce Compound G;

(4) the amino-protecting group is removed from Compound G to produce Compound H; and (5) Compound H and the Compound D obtained in step (2) are subjected to condensation to produce a compound of Formula (1).

In a particular embodiment of the present invention, Compound A can be prepared by chiral separation of (+/−)-trans-epoxysuccinic acid and arginine.

In a particular embodiment of the present invention, in the step (1), the esterification reaction can be carried out in the presence of sulphuric acid.

In a particular embodiment of the present invention, in the step (2), potassium hydroxide is used as a base in the selective hydrolysis.

In a particular embodiment of the present invention, in the condensation of the step (3), DCC, HOBt, EDCI, HATU, HBTU, TBTU or PyBOP, and the like can be used as a condensation agent, and TEA, DIPEA, and the like can be used as a base.

In the third aspect, the present invention relates to a pharmaceutical composition, comprising the compound of Formula (1), a racemate or an optical isomer thereof, a solvate thereof, or a pharmaceutically acceptable salt thereof according to the first aspect of the present invention, and optionally one or more pharmaceutically acceptable carriers or excipients.

In another aspect, the present invention relates to use of the compound of Formula (1), a racemate or an optical isomer thereof, a solvate thereof, or a pharmaceutically acceptable salt thereof according to the first aspect of the present invention, or the pharmaceutical composition according to the third aspect of the present invention in the manufacture of a cathepsin inhibitor.

In an embodiment of the present invention, the cathepsin is selected from the group consisting of Cathepsin B, C, F, H, K, L, O, S, V, W and X, preferably, the cathepsin is selected from the group consisting of Cathepsin B, K, L and S.

In another aspect, the present invention relates to use of the compound of Formula (1), a racemate or an optical isomer thereof, a solvate thereof, or a pharmaceutically acceptable salt thereof according to the first aspect of the present invention, or the pharmaceutical composition according to the third aspect of the present invention in the manufacture of a medicament for treatment, prevention or adjuvant treatment of tumor.

In an embodiment of the present invention, the tumor is selected from the group consisting of kidney cancer, lymphoma, lung cancer, liver cancer, gastric cancer, testicular cancer, non-small cell lung cancer, breast cancer, ovarian cancer, colon cancer, bladder cancer and thyroid cancer.

In another aspect, the present invention relates to use of the compound of Formula (1), a racemate or an optical isomer thereof, a solvate thereof, or a pharmaceutically acceptable salt thereof according to the first aspect of the present invention, or the pharmaceutical composition according to the third aspect of the present invention in the manufacture of a medicament for prevention and/or treatment of osteoporosis, Ebola virus infection, rheumatoid arthritis, osteoarthritis, an autoimmune disease or a degenerative disease.

In an embodiment of the present invention, the autoimmune disease is selected from the group consisting of chronic lymphatic thyroiditis, hyperthyroidism, insulin-dependent diabetes mellitus, myasthenia gravis, chronic ulcerative colitis, pernicious anemia complicated with chronic atrophic gastritis, pulmonary hemorrhagic nephritis syndrome, pemphigoid, primary biliary cirrhosis and multiple cerebrospinal sclerosis.

In an embodiment of the present invention, the degenerative disease is selected from the group consisting of cardiovascular disease (e.g. hypertensive heart disease, cardiomyopathy, myocardial infarction, valvular heart disease), cerebral dysfunction (such as Alzheimer's disease and Down syndrome), and cataracta, etc.

The present invention further relates to the compound of Formula (1), a racemate or an optical isomer thereof, a solvate thereof, or a pharmaceutically acceptable salt thereof according to the first aspect of the present invention, or the pharmaceutical composition according to the third aspect of the present invention, for use in inhibition of cathepsin activity.

In an embodiment of the present invention, the cathepsin is selected from the group consisting of Cathepsin B, C, F, H, K, L, O, S, V, W and X, preferably, the cathepsin is selected from the group consisting of Cathepsin B, K, L and S.

The present invention further relates to the compound of Formula (1), a racemate or an optical isomer thereof, a solvate thereof, or a pharmaceutically acceptable salt thereof according to the first aspect of the present invention, or the pharmaceutical composition according to the third aspect of the present invention, for use in treatment, prevention or adjuvant treatment of tumor.

In an embodiment of the present invention, the tumor is selected from the group consisting of kidney cancer, lymphoma, lung cancer, liver cancer, gastric cancer, testicular cancer, non-small cell lung cancer, breast cancer, ovarian cancer, colon cancer, bladder cancer and thyroid cancer.

The present invention further relates to the compound of Formula (1), a racemate or an optical isomer thereof, a solvate thereof, or a pharmaceutically acceptable salt thereof according to the first aspect of the present invention, or the pharmaceutical composition according to the third aspect of the present invention, for use in prevention and/or treatment of osteoporosis, Ebola virus infection, rheumatoid arthritis, osteoarthritis, an autoimmune disease or a degenerative disease.

In an embodiment of the present invention, the autoimmune disease is selected from the group consisting of chronic lymphatic thyroiditis, hyperthyroidism, insulin-dependent diabetes mellitus, myasthenia gravis, chronic ulcerative colitis, pernicious anemia complicated with chronic atrophic gastritis, pulmonary hemorrhagic nephritis syndrome, pemphigoid, primary biliary cirrhosis and multiple cerebrospinal sclerosis.

In an embodiment of the present invention, the degenerative disease is selected from the group consisting of cardiovascular disease (e.g. hypertensive heart disease, cardiomyopathy, myocardial infarction, valvular heart disease), cerebral dysfunction (such as Alzheimer's disease and Down syndrome), and cataracta, etc.

The present invention relates to a method for inhibition of cathepsin activity, comprising administering to a subject in need thereof an effective amount of the compound of Formula (1), a racemate or an optical isomer thereof, a solvate thereof, or a pharmaceutically acceptable salt thereof according to the first aspect of the present invention, or the pharmaceutical composition according to the third aspect of the present invention.

In an embodiment of the present invention, the cathepsin is selected from the group consisting of Cathepsin B, C, F, H, K, L, O, S, V, W and X, preferably, the cathepsin is selected from the group consisting of Cathepsin B, K, L and S.

In an embodiment of the present invention, the subject is a mammal, such as a bovine, an equine, a caprid, a suidae, a canine, a feline, a rodent and a primate; wherein, the particularly preferred subject is a human.

The present invention relates to a method for treatment, prevention or adjuvant treatment of tumor, comprising administering to a subject in need thereof an effective amount of the compound of Formula (1), a racemate or an optical isomer thereof, a solvate thereof, or a pharmaceutically acceptable salt thereof according to the first aspect of the present invention, or the pharmaceutical composition according to the third aspect of the present invention.

In an embodiment of the present invention, the tumor is selected from the group consisting of kidney cancer, lymphoma, lung cancer, liver cancer, gastric cancer, testicular cancer, non-small cell lung cancer, breast cancer, ovarian cancer, colon cancer, bladder cancer and thyroid cancer.

In an embodiment of the present invention, the subject is a mammal, such as a bovine, an equine, a caprid, a suidae, a canine, a feline, a rodent and a primate; wherein, the particularly preferred subject is a human.

The present invention further relates to a method for prevention and/or treatment of osteoporosis, Ebola virus infection, rheumatoid arthritis, osteoarthritis, an autoimmune disease or a degenerative disease, comprising administering to a subject in need thereof an effective amount of the compound of Formula (1), a racemate or an optical isomer thereof, a solvate thereof, or a pharmaceutically acceptable salt thereof according to the first aspect of the present invention, or the pharmaceutical composition according to the third aspect of the present invention.

In an embodiment of the present invention, the subject is a mammal, such as a bovine, an equine, a caprid, a suidae, a canine, a feline, a rodent and a primate; wherein, the particularly preferred subject is a human.

In an embodiment of the present invention, the autoimmune disease is selected from the group consisting of chronic lymphatic thyroiditis, hyperthyroidism, insulin-dependent diabetes mellitus, myasthenia gravis, chronic ulcerative colitis, pernicious anemia complicated with chronic atrophic gastritis, pulmonary hemorrhagic nephritis syndrome, pemphigoid, primary biliary cirrhosis and multiple cerebrospinal sclerosis.

In an embodiment of the present invention, the degenerative disease is selected from the group consisting of cardiovascular disease (e.g. hypertensive heart disease, cardiomyopathy, myocardial infarction, valvular heart disease), cerebral dysfunction (such as Alzheimer's disease and Down syndrome), and cataracta, etc.

The terms used in the present invention are explained as follows. For a specific term, if its meanings in the present invention are different from the meanings as generally understood by a person skilled in the art, the meanings in the present invention will prevail; if no definition is made in the present invention, it has the meanings as generally understood by a person skilled in the art. Unless otherwise specified, the terms used in the present invention have the following meanings:

As used in the present invention, the term "$C_1$-$C_{10}$ linear or branched alkyl" refers to a linear or branched alkyl having 1-10 carbon atoms, for example, $C_1$-$C_6$ linear or branched alkyl, $C_1$-$C_4$ linear or branched alkyl. Particular examples include, but are not limited to methyl, ethyl, propyl, isopropyl, n-butyl, sec-butyl, tert-butyl, isobutyl, n-pentyl, 3-methyl-butyl, 2-methyl-butyl, 1-methyl-butyl, 2,2-dimethyl-propyl, 1,1-dimethyl-propyl, 1,2-dimethyl-propyl, 1-ethyl-propyl, n-hexyl, 1-methyl-n-pentyl, 2-methyl-pentyl, 3-methyl-pentyl, 4-methyl-pentyl, 1,1-dimethyl-butyl, 2,2-dimethyl-butyl, 3,3-dimethyl-butyl, 1,2-dimethyl-butyl, 1,3-dimethyl-butyl, 2,3-dimethyl-butyl, 1-ethyl-butyl, 2-ethyl-butyl, 1,2,2-trimethyl-propyl, 1,1,2-trimethyl-propyl, etc.

As used in the present invention, the term "$C_1$-$C_{10}$alkoxy" refers to a group having a structure of "$C_1$-$C_{10}$alkyl-O—", for example, $C_1$-$C_6$alkoxy, and $C_1$-$C_4$alkoxy, wherein $C_1$-$C_{10}$alkyl has the same meanings as the "$C_1$-$C_{10}$ linear or branched alkyl" as described above. Particular examples include, but are not limited to methoxy, ethoxy, propoxy, isopropoxy, n-butoxy, sec-butoxy, tert-butoxy, isobutoxy, pentoxy, 2-pentoxy, 3-pentoxy, isopentoxy, neopentoxy, sec-pentoxy, hexyloxy, 2-hexyloxy, 3-hexyloxy, etc.

As used in the present invention, the term "$C_1$-$C_{10}$alkylthio" can be understood in a similar way as "$C_1$-$C_{10}$alkoxy", except that the oxygen atom is replaced by a sulfur atom, for example, $C_1$-$C_6$alkylthio, and $C_1$-$C_4$alkylthio. Particular examples include, but are not limited to methylthio, ethylthio, propylthio, isopropylthio, etc.

As used in the present invention, the term "$C_3$-$C_{10}$cycloalkyl" refers to a saturated carbon ring group having 3-10 carbon atoms. The cycloalkyl may be a monocycle or a polycyclic fused system, and may be fused to an aromatic ring, for example, $C_3$-$C_8$cycloalkyl, $C_5$-$C_8$cycloalkyl, $C_5$-$C_7$cycloalkyl, $C_5$-$C_6$cycloalkyl, etc. Particular examples include, but are not limited to cyclopropyl, cyclobutyl, cyclopentyl, cyclohexyl, etc.

As used in the present invention, the term "$C_3$-$C_{10}$cycloalkoxy" refers to a group having a structure of "$C_3$-$C_{10}$cycloalkyl-O—", wherein $C_3$-$C_{10}$cycloalkyl has the same meanings as the $C_3$-$C_{10}$cycloalkyl described above, for example, $C_3$-$C_8$cycloalkoxy, $C_5$-$C_8$cycloalkoxy, $C_5$-$C_7$cycloalkoxy, $C_5$-$C_6$cycloalkoxy, etc. Particular examples include, but are not limited to cyclopropoxy, cyclobutoxy, cyclopentoxy, cyclohexyloxy, etc.

As used in the present invention, the term "$C_3$-$C_{10}$cycloalkylthio" can be understood in a similar way as $C_3$-$C_{10}$cycloalkoxy, except that the oxygen atom is replaced by a sulfur atom, for example, $C_3$-$C_8$cycloalkylthio, $C_5$-$C_8$cycloalkylthio, $C_5$-$C_7$cycloalkylthio, $C_5$-$C_6$cycloalkylthio, etc. Particular examples include, but are not limited to cyclopropylthio, cyclobutylthio, cyclopentylthio, cyclohexylthio, etc.

As used in the present invention, the term "$C_2$-$C_{10}$ linear or branched alkenyl" refers to a linear or branched hydrocarbon group having 2-10 carbon atoms and at least one carbon-carbon double bond, for example, $C_2$-$C_8$ linear or branched alkenyl, $C_2$-$C_6$ linear or branched alkenyl, $C_2$-$C_4$ linear or branched alkenyl. Particular examples include, but are not limited to vinyl, propenyl, butenyl, pentenyl, hexenyl, etc.

As used in the present invention, the term "$C_2$-$C_{10}$ linear or branched alkynyl" refers to a linear or branched hydrocarbon group having 2-10 carbon atoms and at least one carbon-carbon triple bond, for example, $C_2$-$C_8$ linear or branched alkynyl, $C_2$-$C_6$ linear or branched alkynyl, $C_2$-$C_4$ linear or branched alkynyl. Particular examples include, but are not limited to ethynyl, propynyl, butynyl, pentynyl, etc.

As used in the present invention, the term "halogen" refers to fluorine, chlorine, bromine and iodine.

As used in the present invention, the term "aryl" refers to an aromatic carbon ring group that is a monocycle (e.g. phenyl), a polycycle (e.g. naphthyl), or a fused ring (1, 2, 3, 4-tetrahydronaphthyl) having at least one aromatic ring, and is optionally substituted with one or more substituents selected from the group consisting of halogen, amino, cyano, trifluoromethyl, hydroxyl, nitro, $C_1$-$C_{10}$alkyl, $C_1$-$C_{10}$alkoxy, $C_1$-$C_{10}$alkylthio, aryl and heteroaryl. Particular examples include, but are not limited to phenyl, naphthyl, anthryl, phenanthryl, fluorenyl, indenyl, acenaphthenyl, 2-fluorophenyl, 3-fluorophenyl, 4-fluorophenyl, 2-methylphenyl, 3-methylphenyl, 4-methylphenyl, 2-methoxyphenyl, 3-methoxyphenyl, 4-methoxyphenyl, biphenylyl, etc.

As used in the present invention, the term "arylalkyl" refers to an alkyl as defined above, which is substituted with one or more aryl groups as defined above, for example, aryl-$C_1$-$C_6$alkyl, aryl-$C_1$-$C_4$alkyl. Particular examples include, but are not limited to benzyl, phenylethyl, phenylpropyl, phenylbutyl, etc.

As used in the present invention, the term "heterocyclyl" or "heterocycle" refers to a 3-10 membered monocycle or polycycle containing from at least one to at most four heteroatoms selected from the group consisting of N, O and S, which can be classified into an aliphatic heterocyclyl and an aromatic heterocyclyl, provided that the ring of the group does not contain two adjacent O or S atoms, preferably a 3-8 membered (e.g. 3 membered, 4 membered, 5 membered, 6 membered, 7 membered, 8 membered) aliphatic heterocyclyl or aromatic heterocyclyl. Optionally, the heterocyclyl can also be substituted with one or more substituents selected from the group consisting of halogen, amino, cyano, trifluoromethyl, hydroxyl, nitro, $C_1$-$C_{10}$alkyl, $C_1$-$C_6$haloalkyl, $C_2$-$C_6$alkenyl, $C_2$-$C_6$alkynyl, $C_1$-$C_6$alkylamino, di($C_1$-$C_6$alkyl)amino, $C_1$-$C_{10}$alkoxy, $C_1$-$C_6$haloalkoxy, $C_1$-$C_{10}$alkylthio, aryl and heteroaryl. Particular examples include, but are not limited to oxiranyl, oxocyclobutyl, pyrrolidinyl, tetrahydrofuranyl, dihydrofuryl, tetrahydrothienyl, pyrrolyl, furyl, thienyl, imidazolyl, oxazolyl, thiazolyl, piperidinyl, tetrahydropyranyl, morpholinyl, thiomorpholinyl, piperazinyl, pyridyl, pyranyl, pyrazinyl, pyrimidinyl, triazinyl, 2-methylpiperidinyl, 3-methylpiperidinyl, 4-methylpiperidinyl, 2-ethylpiperidinyl, 3-ethylpiperidinyl, 4-ethylpiperidinyl, 3,5-dimethylpiperidinyl, 2-phenylpiperidinyl, 3-phenylpiperidinyl, 3-phenylpiperidinyl, etc.

As used in the present invention, the term "benzofusedheterocyclyl" refers to a group formed by fusing a benzene ring with a heterocyclic compound, for example, benzofuran, indole, benzothiophene, benzoxazole, benzimidazole, benzothiazole, benzooxadiazole, benzotriazole, benzothiadiazole, quinoline, benzotetrahydrofuran, benzotetrahydropyrrole, benzotetrahydropyran, benzopiperidine, benzodioxane, phthalimide, or benzopiperazine, etc.

As used in the present invention, the term "oxy" refers to

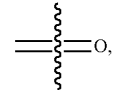

which can form a carbonyl group on the carbon atom of a heterocycle or is present in an enol form, for example, form a structure such as pyrrolidone, morpholinone, and pyridin-2-one.

As used in the present invention, the term "ester group" refers to a substituent having a structure of —COOR, wherein R represents alkyl, for example,

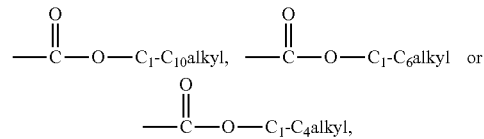

As used in the present invention, the term "more" includes two, three, four, or five, etc.

As used in the present invention, the term "optical isomer" includes all the possible optical isomers (such as enantiomers and diastereomers) of the compound of Formula (1) according to the present invention, for example, the R and S configurations of an asymmetric center.

The compound of Formula (1) or a pharmaceutically acceptable salt thereof according to the present invention may further form a solvate, such as a hydrate and an alcoholate. In general, a solvate form, formed from a pharmaceutically acceptable solvent such as water and ethanol, is equivalent to a non-solvate form. Said compound may also be a prodrug or a form that can release the active ingredient after metabolism in vivo. It is a well-known technique for a person skilled in the art to select and prepare a suitable prodrug derivative.

As used herein, the term "an effective amount" refers to an amount that is sufficient to achieve the desired preventive and/or therapeutic effect, for example, an amount that achieves the prevention or alleviation of the symptoms associated with a disease to be treated.

As used herein, the term "treatment/treating" refers to a therapeutic treatment and a prophylactic treatment, for the purpose of preventing or delaying (alleviating) the state or condition of a disease to be treated. If a subject received a therapeutic amount of a compound, or an isomer, a solvate or a pharmaceutically acceptable salt thereof, or a pharmaceutical composition thereof according to the method as described herein, and one or more indications and symptoms of the subject could be observed and/or be determined to be reduced or improved, the subject is successfully "treated". It should also be understood that the prevention or treatment of the state or condition of the disease includes not only complete prevention or treatment, but also incomplete prevention or treatment which, however, achieves some biologically or medically related results.

As used in the present invention, the term "an autoimmune disease" refers to a disease caused by autoimmune tissue destruction resulted from an immune response to an autoantigen in an organism, specifically refers to a disease associated with increased expression or activity of cathepsin, for example, chronic lymphatic thyroiditis, hyperthyroidism, insulin-dependent diabetes mellitus, myasthenia gravis, chronic ulcerative colitis, pernicious anemia complicated with chronic atrophic gastritis, pulmonary hemorrhagic nephritis syndrome, pemphigoid, primary biliary cirrhosis, and multiple cerebrospinal sclerosis.

As used in the present invention, the term "a degenerative disease" refers to a degenerative disease developed from an aging-induced disease, which is promoted by extensive damage to DNA, proteins, and other macromolecules due to the production of oxidation by-products during metabolism in human, including cancer, cardiovascular disease (e.g. hypertensive heart disease, cardiomyopathy, myocardial infarction, valvular heart disease), aging immune system, cerebral dysfunction (such as Alzheimer's disease and Down syndrome), cataracta, etc.

As used herein, the term "a pharmaceutical composition" means that it comprises one or more compounds, racemates or optical isomers thereof, solvates thereof, or pharmaceutically acceptable salts thereof as described herein, and pharmaceutically acceptable carriers or excipients. The purpose of a pharmaceutical composition is to promote the administration to an organism, and facilitate the absorption of active ingredients, so as to exert biological activity. The carriers described here include, but are not limited to, an ion exchanger, aluminum oxide, aluminum stearate, lecithin, serum protein such as human serum albumin, a buffer substance such as phosphate, glycerol, sorbic acid, potassium sorbate, a partial glyceride mixture of saturated plant fatty acid, water, a salt, or an electrolyte, such as protamine sulfate, disodium hydrogen phosphate, potassium hydrogen phosphate, sodium chloride, zinc salt, colloid silica, magnesium trisilicate, polyvinylpyrrolidone, cellulose substance, polyethylene glycol, carboxymethyl cellulose sodium, polyacrylic ester, beewax, and lanolin. The excipient used herein refers to an additive other than a main drug in a pharmaceutical formulation, which is stable in property, is not incompatible with the main drug, does not result in side effects, does not affect the therapeutic effect, is not easily deformed, cracked, moldy, and worm-damaged at room temperature, is not harmful to human body, has no physiological action, does not react with the main drug chemically or physically, does not influence the determination of the content of the main drug, and so on. The excipient can be, for example, a binding agent, a filler, a disintegrating agent, and a lubricant in a tablet; alcohol, vinegar, medicine juice, and the like in a pill of traditional Chinese medicine; a base material in a semi-solid formulation such as ointment and cream; and a preservative, an antioxidant, a flavoring agents, an aromatic, a co-solvent, an emulsifier, a solubilizer, an osmotic pressure regulator, a coloring agent, and the like in a liquid formulation.

The compound, a racemate or an optical isomer thereof, a solvate thereof, or a pharmaceutically acceptable salt thereof according to the present invention, or a pharmaceutical composition thereof can be administered by the following routes: parenteral, topical, intravenous, oral, subcutaneous, intraarterial, intradermal, percutaneous, rectal, intracranial, intraperitoneal, intranasal, and intramuscular route, or as an inhalant. Optionally, the composition may be administered in combination with an additional agent that at least has a certain effect on the treatment of various diseases.

The compound, a racemate or an optical isomer thereof, a solvate thereof, or a pharmaceutically acceptable salt thereof according to the present invention, or a pharmaceutical composition thereof may be prepared in any suitable dosage form depending on administration route.

When orally administered, the compound according to the present invention may be prepared in the form of any orally acceptable formulation, including, but not limited to a tablet, a capsule, an aqueous solution, or an aqueous suspension. The carriers for use in a tablet generally include lactose and maize starch. In addition, a lubricant such as magnesium stearate can also be added. Diluents for use in a capsule generally include lactose and dry maize starch. An aqueous suspension is generally obtained by mixing an active ingredient with a suitable emulsifier and a suitable suspending agent. Optionally, a sweetening agent, a flavoring agent or a coloring agent may be added to the above-mentioned forms of oral formulations.

When topically administered to skin, the compound according to the present invention may be prepared in a suitable form of an ointment, a lotion or a cream, wherein the active ingredient is suspended or dissolved in one or more carriers. The carriers for use in an ointment preparation include, but are not limited to: mineral oil, liquid paraffin, white vaseline, propylene glycol, polyethylene oxide, polypropylene oxide, emulsion wax and water; carriers for use in a lotion or a cream include, but are not limited to: mineral oil, sorbitan monostearate, Tween 60, hexadecylester wax, hexadecane aromatic alcohol, 2-octyl dodecanol, benzyl alcohol and water.

The compound according to the present invention may be administered in a form of a sterile formulation for injection, including a sterile injection water, an oil suspension or a sterile injection solution. The carriers and solvents for use therein include water, Ringer's solution, and isotonic sodium chloride solution. In addition, a sterile fixed oil can also be used as a solvent or a suspension medium, such as monoglyceride or diglyceride.

The pharmaceutical formulation according to the present invention includes any pharmaceutically applicable formulation, such as an oral formulation, and a parenteral formulation.

In the embodiments of the present invention, appropriate assays in vitro or in vivo are performed to determine the efficacy of the composition according to the present invention and whether the administration thereof is suitable for treating a disease or a medical condition in an individual. Examples of these assays are described in the following non-limiting Examples in combination with specific diseases or medical treatments. In general, an effective amount of the composition according to the present invention, which is sufficient to achieve a prophylactic or therapeutic effect, is from about 0.001 mg/kg body weight/day to about 10,000 mg/kg body weight/day. Under suitable conditions, the dose is from about 0.01 mg/kg body weight/day to about 1000 mg/kg body weight/day. The dose can range from about 0.01 to 1000 mg/kg body weight of a host every day, every two days, or every three days, more usually from 0.1 to 500 mg/kg body weight of a host. An exemplary therapeutic regimen is to administer once every two days, every week or every month. The agent is generally administered for several times, and the interval between single doses can be daily, weekly, monthly, or yearly. Alternatively, the agent may be administered in the form of a sustained-release formulation, and in this case, low-frequency administration is required. Dose and frequency are varied depending on the half-life of an agent in a subject, and can also be varied depending on whether it is a prophylactic treatment or a therapeutic treatment. In prophylactic application, a relatively low dose is administered at a relatively low-frequency interval for a long term. In therapeutic application, it sometimes needs to administer a relatively high dose at a relatively short interval until the progression of a disease is delayed or stopped, preferably until an individual shows a partial or complete improvement of the symptoms of the disease, and then a prophylactic regimen can be applied to the patient.

Beneficial Effects of the Invention

The present invention provides a class of epoxysuccinic acid derivatives, which have high inhibitory activity and/or selectively against cathepsin, especially Cathepsin B, can be used in the treatment of multiple diseases associated with cathepsin, for example, osteoporosis, rheumatoid arthritis and osteoarthritis that are associated with Cathepsin K, Ebola virus infection, and a degenerative disease and an autoimmune disease that are associated with Cathepsin L, S, especially Cathepsin B-related tumor diseases, such as gastric cancer, cervical cancer, lung cancer, breast cancer, prostate cancer, bladder cancer, colon cancer, neuroglioma, and melanoma.

Specific Modes for Carrying Out the Invention

The embodiments of the present invention are illustrated in detail by reference to the following examples. However, it is understood by those skilled in the art that the examples are used only for the purpose of illustrating the present invention, rather than limiting the protection scope of the present invention. When the conditions are not indicated in the Examples, the Examples are carried out under the conventional conditions or the conditions recommended by the manufacturers. The reagents or instruments used herein, the manufacturers of which are not indicated, are the conventional products that are commercially available.

In the following Examples, the specific optical rotation of compounds was measured by Polaar 3005 type Accuracy Automatic Polarimeter from Optical Activity Limited Company; $^1$H-NMR spectra were measured by Bruker ARX 400 type NMR spectrometer; and FAB mass spectra were measured by Agilent1260-G6230A High Resolution Mass Spectrometer.

Preparation of Intermediates

Intermediate 1: Preparation of (2S, 3S)-oxirane-2,3-dicarboxylic acid

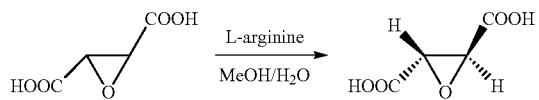 [SMILES: O=C(O)C1OC1C(=O)O ; O=C(O)[C@H]1O[C@@H]1C(=O)O]

(+/−)-trans-epoxysuccinic acid (178 g, 1.35 mol) was dissolved in methanol (2600 ml). L-arginine (234.9 g, 1.35 mol) was added to water (650 ml), and dissolved under heating. The resultant solution was then added dropwise to a solution of (+/−)-trans-epoxysuccinic acid in methanol under stirring, and finally a lot of undissolved substance appeared. After the addition, the resultant mixture was stirred overnight at room temperature. The precipitate was obtained by suction filtration, and washed with a mixed solvent (1000 ml) of methanol/water (4:1), to obtain a crude product (201.2 g). The crude product was recrystallized with methanol/water (2:1) (about 3000 ml) to obtain (+)-trans-epoxysuccinic acid (170.2 g, yield: 82.5%).

$^1$H-NMR (400 MHz, D$_2$O) 1.54-2.02 (4H, m), 3.22 (2H, t), 3.48 (2H, s), 3.84 (1H, t); $[\alpha]_D$+54.7 (c=1.00, H$_2$O); EI-MS (m/z): [M+H]$^+$ 133.

Intermediate 2: Preparation of diethyl (2S, 3S)-oxirane-2,3-dicarboxylate

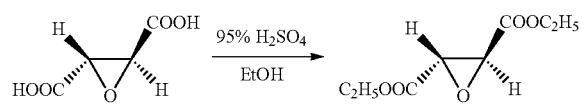

At room temperature, (+/−)-trans-epoxysuccinic acid (107.1 g, 0.35 mol) was suspended in ethanol (1050 ml), and stirred, and then 95% concentrated sulphuric acid (102.9 g, 1.05 mol) was added dropwise. After the addition, the resultant mixture was stirred and refluxed for 4.5 h. After the reaction was finished, the solvent of the mixture was removed by rotary evaporation. Ice water (200 ml) was added to the residue in the bottle, and the resultant solution was extracted with ethyl acetate for three times (300 ml*3). The ester phases extracted were combined, washed with saturated sodium bicarbonate aqueous solution (200 ml*2) and then with saturated saline solution (200*2), dried with anhydrous magnesium sulfate, subjected to suction filtration, and evaporated to dryness by rotary evaporation, to obtain a crude product. The crude product was purified by a chromatographic column to obtain a pure product, as colorless oily liquid (50.4 g, yield: 76.6%).

$^1$H-NMR (400 MHz, CDCl$_3$) 1.31 (6H, t), 3.66 (2H, s), 4.28 (4H, dq); $[\alpha]_D$+110.5 (c=1.12, EtOH); EI-MS (m/z): [M+H]$^+$ 189.

Intermediate 3: Preparation of ethyl (2S, 3S)-3-carboxylate-oxirane-2-carboxylic acid

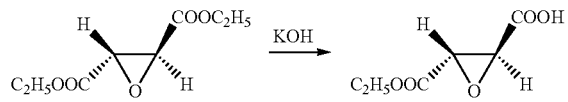

85% KOH (6.72 g, 0.1 mol) was added to ethanol (67 ml) to prepare an ethanol solution of KOH. Intermediate 2 (18.8 g, 0.1 mol) was added to ethanol (150 ml), and stirred, and then the ethanol solution of KOH was added dropwise at the temperature of 4-6° C. controlled by an ice-bath. After the addition, the resultant mixture was further stirred at 4-6° C. for 1 h, and then was warmed to room temperature and stirred for 4 h. After the reaction was finished, the solvent was removed by evaporation. Water (50 ml) was added to form a solution, which was washed with ethyl acetate (50 ml*2). Water phase was separated, and in an ice-bath, the water phase was acidified with 6N hydrochloric acid to PH=2, and extracted with ethyl acetate (70 ml*3). The ester phase was collected and washed with saturated saline solution (70 ml*2), dried with anhydrous magnesium sulfate, and subjected to suction filtration. The solvent in the resultant solution was removed to obtain the crude product of Intermediate 3 (13.1 g), as colorless oil, which was directly used in the next step without purification.

$^1$H-NMR (400 MHz, CDCl$_3$) 1.27-1.31 (3H, t), 3.59-3.62 (2H, s), 4.23-4.25 (2H, dq); EI-MS (m/z): [M+H]$^+$ 161.

Intermediate 4: Preparation of ethyl (2S, 3S)-3-(4-nitrophenoxycarbonyl)-oxirane-2-carboxylate

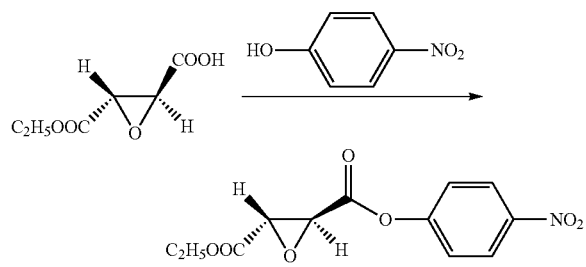

DCC (12.9 g, 0.0625 mol) was dissolved in ethyl acetate (26 ml), to form an ethyl acetate solution of DCC. Intermediate 3 (10 g) and p-nitrophenol (8.69 g, 0.0625 mol) were dissolved in ethyl acetate (55 ml), and stirred, the temperature was kept at 4-5° C., the ethyl acetate solution of DCC prepared was slowly added dropwise. The reaction was carried out at the low temperature for 3 h, and the resultant mixture was warmed to room temperature and reacted for 1 h. After the reaction was finished, the residue was filtrated off, the organic phase was washed with ethyl acetate (20 ml), and ethyl acetate phase was filtrated again. The solvent was removed by rotary evaporation to obtain a crude product. The crude product was recrystallized with ethyl acetate-cyclohexane to obtain Intermediate 4 (14.1 g, Yield: 65.8%), which was yellow needle-like.

$^1$H-NMR (400 MHz, DMSO) 1.26 (3H, t), 4.06 (1H, d), 4.08 (1H, d), 4.24 (2H, q), 7.58 (2H, d), 8.36 (2H, d); [α]$_D$+114.8 (c=1.00, AcOEt); EI-MS (m/z): [M+H]$^+$ 282.

Example 1 (2s, 3s)-2-ethoxycarbonyl-3-[2-[(s)-4-methylthio-1-carbonyl-1-(isopentylamino) butane] formylamino]epoxysuccinic acid (Compound 1)

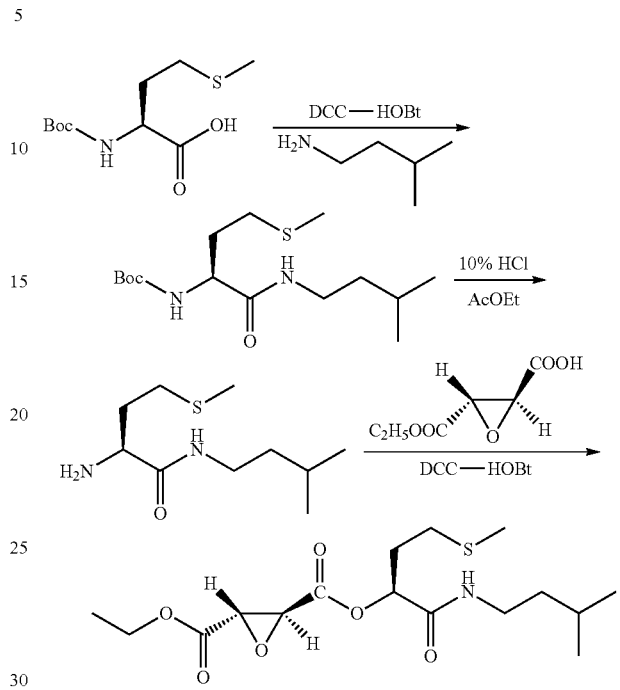

(1) DCC (10.32 g, 0.05 mol) was dissolved in ethyl acetate (20 ml), to form an ethyl acetate solution of DCC. N-(tert-butyoxycarbonyl)-L-methionine (12.49 g, 0.05 mol), isopentylamine (4.36 g, 0.05 mol) and HOBt (6.76 g, 0.05 mol) were dissolved in ethyl acetate (35 ml), and stirred in an ice-bath at 3-8° C. The ethyl acetate solution of DCC prepared was then added dropwise, and stirred at 3-8° C. for 1.5 h. The resultant mixture was warmed to room temperature and stirred for 2.5 h. After the reaction was finished, the impurities were filtrated off. The precipitate was washed with ethyl acetate (40 ml), and the filtrates were combined, and washed with 5% hydrochloric acid (100 ml), saturated saline solution (100 ml), saturated sodium bicarbonate (100 ml), and saturated saline water (100 ml) sequentially. The organic phase was dried with anhydrous magnesium sulfate, and evaporated to dryness by rotary evaporation, to obtain a crude product (14.45 g, yield: 96.1%), which was used directly in the next step without purification.

(2) The crude product (18.5 g, 0.062 mol) obtained in the step (1) was dissolved in 10% HCl—AcOEt solution (65 ml), and stirred for 2.5 h. Then, the solvent was removed by rotary evaporation, and water (50 ml) was added to the residue. The resultant mixture was then washed with ethyl acetate (50 ml). The water phase was basified with 25% NaOH to PH>10, and extracted with ethyl acetate (50 ml*1, 25 ml*2). The organic phase was combined and dried with anhydrous magnesium sulfate, and evaporated to dryness by rotary evaporation, to obtain a crude product, which was directly used in the next step.

(3) The crude product (4.39 g, 0.32 mol) obtained in the step (2), Intermediate 3 (3 g, 0.32 mol), HOBt (2.54 g) and ethyl acetate (30 ml) were mixed, and in an ice-bath, a mixed solution of DCC (3.87 g) and ethyl acetate (10 ml) was added dropwise. The reaction was carried out in an ice-bath for 3 h. The resultant mixture was warmed to room temperature and reacted for 12 h. The resultant solution was filtrated to remove the undissolved substance, and washed with ethyl acetate, then washed with 5% hydrochloric acid, saturated saline solution, saturated sodium bicarbonate, and saturated saline solution sequentially, and dried with anhydrous magnesium sulfate. The organic phase was evaporated to dryness by rotary evaporation, to obtain a crude product. The crude product was recrystallized with absolute ethanol to get Compound 1, as yellow needle-like powder (3.1 g, Yield: 42%)

$^1$H-NMR (400 MHz, DMSO) 0.86 (6H, d) 1.20-1.31 (5H, m) 1.54 (1H, m) 1.79-1.88 (2H, m) 2.03 (3H, s) 2.42 (2H, m) 2.90-3.20 (2H, m) 3.61 (1H, d) 3.72 (1H, d) 4.6-4.17 (2H, m) 4.27-4.28 (1H, m) 8.06-8.09 (1H, t) 8.63 (1H, d) EI-MS (m/z): 361 [M+H]$^+$

Example 2 (2s, 3s)-2-ethoxycarbonyl-3-[2-[(s)-4-methylthio-1-carbonyl-1-(pentylamino) butane]formylamino]epoxysuccinic acid (Compound 2)

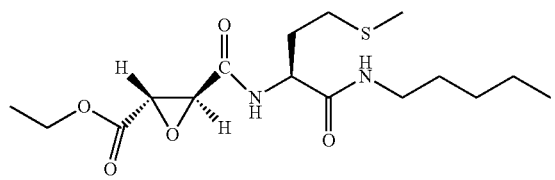

Compound 2 n-Pentylamine and Intermediate 3 were used as raw materials, and operations were performed as they were in Example 1, to get Compound 2, as white needle-like powder.

$^1$H-NMR (400 MHz, DMSO) 0.86 (3H, d) 1.17-1.37 (9H, m) 1.79-1.88 (2H, m) 2.03 (3H, s) 2.42 (2H, m) 2.90-3.20 (2H, m) 3.61 (1H, d) 3.72 (1H, d) 4.16-4.17 (2H, m) 4.27-4.28 (1H, m) 8.06-8.09 (1H, t) 8.63 (1H, d) EI-MS (m/z): 361[M+H]*.

Example 3 (2s, 3s)-2-ethoxycarbonyl-3-[2-[(s)-4-methylthio-1-carbonyl-1-(2-methylbutyl amino)butane]formylamino]epoxysuccinic acid (Compound 3)

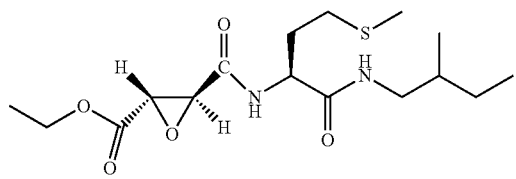

Compound 3

2-Methylbutylamine and Intermediate 3 were used as raw materials, and operations were performed as they were in Example 1, to get Compound 3, as white needle-like powder.

$^1$H-NMR (400 MHz, DMSO) 0.86 (6H, m) 1.21-1.50 (6H, m) 1.79-1.88 (2H, m) 2.03 (3H, s) 2.42 (2H, m) 2.90-3.20 (2H, m) 3.61 (1H, d) 3.72 (1H, d) 4.16-4.17 (2H, m) 4.27-4.28 (1H, m) 8.06-8.09 (1H, t) 8.63 (1H, d) EI-MS (m/z): 361 [M+H]$^+$.

Example 4 (2s, 3s)-2-ethoxycarbonyl-3-[2-[(s)-4-methylthio-1-carbonyl-1-(propylamino) butane]formylamino]epoxysuccinic acid (Compound 4)

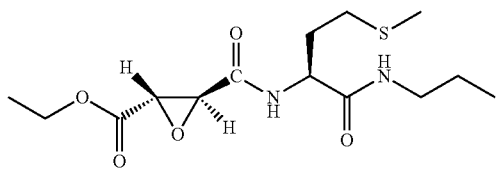

Compound 4

Propylamine and Intermediate 3 were used as raw materials, and operations were performed as they were in Example 1, to get Compound 4, as white needle-like powder.

$^1$H-NMR (400 MHz, DMSO) 0.80 (3H, m) 1.21-1.38 (5H, m) 1.79-1.88 (2H, m) 2.03 (3H, s) 2.42 (2H, m) 2.90-3.20 (2H, m) 3.61 (1H, d) 3.72 (1H, d) 4.16-4.17 (2H, m) 4.27-4.28 (1H, m) 8.06-8.09 (1H, t) 8.63 (1H, d) EI-MS (m/z): 333[M+H]+.

Example 5 (2s, 3s)-2-ethoxycarbonyl-3-[2-[(s)-4-methylthio-1-carbonyl-1-(hexylamino) butane]formylamino]epoxysuccinic acid (Compound 5)

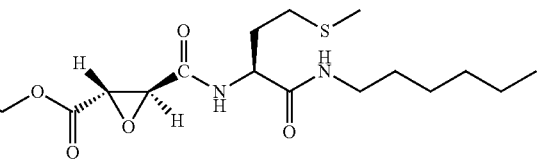

Compound 5

Hexylamine and Intermediate 3 were used as raw materials, and operations were performed as they were in Example 1, to get Compound 5, as white needle-like powder.

$^1$H-NMR (400 MHz, DMSO) 0.86 (3H, t) 1.17-1.35 (11H, m) 1.79-1.88 (2H, m) 2.03 (3H, s) 2.42 (2H, m) 2.90-3.20 (2H, m) 3.61 (1H, d) 3.72 (1H, d) 4.16-4.17 (2H, m) 4.27-4.28 (1H, m) 8.06-8.09 (1H, t) 8.63 (1H, d) EI-MS (m/z): 375[M+H]$^+$.

Example 6 (2s, 3s)-2-ethoxycarbonyl-3-[2-[(s)-4-methylthio-1-carbonyl-1-(1-methylbutyl amino)butane]formylamino]epoxysuccinic acid (Compound 6)

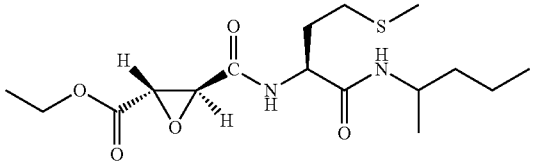

Compound 6

2-Aminopentane and Intermediate 3 were used as raw materials, and operations were performed as they were in Example 1, to get Compound 6, as white needle-like powder.

¹H-NMR (400 MHz, DMSO) 0.86 (3H, t) 1.01 (3H, t) 1.21-1.50 (7H, m) 1.79-1.88 (2H, m) 2.03 (3H, s) 2.42 (2H, m) 3.61 (1H, d) 3.72 (1H, d) 4.16-4.17 (2H, m) 4.27-4.28 (1H, m) 8.06-8.09 (1H, t) 8.63 (1H, d) EI-MS (m/z): 361 [M+H]⁺.

Example 7 (2s, 3s)-2-ethoxycarbonyl-3-[2-[(s)-4-methylthio-1-carbonyl-1-(3-methyl piperidinyl)butane]formylamino]epoxysuccinic acid (Compound 7)

Compound 7

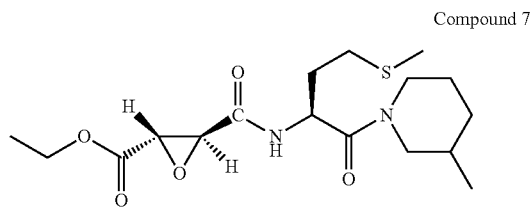 [SMILES: CCOC(=O)[C@H]1O[C@@H]1C(=O)N[C@@H](CCSC)C(=O)N1CCCC(C)C1]

3-Methylpiperidine and Intermediate 3 were used as raw materials, and operations were performed as they were in Example 1, to get Compound 7, as white solid.
¹H-NMR (400 MHz, DMSO) 0.8 (3H, d) 1.21 (3H, t) 1.41-1.97 (7H, m) 2.03 (3H, s) 2.42 (2H, m) 3.50-3.60 (5H, m) 3.72 (1H, d) 4.16-4.17 (2H, m) 4.27-4.28 (1H, m) 8.71 (1H, d) EI-MS (m/z): 373 [M+H]⁺.

Example 8 (2s, 3s)-2-ethoxycarbonyl-3-[2-[(s)-4-methylthio-1-carbonyl-1-(3-phenyl propylamino)butane]formylamino]epoxysuccinic acid (Compound 8)

Compound 8

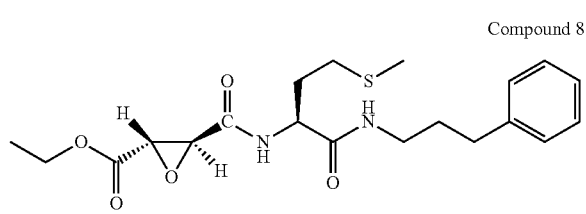 [SMILES: CCOC(=O)[C@H]1O[C@@H]1C(=O)N[C@@H](CCSC)C(=O)NCCCc1ccccc1]

3-Phenylpropylamine and Intermediate 3 were used as raw materials, and operations were performed as they were in Example 1, to get Compound 8, as yellow needle-like powder.
¹H-NMR (400 MHz, DMSO) 1.21-1.3 (5H, m) 1.50-1.88 (4H, m) 2.03 (3H, s) 2.42 (2H, m) 3.00-3.10 (2H, m) 3.61 (1H, d) 3.72 (1H, d) 4.16-4.17 (2H, m) 4.33-4.37 (1H, m) 7.17-7.27 (5H, m) 8.13 (1H, t) 8.63 (1H, d) EI-MS (m/z): 409[M+H]⁺.

Example 9 (2s, 3s)-2-ethoxycarbonyl-3-[2-[(s)-4-methylthio-1-carbonyl-1-(isobutylamino) butane]formylamino]epoxysuccinic acid (Compound 9)

Compound 9

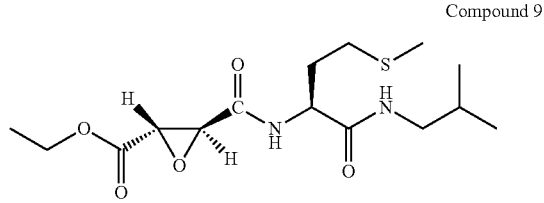 [SMILES: CCOC(=O)[C@H]1O[C@@H]1C(=O)N[C@@H](CCSC)C(=O)NCC(C)C]

Isobutylamine and Intermediate 3 were used as raw materials, and operations were performed as they were in Example 1, to get Compound 9, as white needle-like powder.
¹H-NMR (400 MHz, DMSO) 0.80 (6H, d) 1.21-1.43 (4H, m) 1.79-1.88 (2H, m) 2.03 (3H, s) 2.42 (2H, m) 2.90-3.20 (2H, m) 3.55 (1H, m) 3.72 (1H, d) 4.16-4.17 (2H, m) 4.27-4.28 (1H, m) 8.06-8.09 (1H, t) 8.63 (1H, d) EI-MS (m/z): 347[M+H]⁺

Example 10 (2s, 3s)-2-ethoxycarbonyl-3-[2-[(s)-4-methylthio-1-carbonyl-1-(4-methoxy phenylethylamino)butane]formylamino]epoxysuccinic acid (Compound 10)

Compound 10

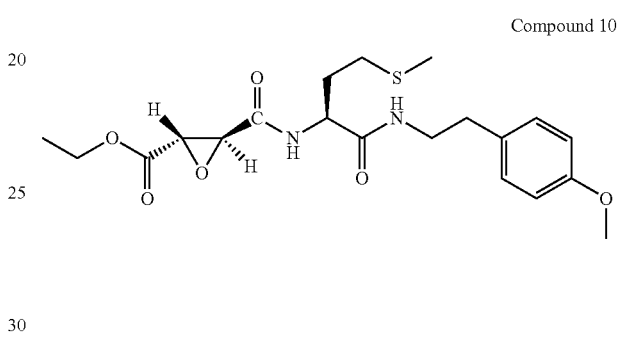

4-Methoxyphenylethylamine and Intermediate 3 were used as raw materials, and operations were performed as they were in Example 1, to get Compound 10, as white needle-like powder.
¹H-NMR (400 MHz, DMSO) 1.21-1.3 (3H, t) 1.79-1.88 (4H, m) 2.03 (3H, s) 2.42 (2H, m) 3.00-3.10 (2H, m) 3.61 (1H, d) 3.72 (1H, d) 3.74 (3H, s) 4.16-4.17 (2H, m) 4.27-4.28 (1H, m) 7.05-7.15 (4H, m) 8.06-8.09 (1H, t) 8.63 (1H, d) EI-MS (m/z): 325[M+H]⁺

Example 11 (2s, 3s)-2-ethoxycarbonyl-3-[2-[(s)-4-methylthio-1-carbonyl-1-(tetrahydropyrrolyl)butane]formylamino]epoxysuccinic acid (Compound 11)

Compound 11

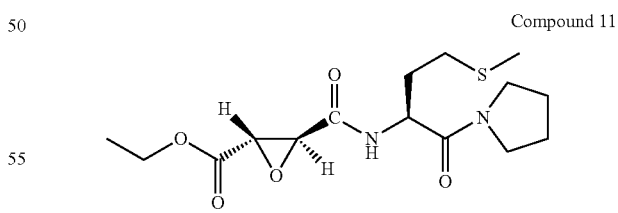

Tetrahydropyrrole and Intermediate 3 were used as raw materials, and operations were performed as they were in Example 1, to get Compound 11, as white needle-like powder.
¹H-NMR (400 MHz, DMSO) 1.21 (3H, t) 1.79-1.99 (6H, m) 2.03 (3H, s) 2.42 (2H, m) 3.41-3.50 (4H, m) 3.55 (1H, m) 3.72 (1H, d) 4.16-4.17 (2H, m) 4.27-4.28 (1H, m) 8.63 (1H, d) EI-MS (m/z): 345[M+H]⁺

Example 12 (2s, 3s)-2-ethoxycarbonyl-3-[2-[(s)-4-methylthio-1-carbonyl-1-(morpholinyl) butane]formylamino]epoxysuccinic id (Compound 12)

Compound 12

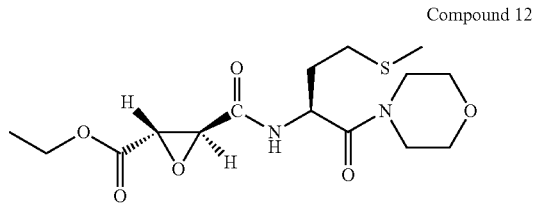 [SMILES: CCOC(=O)[C@H]1O[C@@H]1C(=O)N[C@@H](CCSC)C(=O)N1CCOCC1]

Morpholine and Intermediate 3 were used as raw materials, and operations were performed as they were in Example 1, to get Compound 12, as colorless needle-like powder.

¹H-NMR (400 MHz, DMSO) 1.21 (31H, t) 1.79-1.99 (2H, m) 2.03 (3H, s) 2.42 (2H, m) 3.40-3.57 (8H, m) 3.60 (1H, m) 3.72 (1H, d) 4.16-4.17 (2H, m) 4.27-4.28 (1H, m) 8.76 (1H, d) EI-MS (m/z): 361 [M+H]⁺

Example 13 (2s, 3s)-2-ethoxycarbonyl-3-[2-[(s)-4-methylthio-1-carbonyl-1-(phenyl piperidinyl)butane]formylamino]epoxysuccinic acid (Compound 13)

Compound 13

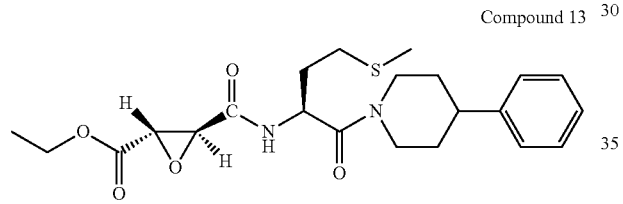

4-Phenylpiperidine and Intermediate 3 were used as raw materials, and operations were performed as they were in Example 1, to get Compound 13, as colorless needle-like powder.

¹H-NMR (400 MHz, DMSO) 1.21 (3H, t) 1.50-1.90 (6H, m) 2.03 (3H, s) 2.42 (2H, m) 2.65 (1H, t) 2.75 (2H, t) 3.15 (2H, t) 3.60 (1H, m) 3.72 (1H, d) 4.12-4.15 (2H, m) 4.41-4.51 (1H, m) 7.10-7.38 (5H, m) 8.81 (1H, d) EI-MS (m/z): 435[M+H]⁺.

Example 14 (2s, 3s)-2-ethoxycarbonyl-3-[2-[(s)-4-methylthio-1-carbonyl-1-(neopentylamino)butane]formylamino]epoxysuccinic acid (Compound 30)

Compound 30

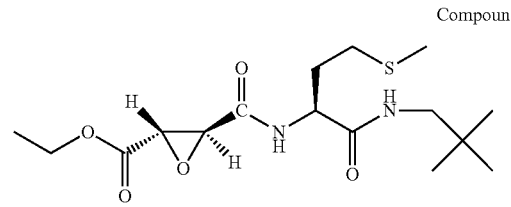

Neopentylamine and Intermediate 3 were used as raw materials, and operations were performed as they were in Example 1, to get Compound 30, as yellow needle-like powder.

¹H-NMR (400 MHz, DMSO) 0.86 (9H, s) 1.22 (3H, t) 1.80-1.88 (2H, m) 2.03 (3H, s) 2.42 (2H, m) 2.90-3.20 (2H, m) 3.61 (1H, d) 3.72 (1H, d) 4.16-4.17 (2H, m) 4.27-4.28 (1H, m) 8.06-8.09 (1H, t) 8.63 (1H, d) EI-MS (m/z): 361 [M+H]⁺.

Example 15 (2s, 3s)-2-ethoxycarbonyl-3-[2-[(s)-4-methylthio-1-carbonyl-1-(tert-pentyl amino)butane]formylamino]epoxysuccinic acid (Compound 31)

Compound 31

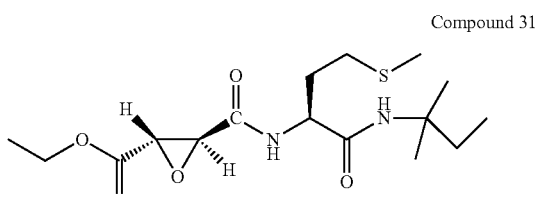

Tert-pentylamine and Intermediate 3 were used as raw materials, and operations were performed as they were in Example 1, to get Compound 31, as white needle-like powder.

¹H-NMR (400 MHz, DMSO) 0.86 (9H, t) 1.15-1.30 (6H, t) 1.50-1.88 (4H, m) 2.03 (3H, s) 2.42 (2H, m) 3.61 (1H, d) 3.72 (1H, d) 4.16-4.17 (2H, m) 4.27-4.28 (1H, m) 7.51 (1H, s) 8.51 (1H, d) EI-MS (m/z): 361 [M+H]⁺.

Example 16 (2s, 3s)-2-ethoxycarbonyl-3-[2-[(s)-4-methylthio-1-carbonyl-1-(tert-butyl amino)butane]formylamino]epoxysuccinic acid (Compound 32)

Compound 32

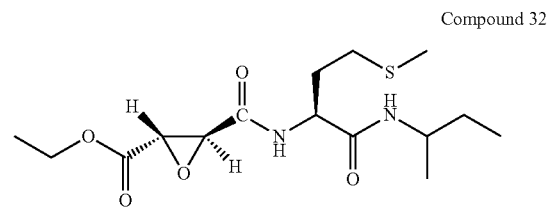 [SMILES: CCOC(=O)[C@H]1O[C@@H]1C(=O)N[C@@H](CCSC)C(=O)NC(C)CC]

2-Butylamine and Intermediate 3 were used as materials, and operations were performed as they were in Example 1, to get Compound 32, as yellow needle-like powder.

¹H-NMR (400 MHz, DMSO) 0.86 (3H, t) 1.05 (3H, d) 1.15-1.35 (5H, m) 1.80-1.88 (2H, m) 2.03 (3H, s) 2.42 (2H, m) 3.61 (1H, d) 3.72 (1H, d) 4.16-4.17 (2H, m) 4.27-4.28 (1H, m) 7.99 (1H, d) 8.66 (1H, d) EI-MS (m/z): 347[M+H]⁺.

Example 17 (2s, 3s)-2-ethoxycarbonyl-3-[2-[(s)-4-methylthio-1-carbonyl-1-(p-methyl phenylethylamino)butane]formylamino]epoxysuccinic acid (Compound 33)

Compound 33

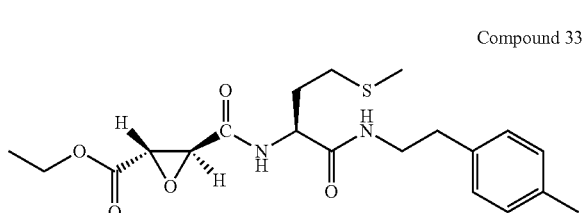

p-Methylphenylethylamine and Intermediate 3 were used as raw materials, and operations were performed as they were in Example 1, to get Compound 33, as yellow solid.

$^1$H-NMR (400 MHz, DMSO) 1.21-1.3 (3H, t) 1.79-1.88 (2H, m) 2.03 (3H, s) 2.29 (3H, s) 2.42 (2H, m) 3.00-3.10 (2H, m) 3.61-3.72 (4H, m) 4.16-4.17 (2H, m) 4.27-4.28 (1H, m)) 7.05-7.10 (4H, m) 8.06-8.09 (1H, t) 8.63 (1H, d) EI-MS (m/z): 409 [M+H]$^+$.

Example 18 (2s, 3s)-2-ethoxycarbonyl-3-[2-[(s)-4-methylthio-1-carbonyl-1-(3-fluoro phenylethylamino)butane]formylamino]epoxysuccinic acid (Compound 34)

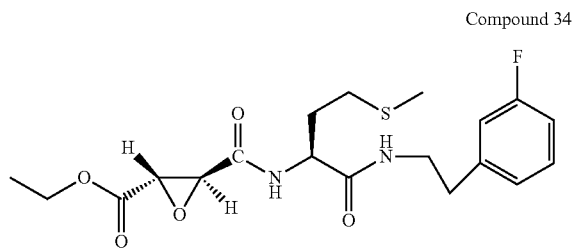 [SMILES: CCOC(=O)[C@H]1O[C@@H]1C(=O)N[C@@H](CCSC)C(=O)NCCc1cccc(F)c1]

Compound 34

3-Fluorophenylethylamine and Intermediate 3 were used as raw materials, and operations were performed as they were in Example 1, to get Compound 34, as yellow solid.

$^1$H-NMR (400 MHz, DMSO) 1.21-1.3 (3H, t) 1.79-1.88 (2H, m) 2.03 (3H, s) 2.42 (2H, m) 2.70-2.75 (2H, m) 3.61-3.72 (4H, m) 4.16-4.17 (2H, m) 4.28-4.32 (1H, m) 7.05 (3H, m) 7.30 (1H, m) 8.17 (1H, t) 8.63 (1H, d) EI-MS (m/z): 413[M+H]$^+$.

Example 19 (2s, 3s)-2-ethoxycarbonyl-3-[2-[(s)-4-methylthio-1-carbonyl-1-(2-ethyl piperidinyl)butane]formylamino]epoxysuccinic acid (Compound 35)

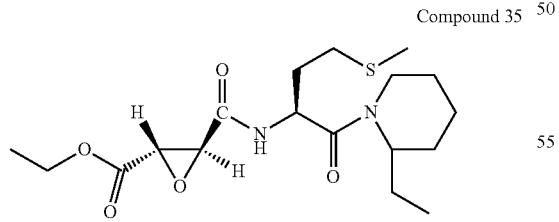

Compound 35

2-Ethylpiperidine and Intermediate 3 were used as raw materials, and operations were performed as they were in Example 1, to get Compound 35, as colorless solid.

$^1$H-NMR (400 MHz, DMSO) 1.21 (3H, t) 1.41-1.97 (1 OH, m) 2.03 (3H, s) 2.42 (2H, m) 3.50-3.60 (4H, m) 3.72 (1H, d) 4.16-4.17 (2H, m) 4.41-4.51 (1H, m) 8.71 (1H, d) EI-MS (m/z): 387[M+H]$^+$.

Example 20 (2s, 3s)-2-ethoxycarbonyl-3-[2-[(s)-4-methylthio-1-carbonyl-1-(thiomorpholinyl)butane]formylamino]epoxysuccinic acid (Compound 36)

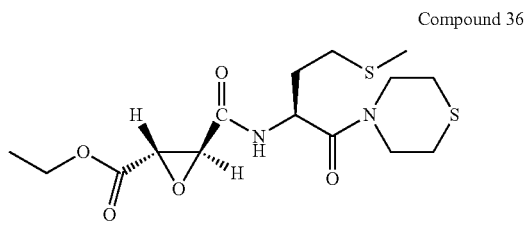 [SMILES: CCOC(=O)[C@H]1O[C@@H]1C(=O)N[C@@H](CCSC)C(=O)N1CCSCC1]

Compound 36

Thiomorpholine and Intermediate 3 were used as raw materials, and operations were performed as they were in Example 1, to get Compound 36, as white solid.

$^1$H-NMR (400 MHz, DMSO) 1.21 (3H, t) 1.79-1.99 (2H, m) 2.03 (3H, s) 2.42-2.65 (6H, m) 3.60 (1H, m) 3.72 (1H, d) 3.9 (4H. t) 4.16-4.17 (2H, m) 4.27-4.28 (1H, m) 8.81 (1H, d) EI-MS (m/z): 377[M+H]$^+$.

Example 21 (2s, 3s)-2-ethoxycarbonyl-3-[2-[(s)-4-methylthio-1-carbonyl-1-(tetrahydrothiazolyl)butane]formylamino]epoxysuccinic acid (Compound 38)

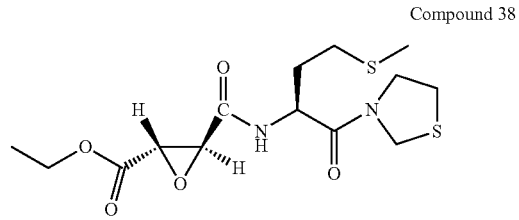 [SMILES: CCOC(=O)[C@H]1O[C@@H]1C(=O)N[C@@H](CCSC)C(=O)N1CCSC1]

Compound 38

Tetrahydrothiazole and Intermediate 3 were used as raw materials, and operations were performed as they were in Example 1, to get Compound 38, as white solid.

$^1$H-NMR (400 MHz, DMSO) 1.21 (3H, t) 1.79-1.99 (2H, m) 2.03 (3H, s) 2.42 (2H, m) 3.03 (2H, m) 3.60 (1H, m) 3.72 (1H, d) 3.89 (2H, m) 4.16-4.17 (2H, m) 4.27-4.28 (1H, m) 4.44 (2H, dd) 8.87 (1H, d) EI-MS (m/z): 363[M+H]$^+$.

Example 22 (2s, 3s)-2-ethoxycarbonyl-3-[2-[(s)-4-methylthio-1-carbonyl-1-(1-ethyl propylamino)butane]formylamino]epoxysuccinic acid (Compound 39)

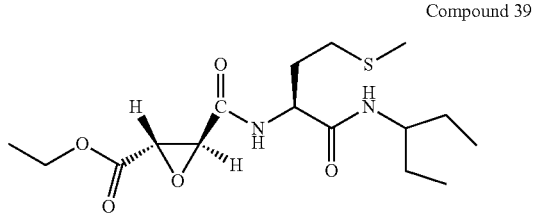 [SMILES: CCOC(=O)[C@H]1O[C@@H]1C(=O)N[C@@H](CCSC)C(=O)NC(CC)CC]

Compound 39

3-Aminopentane and Intermediate 3 were used as raw materials, and operations were performed as they were in Example 1, to get Compound 39, as white needle-like powder.

1H-NMR (400 MHz, DMSO) 0.86 (6H, t) 1.21-1.43 (7H, m) 1.79-1.88 (2H, m) 2.03 (3H, s) 2.42 (2H, m) 3.49-3.52 (1H, m) 3.59 (1H, m) 3.72 (1H, d) 4.16-4.17 (2H, m) 4.27-4.28 (1H, m) 7.77 (1H, t) 8.63 (1H, d) EI-MS (m/z): 361 [M+H]$^+$.

Example 23 (2s, 3s)-2-ethoxycarbonyl-3-[2-[(s)-4-methylthio-1-carbonyl-1-(4-phenyl butylamino)butane]formylamino]epoxysuccinic acid (Compound 4

Compound 40

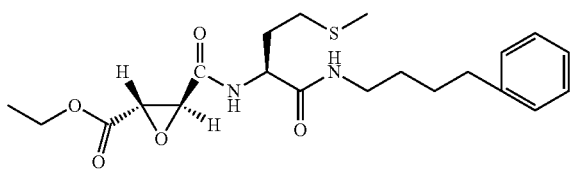

4-Phenylbutylamine and Intermediate 3 were used as raw materials, and operations were performed as they were in Example 1, to get Compound 40, as white solid.

$^1$H-NMR (400 MHz, DMSO) 1.21-1.3 (3H, m) 1.35-1.51 (4H, m) 1.79-1.88 (2H, m) 2.03 (3H, s) 2.42 (2H, m) 2.53 (2H, t) 3.00-3.10 (2H, m) 3.57 (1H, d) 3.67 (1H, d) 4.16-4.17 (2H, m) 4.27-4.28 (1H, m) 7.17-7.27 (5H, m) 8.06-8.09 (1H, t) 8.63 (1H, d) EI-MS (m/z): 423[M+H]$^+$.

Example 24 (2s, 3s)-2-ethoxycarbonyl-3-[2-[(s)-4-methylthio-1-carbonyl-1-(3,5-dimethyl piperidinyl) butane]formylamino]epoxysuccinic acid (Compound 41)

Compound 41

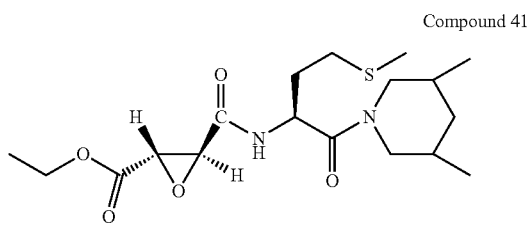 [SMILES: CCOC(=O)[C@H]1O[C@@H]1C(=O)N[C@@H](CCSC)C(=O)N1CC(C)CC(C)C1]

3,5-Dimethylpiperidine and Intermediate 3 were used as raw materials, and operations were performed as they were in Example 1, to get Compound 41, as colorless solid.

1H-NMR (400 MHz, DMSO) 0.80 (6H, m) 1.21 (3H, t) 1.41-1.97 (6H, m) 2.03 (3H, s) 2.42 (2H, m) 3.50-3.60 (5H, m) 3.72 (1H, d) 4.16-4.17 (2H, m) 4.27-4.28 (1H, m) 8.71 (1H, d) EI-MS (m/z): 387[M+H]$^+$

Example 25 (2s, 3s)-2-ethoxycarbonyl-3-[2-[(s)-3-benzylthio-1-carbonyl-1-(2-methylbutylamino)propane]formylamino]epoxysuccinic acid (Compound 14)

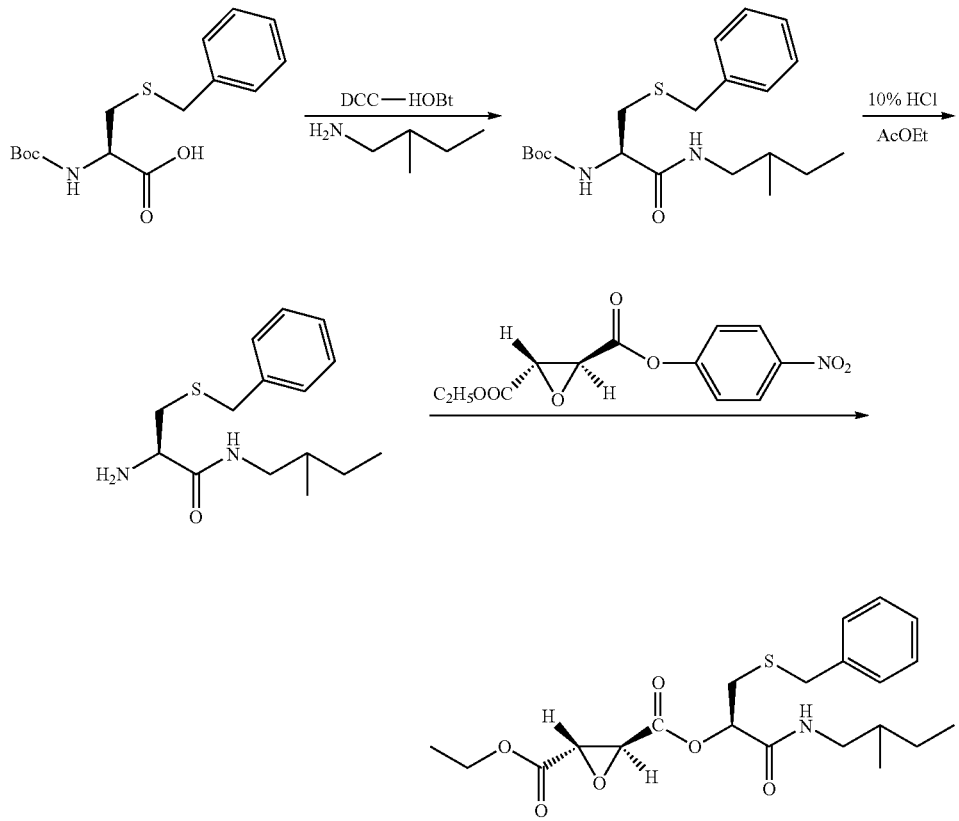

(1) DCC (10.32 g, 0.05 mol) was dissolved in ethyl acetate (20 ml), to form an ethyl acetate solution of DCC. N-(tert-butoxycarbonyl)-S-benzyl-L-cysteine (15.47 g, 0.05 mol), 2-methylbutylamine (3.21 g, 0.05 mol) and HOBt (6.76 g, 0.05 mol) were dissolved in ethyl acetate (35 ml), and stirred in an ice-bath at 3-8° C., the ethyl acetate solution of DCC prepared was then added dropwise. The resultant mixture was stirred at 3-8° C. for 1.5 h, warmed to room temperature and reacted for 2.5 h. After the reaction was finished, and the impurities were filtrated off, and the precipitate was washed with ethyl acetate (40 ml). The filtrates were combined, and washed with 5% hydrochloric acid (100 ml), saturated saline solution (100 ml), saturated sodium bicarbonate (100 ml), and saturated saline water (100 ml) sequentially. The organic phase was dried with anhydrous magnesium sulfate, and evaporated to dryness by rotary evaporation to obtain a crude product (14.85 g), which was directly used in the next step without purification.

(2) The crude product obtained in the step (1) was dissolved in 10% HCl—AcOEt solution (65 ml), and stirred for 2.5 h. The solvent was removed by rotary evaporation, and water (50 ml) was added to the residue. The resultant solution was washed with ethyl acetate (50 ml), and the water phase was basified with 25% NaOH to PH>10, and extracted with ethyl acetate. The organic phases were combined and dried with anhydrous magnesium sulfate, and then evaporated to dryness by rotary evaporation to obtain a crude product, which was directly used in the next step.

(3) Intermediate 4 (10 g, 0.035 mol) was dissolved in ethyl acetate (100 ml) was stirred at room temperature to form a solution. The product (9.3 g, 0.035 mol) obtained in the step (2) was dissolved in ethyl acetate (13 ml), then slowly added dropwise to the solution. The resultant mixture was stirred at room temperature for 4 h. After the reaction was finished, the resultant mixture was filtrated. The filtrate was washed with 2% saturated NaOH (30 ml*2), saturated saline solution (40 ml), 5% hydrochloric acid (40 ml) and saturated saline solution (40 ml*4) sequentially, dried with anhydrous magnesium sulfate, and evaporated to dryness by rotary evaporation, to obtain a crude product. The crude product was purified by column chromatography using a silica gel column, to obtain the compound as colorless oil (11.2 g, yield: 58%).

$^1$H-NMR (400 MHz, DMSO) 0.86 (6H, m) 1.21-1.50 (6H, m) 2.50-2.71 (2H, m) 2.90-3.20 (2H, m) 3.61-3.72 (3H, m) 4.16 (2H, m) 4.56 (1H, q) 7.10-7.30 (5H, m) 8.06-8.09 (1H, t) 8.63 (1H, d) EI-MS (m/z): 423 [M+H]$^+$.

Example 26 (2s, 3s)-2-ethoxycarbonyl-3-[2-[(s)-3-benzylthio-1-carbonyl-1-(neopentyl amino)propane]formylamino]epoxysuccinic acid (Compound 15)

Compound 15

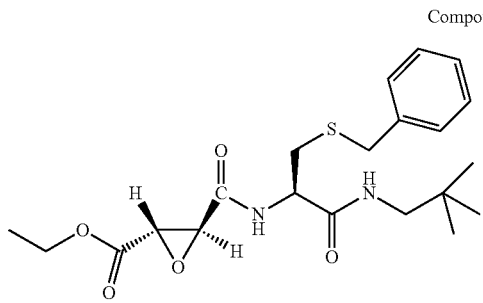

Neopentylamine and Intermediate 4 were used as raw materials, and operations were performed as they were in Example 25, to get Compound 15, as yellow oil.

$^1$H-NMR (400 MHz, DMSO) 0.86 (9H, s) 1.22 (3H, t) 2.50-2.71 (2H, m) 2.90-3.20 (2H, m) 3.61-3.72 (3H, m) 4.16 (2H, m) 4.56 (1H, q) 7.10-7.30 (5H, m) 8.06-8.09 (1H, t) 8.63 (1H, d) EI-MS (m/z): 423 [M+H]$^+$.

Example 27 (2s, 3s)-2-ethoxycarbonyl-3-[2-[(s)-3-benzylthio-1-carbonyl-1-(tert-pentyl amino)propane]formylamino]epoxysuccinic acid (Compound 16)

Compound 16

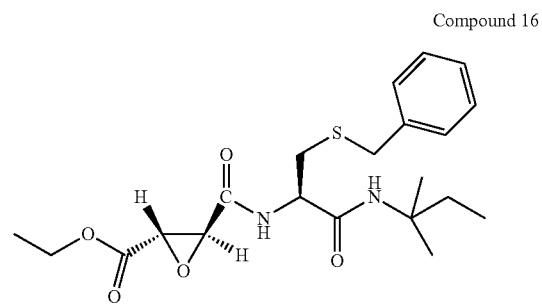 [SMILES: CCOC(=O)[C@H]1O[C@@H]1C(=O)N[C@@H](CSCc1ccccc1)C(=O)NC(C)(C)CC]

Tert-pentylamine and Intermediate 4 were used as raw materials, and operations were performed as they were in Example 25, to get Compound 16, as yellow oil.

$^1$H-NMR (400 MHz, DMSO) 0.86 (9H, t) 1.15-1.30 (6H, t) 1.50-1.88 (2H, m) 2.50-2.71 (2H, m) 3.61-3.72 (3H, m) 4.16-4.34 (2H, m) 4.56 (1H, q) 7.10-7.30 (5H, m) 7.51 (1H, s) 8.51 (1H, d) EI-MS (m/z): 423 [M+H]$^+$.

Example 28 (2s, 3s)-2-ethoxycarbonyl-3-[2-[(s)-3-benzylthio-1-carbonyl-1-(propylamino) propane]formylamino]epoxysuccinic acid (Compound 17)

Compound 17

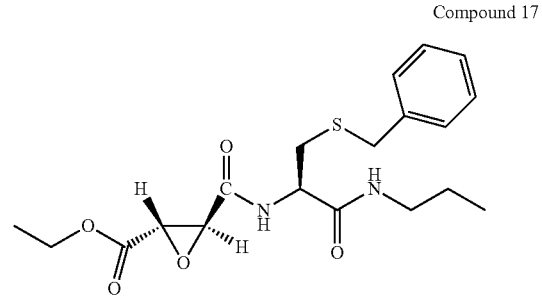 [SMILES: CCCNC(=O)[C@H](CSCc1ccccc1)NC(=O)[C@H]1O[C@@H]1C(=O)OCC]

Propylamine and Intermediate 4 were used as raw materials, and operations were performed as they were in Example 25, to get Compound 17, as colorless oil.

$^1$H-NMR (400 MHz, DMSO) 0.80 (3H, m) 1.21-1.38 (5H, m) 2.50-2.71 (2H, m) 2.90-3.20 (2H, m) 3.61-3.72 (4H, m) 4.16-4.34 (2H, m) 4.56 (1H, q) 7.10-7.31 (5H, m) 8.06-8.09 (1H, t) 8.63 (1H, d) EI-MS (m/z): 395[M+H]$^+$.

Example 29 (2s, 3s)-2-ethoxycarbonyl-3-[2-[(s)-3-benzylthio-1-carbonyl-1-(hexylamino) propane]formylamino]epoxysuccinic acid (Compound 18)

Compound 18

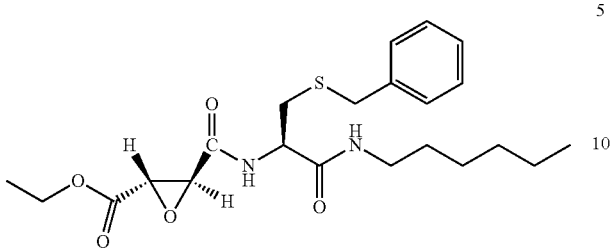

Hexylamine and Intermediate 4 were used as raw materials, and operations were performed as they were in Example 25, to get Compound 18, as yellow solid.

$^1$H-NMR (400 MHz, DMSO) 0.86 (3H, t) 0.17-1.35 (11H, m) 2.71 (2H, m) 2.90-3.20 (2H, m) 3.61-3.72 (4H, m) 4.16-4.34 (2H, m) 4.56 (1H, q) 7.10-7.31 (5H, m) 8.06-8.09 (1H, t) 8.63 (1H, d) EI-MS (m/z): 437[M+H]$^+$.

Example 30 (2s, 3s)-2-ethoxycarbonyl-3-[2-[(s)-3-benzylthio-1-carbonyl-1-(1-methyl propylamino) propane]formylamino]epoxysuccinic acid (Compound 19)

Compound 19

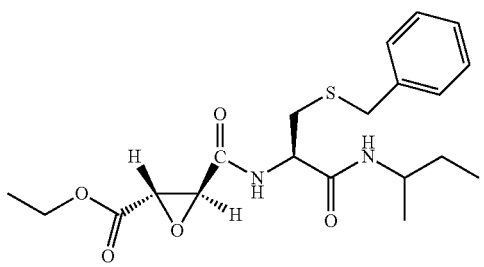

2-Butylamine and Intermediate 4 were used as raw materials, and operations were performed as they were in Example 25, to get Compound 19, as white solid.

$^1$H-NMR (400 MHz, DMSO) 0.86 (3H, t) 1.05 (3H, d) 1.15-1.35 (5H, m) 2.50-2.71 (2H, m) 3.61-3.72 (4H, m) 4.16-4.34 (3H, m) 4.56 (1H, q) 7.10-7.31 (5H, m) 7.99 (1H, d) 8.66 (1H, d) EI-MS (m/z): 409[M+H]$^+$.

Example 31 (2s, 3s)-2-ethoxycarbonyl-3-[2-[(s)-3-benzylthio-1-carbonyl-1-(4-phenyl butylamino)propane]formylamino]epoxysuccinic acid (Compound 20)

Compound 20

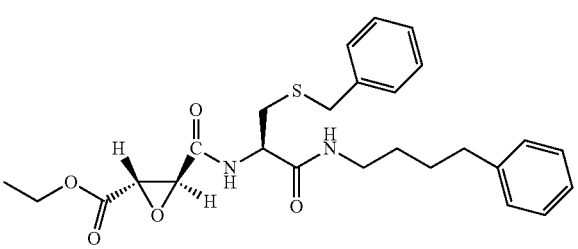

4-Phenylbutylamine and Intermediate 4 were used as raw materials, and operations were performed as they were in Example 25, to get Compound 20, as colorless solid.

$^1$H-NMR (400 MHz, DMSO) 1.21-1.3 (5H, m) 1.35-1.88 (4H, m) 2.50-2.71 (2H, m) 3.00-3.10 (2H, m) 3.61-3.72 (4H, m) 4.16-4.34 (2H, m) 4.56 (1H, q) 7.17-7.27 (1 OH, m) 8.06-8.09 (1H, t) 8.63 (1H, d) EI-MS (m/z): 485[M+H]$^+$.

Example 32 (2s, 3s)-2-ethoxycarbonyl-3-[2-[(s)-3-benzylthio-1-carbonyl-1-(p-methyl phenylethylamino)propane]formylamino]epoxysuccinic acid (Compound 21)

Compound 21

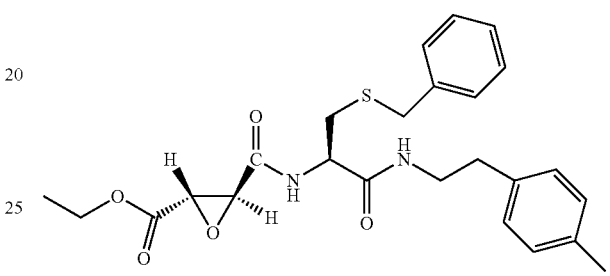

p-Methylphenylethylamine and Intermediate 4 were used as raw materials, and operations were performed as they were in Example 25, to get Compound 21, as yellow solid.

$^1$H-NMR (400 MHz, DMSO) 1.21-1.3 (3H, t) 2.29 (3H, s) 2.50-2.71 (2H, m) 3.00-3.10 (2H, m) 3.61-3.72 (4H, m) 4.16-4.34 (2H, m) 4.56 (1H, q) 7.05-7.30 (9H, m) 8.06-8.09 (1H, t) 8.63 (1H, d) EI-MS (m/z): 471 [M+H]$^+$.

Example 33 (2s, 3s)-2-ethoxycarbonyl-3-[2-[(s)-3-benzylthio-1-carbonyl-1-(tetrahydropyrrolyl)propane]formylamino]epoxysuccinic acid (Compound 22)

Compound 22

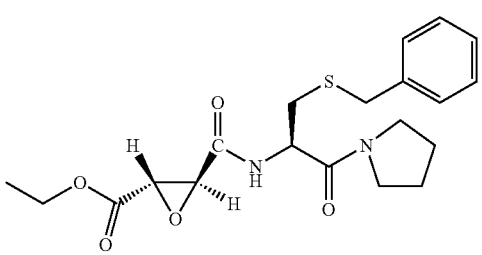

Tetrahydropyrrole and Intermediate 4 were used as raw materials, and operations were performed as they were in Example 25, to get Compound 22, as yellow oil.

$^1$H-NMR (400 MHz, DMSO) 1.21 (3H, t) 1.79-1.99 (4H, m) 2.50-2.71 (2H, m) 3.41-3.50 (4H, m) 3.55 (1H, m) 3.60-3.72 (3H, m) 4.16-4.34 (2H, m) 4.56 (1H, q) 7.10-7.30 (5H, m) 8.63 (1H, d) EI-MS (m/z): 407[M+H]$^+$.

Example 34 (2s, 3s)-2-ethoxycarbonyl-3-[2-[(s)-3-benzylthio-1-carbonyl-1-(4-phenyl piperidinyl)propane]formylamino]epoxysuccinic acid (Compound 23)

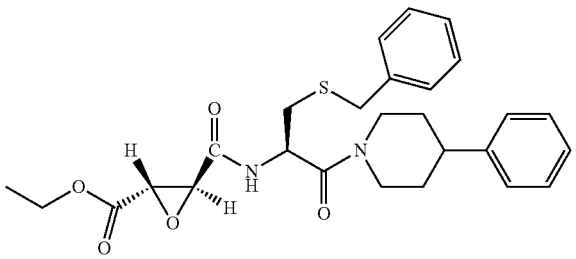
Compound 23

4-Phenylpiperidine and Intermediate 4 were used as raw materials, and operations were performed as they were in Example 25, to get Compound 23, as colorless oil.
$^1$H-NMR (400 MHz, DMSO) 1.17 (3H, t) 1.50-1.90 (4H, m) 2.55-2.75 (5H, m) 3.15 (2H, t) 3.60-3.72 (4H, m) 4.03-4.18 (2H, m) 4.56 (1H, q) 7.10-7.38 (1 OH, m) 8.81 (1H, d) EI-MS (m/z): 473 [M+H]$^+$.

Example 35 (2s, 3s)-2-ethoxycarbonyl-3-[2-[(s)-3-benzylthio-1-carbonyl-1-(3-fluoro phenylethylamino)propane]formylamino]epoxysuccinic acid (Compound 24)

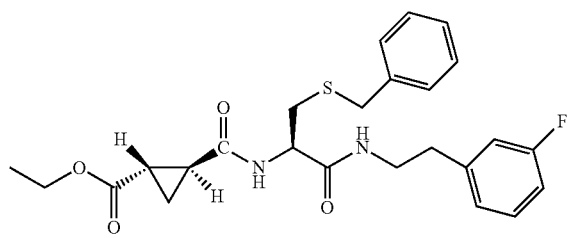
Compound 24

3-Fluorophenylethylamine and Intermediate 4 were used as raw materials, and operations were performed as they were in Example 25, to get Compound 24, as yellow oil.
$^1$H-NMR (400 MHz, DMSO) 1.21-1.3 (3H, t) 2.50-2.75 (4H, m) 3.61-3.72 (6H, m) 4.16-4.34 (2H, m) 4.56 (1H, q) 7.05 (3H, m) 7.10-7.30 (6H, m) 8.17 (1H, t) 8.63 (1H, d) EI-MS (m/z): 475[M+H]$^+$.

Example 36 (2s, 3s)-2-ethoxycarbonyl-3-[2-[(s)-3-benzylthio-1-carbonyl-1-(morpholinyl) propane]formylamino]epoxysuccinic acid (Compound 25)

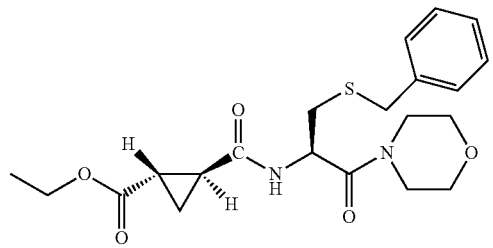
Compound 25

Morpholine and Intermediate 4 were used as raw materials, and operations were performed as they were in Example 25, to get Compound 25, as white solid.
$^1$H-NMR (400 MHz, DMSO) 1.21 (3H, t) 2.50-2.71 (2H, m) 3.40-3.57 (8H, m) 3.60-3.72 (4H, m) 4.16-4.34 (2H, m) 4.56 (1H, q) 7.10-7.30 (5H, m) 8.76 (1H, d) EI-MS (m/z): 423[M+H]$^+$.

Example 37 (2s, 3s)-2-ethoxycarbonyl-3-[2-[(s)-3-benzylthio-1-carbonyl-1-(4-methoxy phenylethylamino)propane]formylamino]epoxysuccinic acid (Compound 26)

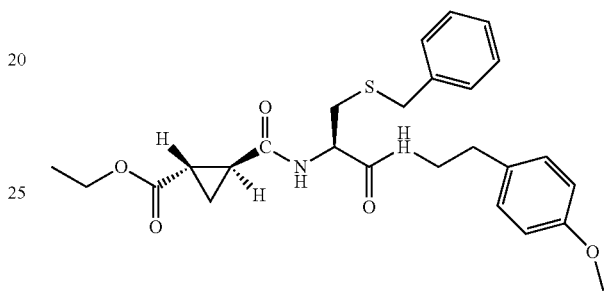
Compound 26

4-Methoxyphenylethylamine and Intermediate 4 were used as raw materials, and operations were performed as they were in Example 25, to get Compound 26, as white powder.
$^1$H-NMR (400 MHz, DMSO) 1.21-1.3 (3H, t) 1.79-1.88 (2H, m) 2.50-2.71 (2H, m) 3.00-3.10 (2H, m) 3.6-3.72 (4H, m) 3.74 (3H, s) 4.16-4.34 (2H, m) 4.56 (1H, q) 7.05-7.30 (9H, m) 8.06-8.09 (1H, t) 8.63 (1H, d) EI-MS (m/z): 487[M+H]$^+$.

Example 38 (2s, 3s)-2-ethoxycarbonyl-3-[2-[(s)-3-benzylthio-1-carbonyl-1-(1-methyl butylamino)propane]formylamino]epoxysuccinic acid (Compound 42)

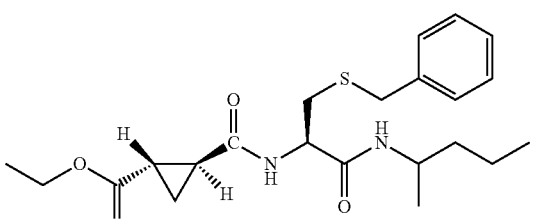
Compound 42

2-Aminopentane and Intermediate 4 we used as raw arials, and operations were performed as they were in Example 25, to get Compound 42, as white solid.
$^1$H-NMR (400 MHz, DMSO) 0.86 (3H, t) 1.01 (3H, t) 1.21-1.50 (7H, m) 2.50-2.71 (2H, m) 3.61-3.72 (4H, m) 4.00-4.34 (3H, m) 4.56 (1H, q) 7.10-7.30 (5H, m) 8.06-8.09 (1H, t) 8.63 (1H, d) EI-MS (m/z): 423 [M+H]$^+$.

Example 39 (2s, 3s)-2-ethoxycarbonyl-3-[2-[(s)-3-benzylthio-1-carbonyl-1-(1-ethyl propylamino)propane]formylamino]epoxysuccinic acid (Compound 43)

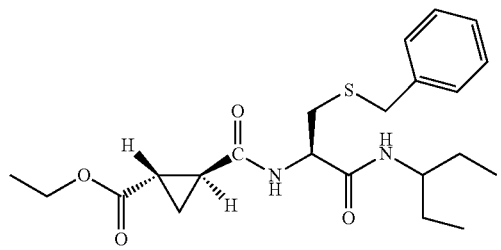

Compound 43

3-Aminopentane and Intermediate 4 were used as raw materials, and operations were performed as they were in Example 25, to get Compound 43, as white solid.

$^1$H-NMR (400 MHz, DMSO) 0.86 (6H, t) 1.21-1.43 (7H, m) 2.7 (2H, m) 2.90-3.20 (1H, m) 3.55-3.72 (4H, m) 4.16-4.34 (2H, m) 4.56 (1H, q) 7.10-7.31 (5H, m) 8.06-8.09 (1H, t) 8.63 (1H, d) EI-MS (m/z): 423 [M+H]$^+$.

Example 40 (2s, 3s)-2-ethoxycarbonyl-3-[2-[(s)-3-benzylthio-1-carbonyl-1-(isobutylamino)propane]formylamino]epoxysuccinic acid (Compound 44)

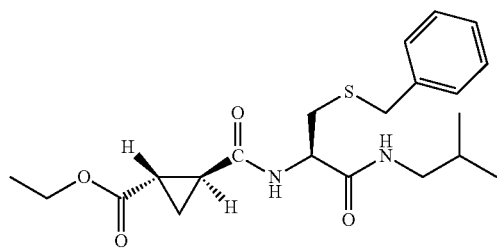

Compound 44

Isobutylamine and Intermediate 4 were used as raw materials, and operations were performed as they were in Example 25, to get Compound 44, as yellow oil.

$^1$H-NMR (400 MHz, DMSO) 0.80 (6H, d) 1.21-1.43 (4H, m) 2.50-2.71 (2H, m) 2.90-3.20 (2H, m) 3.55-3.72 (4H, m) 4.16-4.34 (2H, m) 4.56 (1H, q) 7.10-7.30 (5H, m) 8.06-8.09 (1H, t) 8.63 (1H, d) EI-MS (m/z): 409[M+H]$^+$.

Example 41 (2s, 3s)-2-ethoxycarbonyl-3-[2-[(s)-3-benzylthio-1-carbonyl-1-(3-phenyl propylamino)propane]formylamino]epoxysuccinic acid (Compound 45)

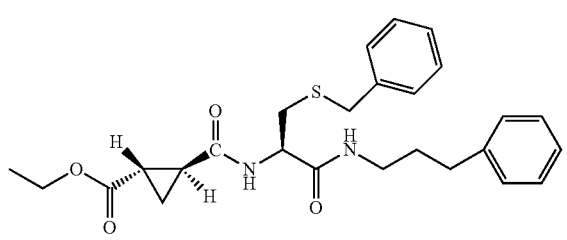

Compound 45

3-Phenylpropylamine and Intermediate 4 were used as raw materials, and operations were performed as they were in Example 25, to get Compound 45, as yellow oil.

$^1$H-NMR (400 MHz, DMSO) 1.21-1.3 (5H, m) 1.50-1.88 (2H, m) 2.50-2.71 (2H, m) 3.00-3.10 (2H, m) 3.61-3.72 (4H, m) 4.16-4.34 (2H, m) 4.56 (1H, q) 7.10-7.27 (1 OH, m) 8.06-8.09 (1H, t) 8.63 (1H, d) EI-MS (m/z): 471 [M+H]$^+$.

Example 42 (2s, 3s)-2-ethoxycarbonyl-3-[2-[(s)-3-benzylthio-1-carbonyl-1-(thiomorpholinyl)propane]formylamino]epoxysuccinic acid (Compound 46)

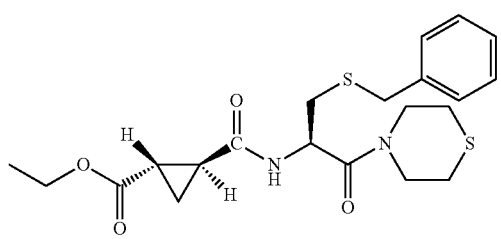

Compound 46

Thiomorpholine and Intermediate 4 were used as raw materials, and operations were performed as they were in Example 25, to get Compound 46, as white oil.

$^1$H-NMR (400 MHz, DMSO) 1.21 (3H, t) 2.42-2.70 (6H, m) 3.60-3.72 (4H, m) 3.9 (4H. t) 4.16-4.34 (2H, m) 4.56 (1H, q) 7.0-7.30 (5H, m) 8.81 (1H, d) EI-MS (m/z): 439 [M+H]$^+$.

Example 43 (2s, 3s)-2-ethoxycarbonyl-3-[2-[(s)-3-benzylthio-1-carbonyl-1-(tetrahydrothiazolyl)propane]formylamino]epoxysuccinic acid (Compound 47)

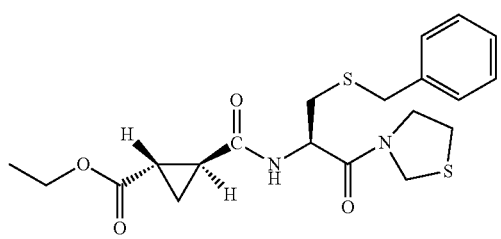

Compound 47

Tetrahydrothiazole and Intermediate 4 were used as raw materials, and operations were performed as they were in Example 25, to get Compound 47, as colorless oil.

$^1$H-NMR (400 MHz, DMSO) 1.21 (3H, t) 2.50-2.71 (2H, m) 3.03 (2H, m) 3.60-3.72 (4H, m) 3.89 (2H, m) 4.16-4.34 (2H, m) 4.44 (2H, dd) 4.56 (1H, q) 7.10-7.30 (5H, m) 8.87 (1H, d) EI-MS (m/z): 425 [M+H]$^+$.

Example 44 (2s, 3s)-2-ethoxycarbonyl-3-[2-[(s)-3-benzylthio-1-carbonyl-1-(3-methyl piperidinyl)propane]formylamino]epoxysuccinic acid (Compound 48)

Compound 48

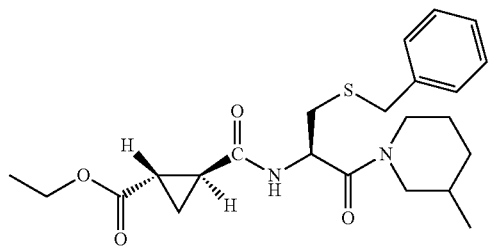

3-Methylpiperidine and Intermediate 4 were used as raw materials, and operations were performed as they were in Example 25, to get Compound 48, as yellow oil.
$^1$H-NMR (400 MHz, DMSO) 0.8 (3H, d) 1.21 (3H, t) 1.41-1.97 (5H, m) 2.50-2.71 (2H, m) 3.50-3.72 (8H, m) 4.16-4.34 (2H, m) 4.56 (1H, q) 7.10-7.30 (5H, m) 8.71 (1H, d) EI-MS (m/z): 435[M+H]$^+$.

Example 45 (2s, 3s)-2-ethoxycarbonyl-3-[2-[(s)-3-benzylthio-1-carbonyl-1-(2-ethyl piperidinyl)propane]formylamino]epoxysuccinic acid (Compound 49)

Compound 49

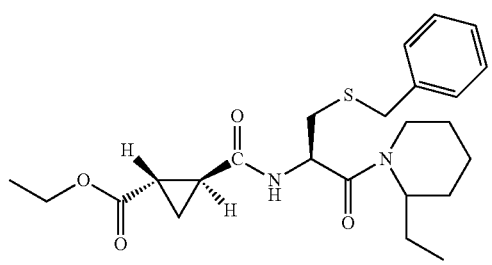

2-Ethylpiperidine and Intermediate 4 were used as raw materials, and operations were performed as they were in Example 25, to get Compound 49, as yellow oil.
$^1$H-NMR (400 MHz, DMSO) 0.90 (3H, d) 1.21 (3H, t) 1.41-1.97 (8H, m) 2.50-2.71 (2H, m) 3.50-3.72 (7H, m) 4.16-4.34 (2H, m) 4.56 (1H, q) 7.10-7.30 (5H, m) 8.71 (1H, d) EI-MS (m/z): 449[M+H]$^+$.

Example 46 (2s, 3s)-2-ethoxycarbonyl-3-[2-[(s)-3-benzylthio-1-carbonyl-1-(3,5-dimethyl piperidinyl) propane]formylamino]epoxysuccinic acid (Compound 50)

Compound 50

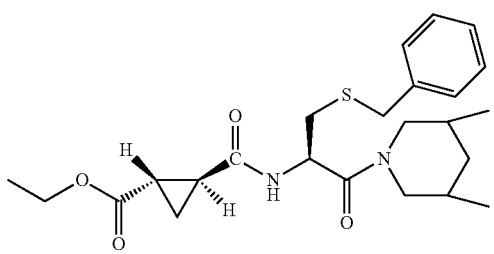

3,5-Dimethylpiperidine and Intermediate 4 were used as raw materials, and operations were performed as they were in Example 25, to get Compound 50, as yellow oil.
$^1$H-NMR (400 MHz, DMSO) 0.80 (6H, m) 1.21 (3H, t) 1.41-1.97 (4H, m) 2.50-2.71 (2H, m) 3.50-3.72 (8H, m) 4.16-4.34 (2H, m) 4.56 (1H, q) 7.10-7.31 (5H, m) 8.71 (1H, d) EI-MS (m/z): 449[M+H]$^+$ Example 47 (2s, 3s)-2-ethoxycarbonyl-3-[2-[(s)-3-benzylthio-1-carbonyl-1-(isopentyl amino)propane] formylamino]epoxysuccinic acid (Compound 51)

Compound 51

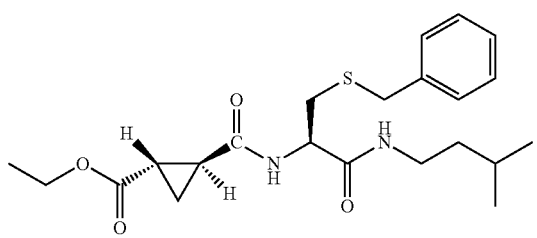

Isopentylamine and Intermediate 4 were used as raw materials, and operations were performed as they were in Example 25, to get Compound 51, as white oil.
$^1$H-NMR (400 MHz, DMSO) 0.86 (6H, d) 1.20-1.31 (5H, m) 1.54 (1H, m) 2.50-2.71 (2H, m) 2.90-3.20 (2H, m) 3.61-3.72 (3H, m) 4.16 (2H, m) 4.56 (1H, q) 7.10-7.30 (5H, m) 8.06-8.09 (1H, t) 8.63 (1H, d) EI-MS (m/z): 443[M+H]$^+$.

Example 48 (2s, 3s)-2-ethoxycarbonyl-3-[2-[(s)-3-benzylthio-1-carbonyl-1-(pentylamino) propane] formylamino]epoxysuccinic acid (Compound 52)

Compound 52

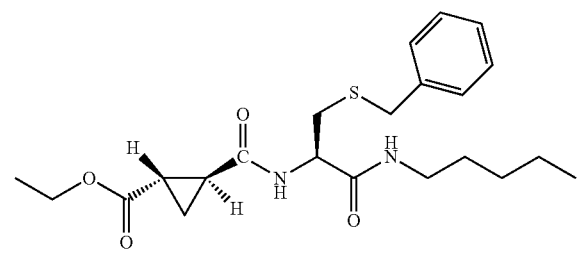

Pentylamine and Intermediate 4 were used as raw materials, and operations were performed as they were in Example 25, to get Compound 52, as white oil.
$^1$H-NMR (400 MHz, DMSO) 0.86 (3H, d) 1.17-1.37 (9H, m) 2.50-2.70 (2H, m) 2.90-3.20 (2H, m) 3.61-3.72 (4H, m) 4.16 (2H, m) 4.56 (1H, q) 7.10-7.30 (5H, m) 8.06-8.09 (1H, t) 8.63 (1H, d) EI-MS (m/z): 443 [M+H]$^+$.

Experimental example: Evaluation of activity of cathepsin inhibitors in the present invention In the present invention, the activity of cathepsin inhibitors could be evaluated by the following methods.

1. Method for preliminary screening of Cathepsin K:

Preliminary screening of Cathepsin K was performed by using Cathepsin K Inhibitor Screening Kit (Product No. K150-100) from Biovision Company.

The test compounds were the compounds prepared in the above Examples, the positive compound FF-FMK was provided in the Kit, and the positive compounds zxy-37 (E64d) and zxy-60 (CA-074) were purchased from Selleck Company.

1.1 Preparation work:

1.1.1 Preparation of Cathepsin K enzyme solution: Cathepsin K enzyme (40 μl) and Cathepsin K reagent (80 μl) were added to Cathepsin K buffer (3.88 ml), and were mixed well, to prepare Cathepsin K enzyme solution with a volume of 4 ml, which was placed on ice for further use.

1.1.2 Preparation of a compound solution: different compounds were separately weighed and dissolved in DMSO (methyl sulfoxide), to prepare solutions at a concentration of 30 mM as stock solutions, and for some insoluble compounds, they were prepared into solutions at a concentration of 10 mM as stock solutions; the 30 mM and 10 mM compound stock solutions were diluted to 1 mM and 100 μM DMSO solutions, respectively; 1 mM and 100 μM compound DMSO solutions (2 μl) were separately added to CTSK buffer (18 μl), to prepare compound solutions at a final concentration of 100 μM and 10 μM, respectively, wherein the concentration of DMSO was 10%.

The positive control drugs were zxy-37 (E64d) and zxy-60 (CA-074), respectively.

1.1.3 Preparation of Cathepsin K substrate solution: Cathepsin K substrate (160 μl) was added to Cathepsin K buffer (3.44 ml), and mixed homogeneously, to prepare Cathepsin K substrate solution with a volume of 3.6 ml, which was placed on ice for further use.

1.2 Method for screening Cathepsin K inhibitor: Cathepsin K enzyme solution (prepared in Item 1.1.1) was added to a 384-well plate (ProxiPlate-384 Plus, Perkinelmer) at 10 μl/well, and centrifuged at 1000 rpm for 1 min; the compound solution (prepared in Item 1.1.2) was then added at 2 l/well, and centrifuged at 1000 rpm for 1 min, and every concentration was repeated in two wells; the plate was placed in a 25° C. incubator for 15 min; Cathepsin K substrate solution was then added at 8 μl/well, and centrifuged at 1000 rpm for 1 min; and finally, the fluorescence signal was read in Enspire, wherein the exciting light was at a wavelength of 400 nm, the emitting light was at a wavelength of 505 nm, and continuous reading was performed at 37° C. for 120 min.

1.3 Data analysis: the slope (S) for all the samples was calculated by ΔRFU (RFU2−RFU1) and time ΔT (T2−T1), including negative control (Enzyme Control, EC) and positive control (Inhibitor Control, IC: 10 μM FF-FMK), and the calculation formula was as followed: Relative inhibition rate %=$(S_{EC}-S_S)/(S_{EC}-S_{IC})$*100. The screening result was shown in Table 1.

TABLE 1

The inhibitory activity of the compounds according to the present invention against Cathepsin K

| Compound | Inhibition % (10 μM) | | Inhibition % (1 μM) | |
| --- | --- | --- | --- | --- |
| | replicate 1 | replicate 2 | replicate 1 | replicate 2 |
| Compound 1 | 41.60 | 47.08 | 17.79 | 20.59 |
| Compound 2 | 59.49 | 59.95 | 28.60 | 33.16 |
| Compound 3 | 42.04 | 36.66 | 30.96 | 16.58 |
| Compound 4 | 31.56 | 34.93 | 15.64 | 23.63 |
| Compound 5 | 91.35 | 95.67 | 90.89 | 89.50 |
| Compound 6 | 33.01 | 39.06 | 31.62 | 36.65 |
| Compound 7 | 37.40 | 28.37 | 32.97 | −19.60 |
| Compound 8 | 96.93 | 94.07 | 80.55 | 78.86 |

TABLE 1-continued

The inhibitory activity of the compounds according to the present invention against Cathepsin K

| Compound | Inhibition % (10 μM) | | Inhibition % (1 μM) | |
| --- | --- | --- | --- | --- |
| | replicate 1 | replicate 2 | replicate 1 | replicate 2 |
| Compound 9 | 29.17 | 28.84 | 25.65 | 18.08 |
| Compound 10 | 80.25 | 66.52 | 33.15 | 35.75 |
| Compound 11 | 31.97 | 15.15 | 15.29 | −7.42 |
| Compound 12 | 43.95 | 51.69 | 15.43 | 26.63 |
| Compound 13 | 107.72 | 106.22 | 99.70 | 98.94 |
| Compound 14 | 42.39 | 41.33 | 31.16 | −7.18 |
| Compound 15 | 50.13 | 48.62 | 28.11 | 35.58 |
| Compound 16 | 60.81 | 63.59 | 38.93 | 39.18 |
| Compound 17 | 34.83 | 31.73 | 26.88 | 32.24 |
| Compound 18 | 56.08 | 48.16 | 23.53 | 32.70 |
| Compound 19 | 33.50 | 27.92 | 32.04 | 20.41 |
| Compound 20 | 36.32 | 50.42 | 30.22 | 36.97 |
| Compound 21 | 67.19 | 52.97 | 33.11 | 29.92 |
| Compound 22 | 29.66 | 19.49 | 16.04 | −4.45 |
| Compound 23 | 70.09 | 63.02 | 16.07 | 37.70 |
| Compound 24 | 66.31 | 65.89 | 12.93 | 33.13 |
| Compound 25 | 48.81 | 48.92 | 40.04 | 35.71 |
| Compound 26 | 67.87 | 63.25 | 35.73 | 44.11 |
| Compound 30 | 29.57 | 31.73 | 31.56 | 26.85 |
| Compound 31 | 44.08 | 45.42 | 30.52 | 36.65 |
| Compound 32 | 36.16 | 40.62 | 37.54 | 38.69 |
| Compound 33 | 34.87 | 36.02 | 36.59 | 33.07 |
| Compound 34 | 94.42 | 95.74 | 88.59 | 90.80 |
| Compound 35 | 72.01 | 61.14 | 37.80 | 22.82 |
| Compound 36 | 61.37 | 63.50 | 17.54 | 21.65 |
| Compound 38 | 44.29 | 41.38 | 36.76 | 37.86 |
| Compound 39 | 97.31 | 99.48 | 81.49 | 85.22 |
| Compound 40 | 91.08 | 94.94 | 85.45 | 89.08 |
| Compound 41 | 64.16 | 61.05 | 32.09 | 30.77 |
| Compound 42 | 24.37 | 32.01 | 26.13 | 22.58 |
| Compound 43 | 38.66 | 36.83 | 29.13 | 24.64 |
| Compound 44 | 28.03 | 22.18 | 13.44 | 21.77 |
| Compound 45 | 39.85 | 36.37 | 19.44 | 18.71 |
| Compound 46 | 38.92 | 20.49 | 22.29 | −6.20 |
| Compound 47 | 23.24 | 25.44 | 11.77 | 15.40 |
| Compound 48 | 34.35 | 31.06 | 17.14 | 11.34 |
| Compound 49 | 64.89 | 46.56 | 24.28 | 19.80 |
| Compound 50 | 35.01 | 29.99 | 31.62 | 18.96 |
| Compound 51 | 39.50 | 32.25 | 27.65 | 21.10 |
| Compound 52 | 57.86 | 52.08 | 20.38 | 22.74 |
| zxy-37 | 90.96 | 98.34 | 85.73 | 87.75 |
| zxy-60 | 94.49 | 91.36 | 88.44 | 92.44 |

2. Method for determining $IC_{50}$ of compounds against cathepsin:

$IC_{50}$ of compounds against Cathepsin B was determined by using Cathepsin B Inhibitor Screening Kit (Product No. K147-100) from Biovision Company;

$IC_{50}$ of compounds against Cathepsin K was determined by using Cathepsin K Inhibitor Screening Kit (Product No. K150-100) from Biovision Company;

$IC_{50}$ of compounds against Cathepsin L was determined by using Cathepsin L Inhibitor Screening Kit (Product No. K161-100) from Biovision Company;

$IC_{50}$ of compounds against Cathepsin S was determined by using Cathepsin S Inhibitor Screening Kit (Product No. K149-100) from Biovision Company.

The test compounds were prepared in the Examples above, the positive compounds FF-FMK, F-F-FMK, FF-FMK and Z-FF-FMK were provided in the Kits, and the positive compounds zxy-37 (E64d) and zxy-60 (CA-074) were purchased form Selleck Company.

2.1 Preparation work:

2.1.1 Preparation of Cathepsin solution:

2.1.1.1 Preparation of Cathepsin K solution: Cathepsin K enzyme (23 μl) and Cathepsin K reagent (46 μl) were added to Cathepsin K buffer (2231 μl), and mixed well, to prepare Cathepsin K enzyme solution with a volume of 2.3 ml, which was placed on ice for further use.

2.1.1.2 Preparation of Cathepsin B solution: Cathepsin B enzyme (23 μl) and Cathepsin B reagent (46 μl) were added to Cathepsin B buffer (2231 μl), and mixed well, to prepare Cathepsin B enzyme solution with a volume of 2.3 ml, which was placed on ice for further use.

2.1.1.3 Preparation of Cathepsin L solution: Cathepsin L reagent (3 μl) was added to Cathepsin L enzyme (3 μl), mixed well, and on standing for 1 h, to get 1 mU/μl Cathepsin L enzyme solution. Cathepsin L buffer (24 μl) was added to 1 mU/μl cathepsin L enzyme solution (6 μl), to get 0.2 mU/μl Cathepsin L enzyme solution. 0.2 mU/μl cathepsin L enzyme (23 μl), and DTT (46 μl) were added to Cathepsin L buffer (2231 μl), and mixed well, to prepare Cathepsin L enzyme solution with a volume of 2.3 ml, which was placed on ice for further use.

2.1.1.4 Preparation of Cathepsin S solution: Cathepsin S enzyme (46 μl) was added to Cathepsin S buffer (2254 μl), and mixed well, to prepare Cathepsin S enzyme solution with a volume of 2.3 ml, which was placed on ice for further use.

2.1.2 Preparation of compound solutions: 30 mM and 10 mM compound stock solutions, and control compounds were gradiently diluted in DMSO at a ratio of 1:3, wherein the maximum dilution fold was 19683; the gradiently diluted compound solution (3 μl) was added to Cathepsin K, B, L, and S buffer (27 μl), respectively, and mixed well, wherein the control compounds (FF-FMK, F-F-FMK, FF-FMK and Z-FF-FMK) were at the concentrations of 66.67, 22.22, 7.41, 2.47, 0.82, 0.27, 0.091, 0.03, 0.01, 0.0034 and 0 μM, respectively, the test compounds were at the concentrations of 1000, 333.3, 111.1, 37, 12.3, 4.1, 1.4, 0.46, 0.15, 0.05 and 0 μM, respectively, and the final concentration of DMSO was 10%.

2.1.3 Preparation of cathepsin substrate solutions:

2.1.3.1 Cathepsin K: Cathepsin K substrate (90 μl) was added to Cathepsin K buffer (1710 μl), and mixed well, to prepare Cathepsin K substrate solution with a volume of 1.8 ml, which was placed on ice for further use.

2.1.3.2 Cathepsin B: Cathepsin B substrate (90 μl) was added to Cathepsin B buffer (1710 μl), and mixed well, to prepare Cathepsin B substrate solution with a volume of 1.8 ml, which was placed on ice for further use.

2.1.3.3 Cathepsin L: Cathepsin L substrate (45 μl) was added to Cathepsin L buffer (1755 μl), and mixed well, to prepare Cathepsin L substrate solution with a volume of 1.8 ml, which was placed on ice for further use.

2.1.3.4 Cathepsin S: Cathepsin S substrate (90 μl) was added to Cathepsin S buffer (1710 μl), and mixed well, to prepare Cathepsin S substrate solution with a volume of 1.8 ml, which was placed on ice for further use.

Method for screening cathepsin inhibitors: the cathepsin solution (prepared in Item 2.1.1) was added to a 384-well plate (ProxiPlate-384 Plus, Perkinelmer) at 10 μl/well, and centrifuged at 1000 rpm for 1min; the compound solution (prepared in Item 2.1.2) was then added at 2 μl/well, and every concentration was repeated in two wells; the final concentrations of the test compounds were 100, 33.3, 11.1, 3.7, 1.23, 0.41, 0.14, 0.046, 0.015, 0.005 and 0 μM, respectively, wherein the final concentration of DMSO was 1%; after centrifugation at 1000 rpm for 1 min, the plate was put in a 25° C. incubator for 15 min; the cathepsin substrate solution was then added at 8 l/well, and centrifuged at 1000 rpm for 1 min; and finally, the fluorescence signal was read in Enspire, wherein the exciting light was at a wavelength of 400 nm, the emitting light was at a wavelength of 505 nm, and continuous reading was performed at 37° C. for 120 min.

Data analysis: the slope (S) for all the samples was calculated by ΔRFU(RFU2−RFU1) and time ΔT(T2−T1), including negative control (Enzyme Control, EC) and positive control (Inhibitor Control, IC: 10 μM (FF-FMK, F-F-FMK, FF-FMK and Z-FF-FMK), and the calculation formula was as followed: Relative inhibition rate %=$(S_{EC}-S_S)/(S_{EC}-S_{IC})*100$. The $IC_{50}$ for each compound was obtained by means of fitting by software GraphPad Prism 5.0.

The screening results of four enzymes were shown in Table 2.

TABLE 2

$IC_{50}$ of inhibitory activity of the compounds according to the present invention against cathepsin

| Compound ID | $IC_{50}$ (nM) Exp-1 | Exp-2 | Ave of IC50 (nM) | STDEV |
|---|---|---|---|---|
| $IC_{50}$ determination on CTSK | | | | |
| zxy-37 | 488.30 | 465.40 | 476.85 | 16.19 |
| zxy-60 | 251.70 | 244.70 | 248.20 | 4.95 |
| Compound 5 | 1684.00 | 1315.00 | 1499.50 | 260.92 |
| Compound 8 | 2951.00 | 1496.00 | 2223.50 | 1028.84 |
| Compound 13 | 180.00 | 147.90 | 163.95 | 22.69 |
| Compound 34 | 585.70 | 448.10 | 516.90 | 97.29 |
| Compound 39 | 1678.00 | 1613.00 | 1645.50 | 45.96 |
| Compound 40 | 704.50 | 606.30 | 655.40 | 69.43 |
| $IC_{50}$ determination on CTSB | | | | |
| zxy-37 | 10.59 | 13.46 | 12.03 | 2.02 |
| zxy-60 | 6.18 | 7.04 | 6.61 | 0.61 |
| Compound 5 | 7.19 | 9.33 | 8.27 | 1.51 |
| Compound 8 | 17.56 | 20.75 | 19.16 | 2.26 |
| Compound 13 | 3.76 | 4.64 | 4.20 | 0.63 |
| Compound 34 | 22.26 | 25.92 | 24.09 | 2.59 |
| Compound 39 | 68.48 | 80.05 | 74.27 | 8.18 |
| Compound 40 | 20.3 | 27.06 | 23.68 | 4.78 |
| $IC_{50}$ determination on CTSL | | | | |
| zxy-37 | 170.90 | 179.90 | 175.40 | 6.36 |
| zxy-60 | 392.40 | 449.80 | 421.10 | 40.59 |
| Compound 5 | 2271.00 | 2330.00 | 2300.50 | 41.72 |
| Compound 8 | 3608.00 | 4454.00 | 4031.00 | 598.21 |
| Compound 13 | 5881.00 | 6626.00 | 6253.50 | 526.79 |
| Compound 34 | 337.90 | 381.50 | 359.70 | 30.83 |
| Compound 39 | 9253.00 | 9955.00 | 9604.00 | 496.39 |
| Compound 40 | 4164.00 | 4611.00 | 4387.50 | 316.08 |
| $IC_{50}$ determination on CTSS | | | | |
| zxy-37 | 752.70 | 571.00 | 661.85 | 128.48 |
| zxy-60 | 3514.00 | 3233.00 | 3373.50 | 198.70 |
| Compound 5 | 4075.00 | 4138.00 | 4106.50 | 44.55 |
| Compound 8 | 10610.00 | 9454.00 | 10032.00 | 817.42 |
| Compound 13 | 1901.00 | 957.40 | 1429.20 | 667.23 |
| Compound 34 | 1601.00 | 1665.00 | 1633.00 | 45.25 |
| Compound 39 | 5107.00 | 8754.00 | 6930.50 | 2578.82 |
| Compound 40 | 833.60 | 1507.00 | 1170.30 | 476.17 |

The assay for evaluation of the activity of cathepsin inhibitors showed that the compound of Formula (1) according to the present invention, particularly Compound 5, 8, 13, 34, 39, and 40, had strong selectivity for Cathepsin B, as shown in the following table:

TABLE 3

Selectivity of the compounds according to the present invention for Cathepsin B

| Compound ID | Cathepsin B IC$_{50}$ (nM) | Selectivity vs | | |
|---|---|---|---|---|
| | | Cathepsin K (fold) | Cathepsin L (fold) | Cathepsin S (fold) |
| zxy-37 | 12.03 ± 2.03 | 39 | 15 | 55 |
| zxy-60 | 6.61 ± 0.61 | 38 | 64 | 510 |
| Compound 5 | 8.27 ± 1.51 | 181 | 278 | 497 |
| Compound 8 | 19.16 ± 2.26 | 116 | 210 | 524 |
| Compound 13 | 4.20 ± 0.63 | 40 | 1563 | 357 |
| Compound 34 | 24.09 ± 2.59 | 21 | 115 | 167 |
| Compound 39 | 74.27 ± 8.18 | 22 | 129 | 193 |
| Compound 40 | 23.68 ± 4.78 | 28 | 185 | 149 |

Although the embodiments of the present invention have been described in detail, a person skilled in the art would understand that according to all the disclosed teachings, details can be amended and replaced, and all these changes fall into the protection scope of the invention. The whole scope of the present invention is defined by the attached claims and any equivalent thereof.

What is claimed is:

1. A compound represented by Formula (1), a racemate or an optical isomer thereof, a solvate thereof, or a pharmaceutically acceptable salt thereof,

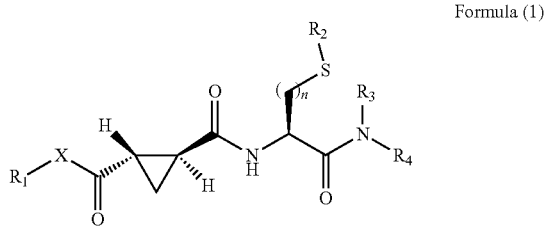

Formula (1)

wherein,
$R_1$ represents a hydrogen atom, $C_1$-$C_{10}$ linear or branched alkyl, $C_3$-$C_{10}$cycloalkyl, $C_2$-$C_{10}$ linear or branched alkenyl, $C_2$-$C_{10}$ linear or branched alkynyl;
$R_2$ represents a hydrogen atom, $C_1$-$C_{10}$ linear or branched alkyl, $C_3$-$C_{10}$cycloalkyl, $C_2$-$C_{10}$ linear or branched alkenyl, $C_2$-$C_{10}$ linear or branched alkynyl, phenyl, phenyl-$C_1$-$C_6$alkyl, optionally, wherein the $C_1$-$C_{10}$ linear or branched alkyl, $C_3$-$C_{10}$cycloalkyl, $C_2$-$C_{10}$ linear or branched alkenyl, $C_2$-$C_{10}$ linear or branched alkynyl, phenyl, or phenyl-$C_1$-$C_6$alkyl each is independently substituted with one or more substituents selected from the group consisting of: halogen, amino, cyano, trifluoromethyl, hydroxyl, nitro, $C_1$-$C_{10}$alkyl, $C_1$-$C_{10}$alkoxy and $C_1$-$C_{10}$alkylthio, optionally, wherein the $C_1$-$C_{10}$alkyl, $C_1$-$C_{10}$alkoxy or $C_1$-$C_{10}$alkylthio is further substituted with one or more substituents selected from the above-mentioned group;
X represents —O—, or —N($R_5$)—;
n is an integer from 0 to 5;
$R_3$ and $R_4$ each independently represent a hydrogen atom, $C_1$-$C_{10}$ linear or branched alkyl, $C_3$-$C_{10}$cycloalkyl, phenyl, or phenyl-$C_1$-$C_6$alkyl, optionally, wherein the $C_1$-$C_{10}$ linear or branched alkyl, $C_3$-$C_{10}$cycloalkyl, phenyl, or phenyl-$C_1$-$C_6$alkyl each is independently substituted from the group consisting of: halogen and $C_1$-$C_{10}$alkyl, optionally, wherein the $C_1$-$C_{10}$alkyl is further substituted with one or more substituents selected from the above-mentioned group; or,
$R_3$ and $R_4$, together with the N atom to which they are linked, form a 5-8 membered heterocycle, and the 5-8 membered heterocycle is piperidine, tetrahydropyrrole or tetrahydrothiazole, optionally, the 5-8 membered heterocycle is substituted with one or more substituents selected from the group consisting of: halogen, hydroxyl, amino, $C_1$-$C_{10}$alkyl, $C_1$-$C_{10}$alkoxy, $C_1$-$C_{10}$alkylthio, phenyl, oxy and ester group;
$R_5$ represents a hydrogen atom, or $C_1$-$C_{10}$ linear or branched alkyl.

2. The compound represented by Formula (1), a racemate or an optical isomer thereof, a solvate thereof, or a pharmaceutically acceptable salt thereof according to claim 1,
wherein,
$R_3$ and $R_4$, together with the N atom to which they are linked, form 3-methylpiperidine, 2-ethylpiperidine, 3,5-dimethylpiperidine, 4-phenylpiperidine, tetrahydropyrrole, or tetrahydrothiazole.

3. The compound represented by Formula (1), a racemate or an optical isomer thereof, a solvate thereof, or a pharmaceutically or physiologically acceptable salt thereof according to claim 1,
$R_1$ represents a hydrogen atom or $C_1$-$C_5$ linear or branched alkyl;
$R_2$ represents a hydrogen atom, $C_1$-$C_6$ linear or branched alkyl or phenyl-$C_1$-$C_4$alkyl;
X is —O—;
n is 1 or 2;
$R_3$ and $R_4$ each independently represent $C_1$-$C_{10}$ linear or branched alkyl, $C_3$-$C_{10}$cycloalkyl, phenyl, or phenyl-$C_1$-$C_6$alkyl, optionally, wherein the $C_1$-$C_{10}$ linear or branched alkyl, $C_3$-$C_{10}$cycloalkyl, phenyl, or phenyl-$C_1$-$C_6$alkyl each is independently substituted with one or more substituents selected from the group consisting of: halogen and $C_1$-$C_{10}$alkyl, optionally, wherein the $C_1$-$C_{10}$alkyl is further substituted with one or more substituents selected from the above-mentioned group; or,
$R_3$ and $R_4$, together with the N atom to which they are linked, form a 5-8 membered heterocycle, and the 5-8 membered heterocycle is piperidine, tetrahydropyrrole or tetrahydrothiazole, optionally, wherein the 5-8 membered heterocycle is substituted with one or more substituents selected from the group consisting of: halogen, $C_1$-$C_{10}$alkyl, $C_1$-$C_6$alkoxy, $C_1$-$C_6$alkylthio, aryl, oxy and ester group.

4. The compound represented by Formula (1), a racemate or an optical isomer thereof, a solvate thereof, or a pharmaceutically acceptable salt thereof according to claim 1,
wherein,
$R_1$ represents $C_{1-4}$alkyl;
$R_2$ represents $C_1$-$C_4$alkyl or aryl-$C_1$-$C_4$alkyl;
X is —O—;
n is 1 or 2;
$R_3$ and $R_4$ each independently represent $C_1$-$C_6$ linear or branched alkyl, or phenyl-$C_1$-$C_6$alkyl, optionally, wherein the $C_1$-$C_6$ linear or branched alkyl and the phenyl-$C_1$-$C_6$alkyl each are independently substituted with one or more substituents selected from the group consisting of halogen and $C_1$-$C_4$alkyl; or,
$R_3$ and $R_4$, together with the N atom to which they are linked, form a 5-8 membered heterocycle, and the 5-8 membered heterocycle is piperidine, tetrahydropyrrole or tetrahydrothiazole, optionally, wherein the 5-8 membered heterocycle is substituted with one or more substituents selected from the group consisting of: $C_1$-$C_4$alkyl, $C_1$-$C_4$alkoxy and phenyl.

5. The compound represented by Formula (1), a racemate or an optical isomer thereof, a solvate thereof, or a pharmaceutically acceptable salt thereof according to claim 1, wherein, $R_1$ is methyl or ethyl.

6. The compound represented by Formula (1), a racemate or an optical isomer thereof, a solvate thereof, or a pharmaceutically acceptable salt thereof according to claim 1, wherein, $R_2$ is methyl, ethyl or benzyl.

7. The compound represented by Formula (1), a racemate or an optical isomer thereof, a solvate thereof, or a pharmaceutically acceptable salt thereof according to claim 1, wherein, X is —O—.

8. The compound represented by Formula (1), a racemate or an optical isomer thereof, a solvate thereof, or a pharmaceutically acceptable salt thereof according to claim 1, wherein, n is 1 or 2.

9. A compound, a racemate or an optical isomer thereof, a solvate thereof, or a pharmaceutically acceptable salt thereof, wherein, the compound is selected from the group consisting of:

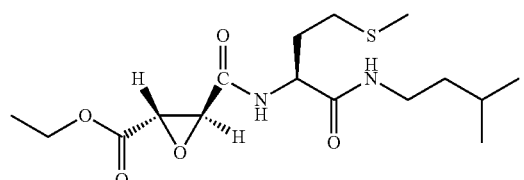

,

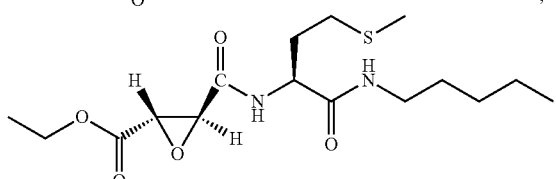

,

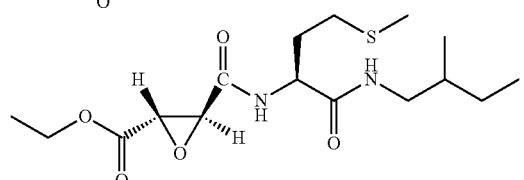

,

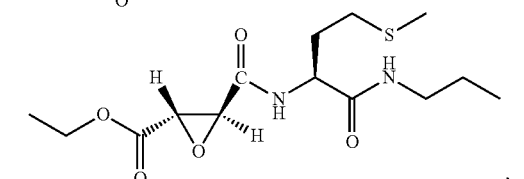

,

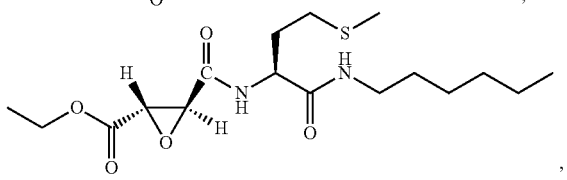

,

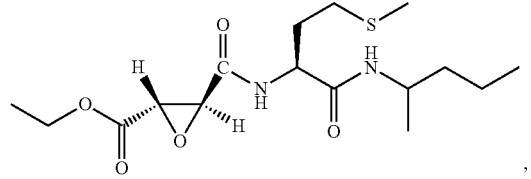

,

-continued

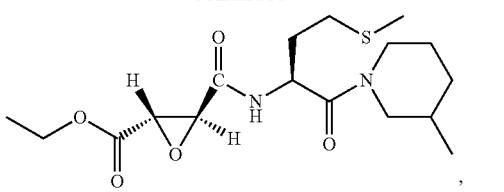

,

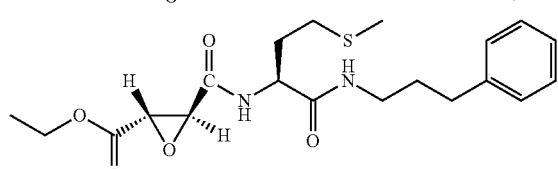

,

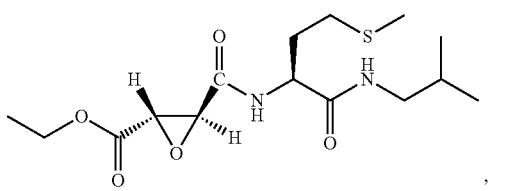

,

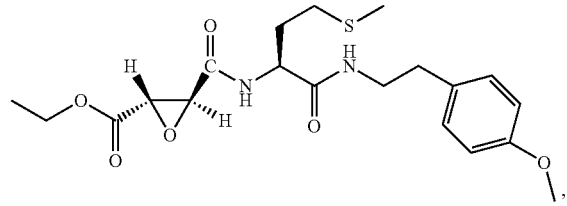

,

61
-continued
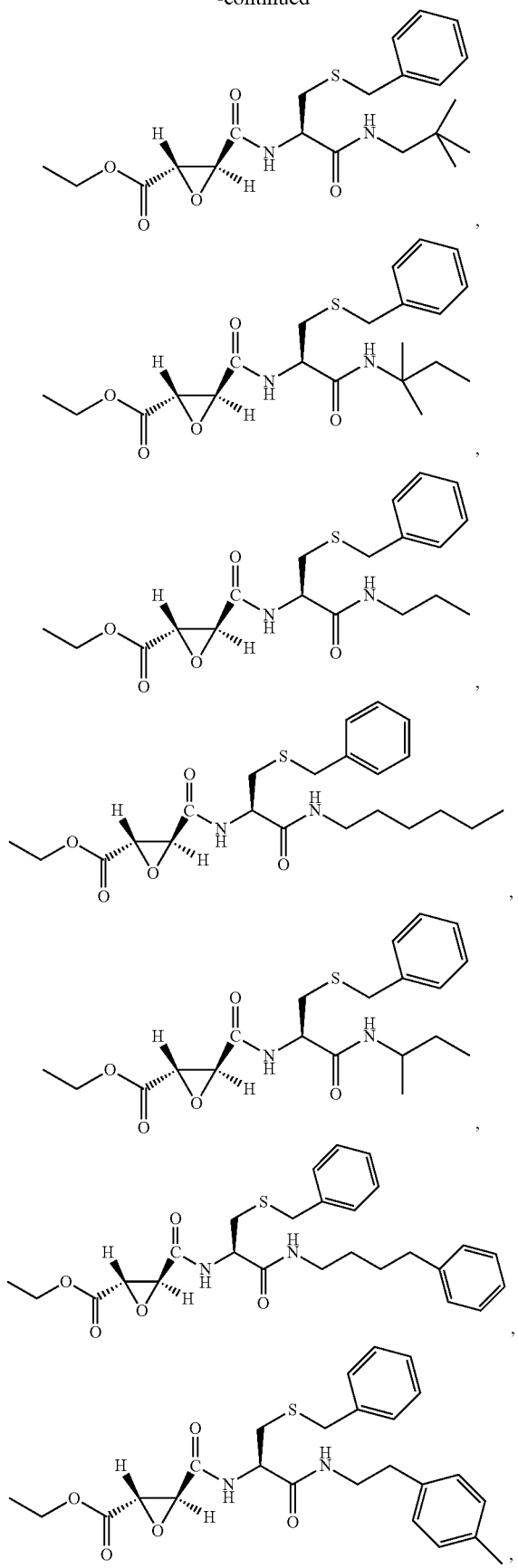
62
-continued
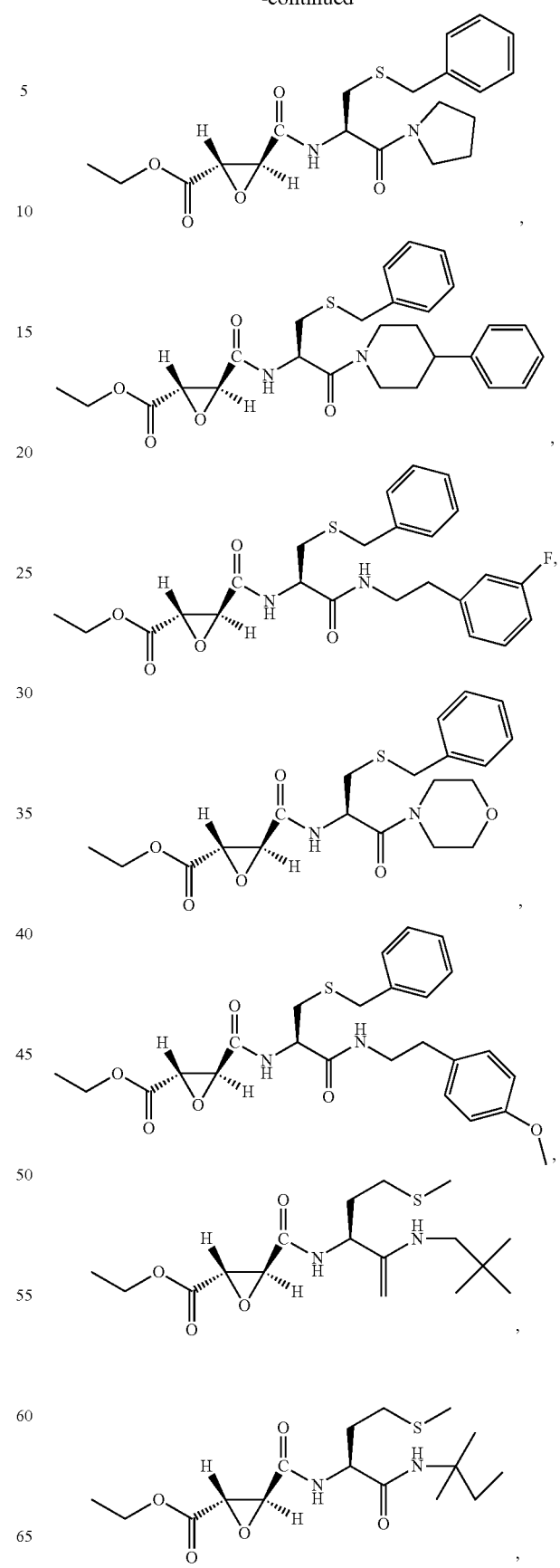

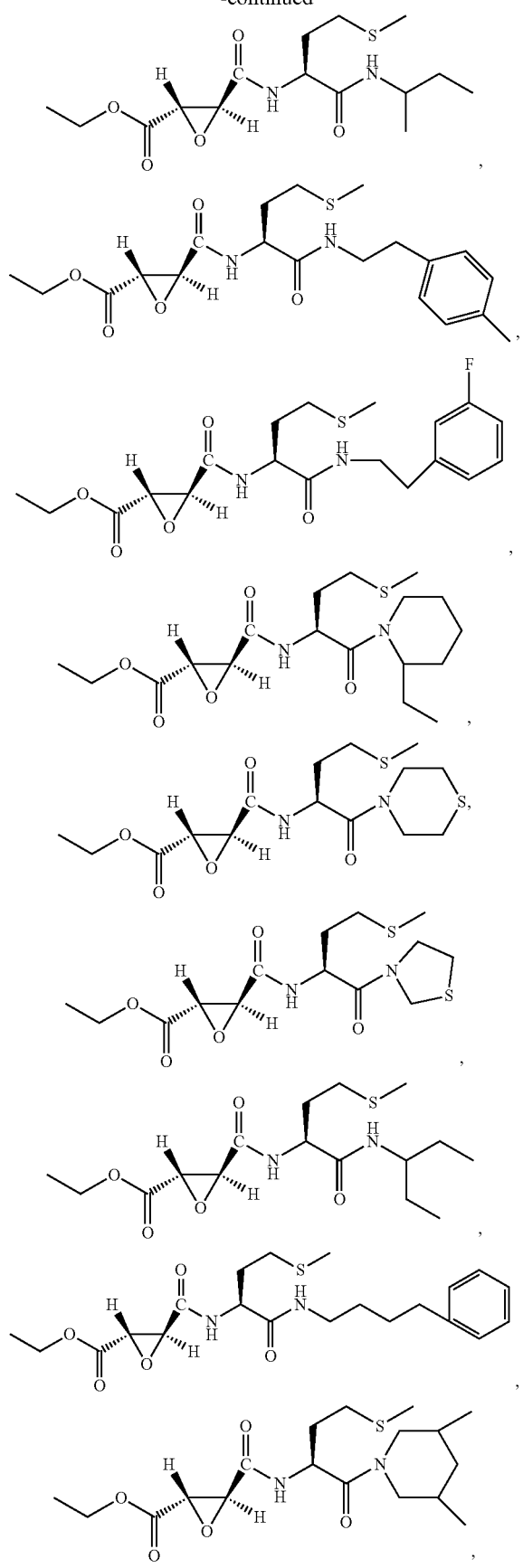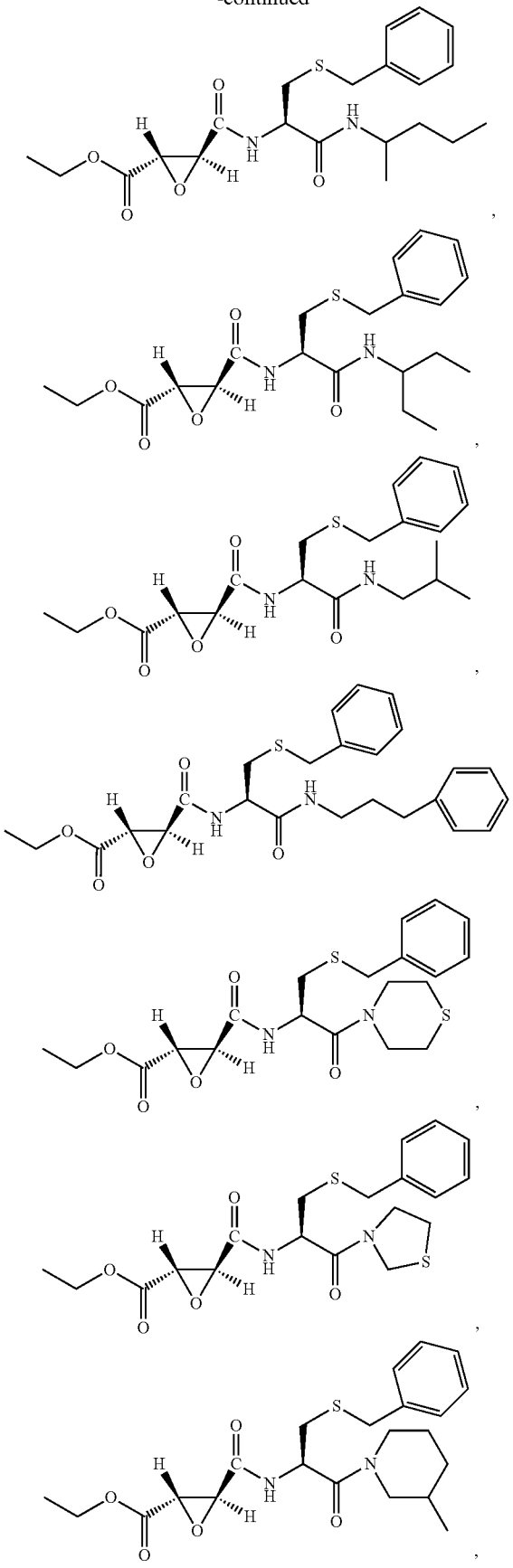

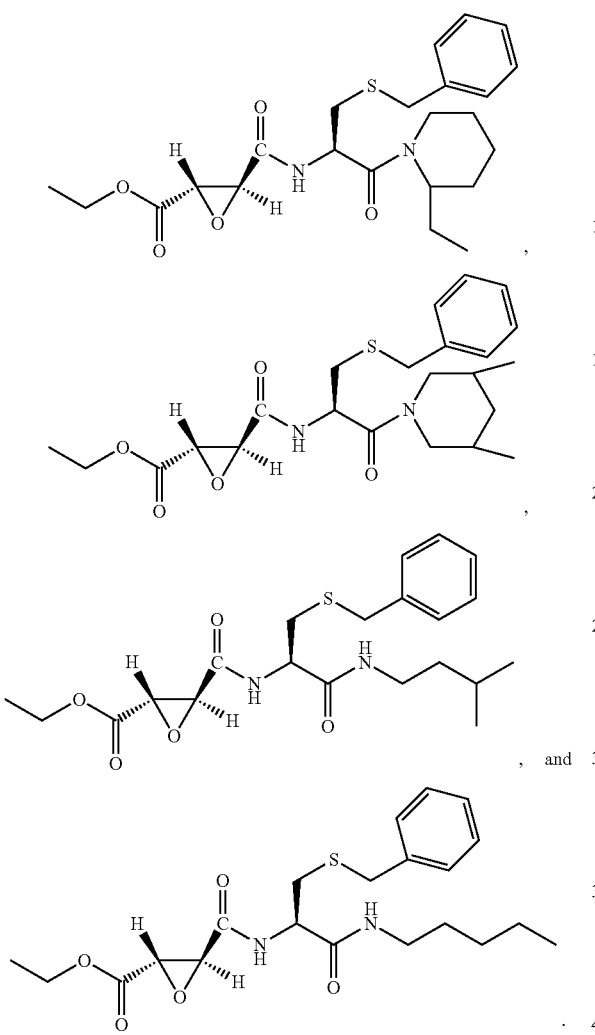

10. A method for preparing the compound represented by Formula (1), a racemate or an optical isomer thereof, a solvate thereof, or a pharmaceutically acceptable salt thereof according to claim 1, comprising the following steps:

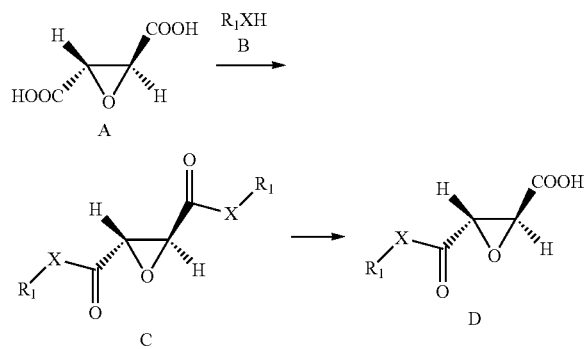

(1) Compound A and Compound B are subjected to esterification or amidation reaction to produce Compound C;
(2) Compound C is subjected to selective hydrolysis to produce Compound D;
(3) Compound E and Compound F are subjected to condensation to produce Compound G;
(4) the amino-protecting group is removed from Compound G to produce Compound H; and
(5) Compound H and the Compound D obtained in step (2) are subjected to condensation to produce a compound of Formula (1),
Wherein n, $R_1$, $R_2$, $R_3$ and $R_4$ have the same meaning as defined in claim 1.

11. A pharmaceutical composition, comprising the compound represented by Formula (1), a racemate or an optical isomer thereof, a solvate thereof, or a pharmaceutically acceptable salt thereof according to claim 1, and optionally one or more pharmaceutically acceptable carriers or excipients.

12. A method for inhibition of cathepsin activity, comprising administering to a subject in need thereof an effective amount of the compound represented by Formula (1), a racemate or an optical isomer thereof, a solvate thereof, or a pharmaceutically acceptable salt thereof according to claim 1.

13. The compound represented by Formula (1), a racemate or an optical isomer thereof, a solvate thereof, or a pharmaceutically acceptable salt thereof according to claim 1, wherein n is an integer from 1 to 3.

14. The compound represented by Formula (1), a racemate or an optical isomer thereof, a solvate thereof, or a pharmaceutically acceptable salt thereof according to claim 2, wherein n is 1 or 2.

15. The method for inhibition of cathepsin activity according to claim 12, wherein the cathepsin is selected from the group consisting of Cathepsin B, C, F, H, K, L, O, S, V, W and X.

16. The method for inhibition of cathepsin activity according to claim 15, wherein the cathepsin is selected from the group consisting of Cathepsin B, K, L and S.

* * * * *